(12) United States Patent
Tsopanoglou et al.

(10) Patent No.: US 9,180,163 B2
(45) Date of Patent: Nov. 10, 2015

(54) PARSTATIN PEPTIDES

(76) Inventors: Nikos Tsopanoglou, Rio-Patras Achaia (GR); Michael Maragoudakis, Kifisia Attiki (GR); Dimitrios Siablis, Rio-Patras (GR)

( * ) Notice: Subject to any disclaimer, the term of this patent is extended or adjusted under 35 U.S.C. 154(b) by 187 days.

(21) Appl. No.: 13/499,481

(22) PCT Filed: Aug. 5, 2010

(86) PCT No.: PCT/IB2010/002142
§ 371 (c)(1),
(2), (4) Date: Aug. 10, 2012

(87) PCT Pub. No.: WO2011/039584
PCT Pub. Date: Apr. 7, 2011

(65) Prior Publication Data
US 2013/0150298 A1 Jun. 13, 2013

Related U.S. Application Data

(63) Continuation of application No. 12/645,991, filed on Dec. 23, 2009, now Pat. No. 8,389,476, and a continuation of application No. 12/572,018, filed on Oct. 1, 2009, now abandoned.

(60) Provisional application No. 61/247,611, filed on Oct. 1, 2009.

(51) Int. Cl.
| | | |
|---|---|---|
| *A61K 38/00* | (2006.01) | |
| *A61K 38/17* | (2006.01) | |
| *A61K 38/16* | (2006.01) | |
| *C07K 14/705* | (2006.01) | |
| *C12N 5/071* | (2010.01) | |
| *A61K 38/10* | (2006.01) | |
| *C07K 7/08* | (2006.01) | |

(52) U.S. Cl.
CPC .............. *A61K 38/177* (2013.01); *A61K 38/10* (2013.01); *A61K 38/16* (2013.01); *C07K 7/08* (2013.01); *C07K 14/705* (2013.01); *C12N 5/069* (2013.01); *C12N 2501/48* (2013.01); *C12N 2501/998* (2013.01)

(58) Field of Classification Search
CPC .............................. C07K 14/705; A61K 38/16
See application file for complete search history.

(56) References Cited

U.S. PATENT DOCUMENTS 8,389,476 B2 3/2013 Tsopanoglou et al.
2008/0242613 A1 10/2008 Tsopanoglou et al.

FOREIGN PATENT DOCUMENTS

WO WO9816548 4/1998

OTHER PUBLICATIONS

Maragoudakis Michael E et al: "Parstatin: A New Cryptic Anti-Angiogenic Peptide", Anticancer Research, International Institute of Anticancer Research, GR, vol. 28, No. 5C, Sep. 1, 2008, pp. 3396-3397.
Routhu Kasi V et al: "Parstatin(1-26): The Putative Signal Peptide of Protease-Activated Receptor 1 Confers Potent Protection from Myocardial Ischemia-Reperfusion Injury", Journal of Pharmacology and Experimental Therapeutics, American Society for Pharmacology and Experimental Therapeutics, US, vol. 332, No. 3, Dec. 15, 2009, pp. 898-905.
Strande Jennifer L et al: "Parstatin: a cryptic peptide involved in cardioprotection after ischaemia and reperfusion injury", Jul. 2009, Cardiouascular Research, vol. 83, Nr. 2, pp. 325-334.
Zania P et al: "Parstatin, the Cleaved Peptide on Proteinase-Activated Receptor 1 Activation, Is a Potent Inhibitor of Angiogenesis", Feb. 1, 2009, Journal of Pharmacology and Experimental Therapeutics, pp. 378-389.
International Search Report & Written Opinion from PCT/IB2010/002142, dated Mar. 23, 2011.
Diamantopoulos, et al.: Parstatin Prevents Renal Injury following Ischemia/Reperfusion and Radiocontrast Administration; Am J Nephroi., 2012, vol. 36, pp. 278-286.
Claytor, et al.: The cleaved peptide of PAR1 is a more potent stimulant of platelet—endothelial cell adhesion than is thrombin; J Vasc Surg., 2003, vol. 37, pp. 440-445.
Furman, et al.: The cleaved peptide of the thrombin receptor is a strong platelet agonist; Proc Natl Acad Sci USA, 1998, vol. 95, pp. 3082-3087.
Huang, et al.: Parstatin Suppresses Ocular Neovascularization and Inflammation; Invest Ophthalmol Vis Sci, 2010, vol. 51, pp. 5825-5832.
Ramachandran, et al.: Release of the thrombin receptor (PAR-1) N-terminus from the surface of human platelets activated by thrombin; Thromb Haemost, 1997, vol. 78, pp. 1119-1124.
Zampatis, et al.: The protease-activated receptor 1 possesses a functional and cleavable signal peptide which is necessary for receptor expression; FEBS Let., 2012, vol. 586, pp. 2351-2359.

*Primary Examiner* — Christina Bradley
(74) *Attorney, Agent, or Firm* — Lathrop & Gage LLP; Brian C. Trinque

(57) ABSTRACT

The present invention relates to parstatin peptides, compositions comprising parstatin peptides and their use in the treatment of various disorders, including angiogenesis-related diseases, ocular neovascularization and related disease states, ischemia-reperfusion injury and myocardial-related disease states, and renal disorders.

5 Claims, 35 Drawing Sheets

A

B

A

B

A

B

C

A

B

A

B

C

D

E

A

B

C

A

B

C

A

B

C

D

A

B

A

B

A

B

A

B

A

B

SEQUENCE LISTING

<160> NUMBER OF SEQ ID NOS: 15

<210> SEQ ID NO 1
<211> LENGTH: 41
<212> TYPE: PRT
<213> ORGANISM: Homo sapiens

```
<400> SEQUENCE: 1

Met Gly Pro Arg Arg Leu Leu Leu Val Ala Ala Cys Phe Ser Leu Cys
1               5                   10                  15

Gly Pro Leu Leu Ser Ala Arg Thr Arg Ala Arg Arg Pro Glu Ser Lys
            20                  25                  30

Ala Thr Asn Ala Thr Leu Asp Pro Arg
        35                  40

<210> SEQ ID NO 2
<211> LENGTH: 41
<212> TYPE: PRT
<213> ORGANISM: Mus musculus

<400> SEQUENCE: 2

Met Gly Pro Arg Arg Leu Leu Ile Val Ala Leu Gly Leu Ser Leu Cys
1               5                   10                  15

Gly Pro Leu Leu Ser Ser Arg Val Pro Met Ser Gln Pro Glu Ser Glu
            20                  25                  30

Arg Thr Asp Ala Thr Val Asn Pro Arg
        35                  40

<210> SEQ ID NO 3
<211> LENGTH: 41
<212> TYPE: PRT
<213> ORGANISM: Artificial Sequence
<220> FEATURE:
<223> OTHER INFORMATION: Scrambled synthetic peptide

<400> SEQUENCE: 3

Leu Arg Thr Asn Ala Ser Leu Leu Val Pro Phe Leu Thr Ala Arg Ala
1               5                   10                  15

Lys Ser Ser Gly Thr Arg Glu Ala Ala Asp Pro Pro Arg Leu Met Cys
            20                  25                  30

Leu Arg Pro Leu Ala Arg Arg Cys Gly
        35                  40

<210> SEQ ID NO 4
<211> LENGTH: 18
<212> TYPE: PRT
<213> ORGANISM: Homo sapiens

<400> SEQUENCE: 4

Thr Arg Ala Arg Arg Pro Glu Ser Lys Ala Thr Asn Ala Thr Leu Asp
1               5                   10                  15

Pro Arg

<210> SEQ ID NO 5
<211> LENGTH: 41
<212> TYPE: PRT
<213> ORGANISM: Macaca mulatta

<400> SEQUENCE: 5

Met Gly Pro Arg Arg Leu Leu Leu Val Ala Ala Cys Leu Cys Leu Cys
1               5                   10                  15

Gly Pro Leu Leu Ser Ala Arg Thr Arg Ala Arg Arg Pro Ala Ser Lys
            20                  25                  30

Ala Thr Asn Ala Thr Leu Asp Pro Arg
        35                  40
```

```
<210> SEQ ID NO 6
<211> LENGTH: 41
<212> TYPE: PRT
<213> ORGANISM: Rattus norvegicus

<400> SEQUENCE: 6

Met Gly Pro Arg Arg Leu Leu Leu Val Ala Val Gly Leu Ser Leu Cys
1               5                   10                  15

Gly Pro Leu Leu Ser Ser Arg Val Pro Met Arg Gln Pro Glu Ser Glu
            20                  25                  30

Arg Met Tyr Ala Thr Pro Tyr Ala Thr
            35                  40

<210> SEQ ID NO 7
<211> LENGTH: 41
<212> TYPE: PRT
<213> ORGANISM: Cricetulus longicaudatus

<400> SEQUENCE: 7

Met Gly Pro Gln Arg Leu Leu Leu Val Ala Ala Gly Leu Ser Leu Cys
1               5                   10                  15

Gly Pro Leu Leu Ser Ser Arg Val Pro Val Arg Gln Pro Glu Ser Glu
            20                  25                  30

Met Thr Asp Ala Thr Val Asn Pro Arg
            35                  40

<210> SEQ ID NO 8
<211> LENGTH: 41
<212> TYPE: PRT
<213> ORGANISM: Bos Taurus

<400> SEQUENCE: 8

Met Gly Pro Arg Trp Leu Leu Leu Trp Ala Ala Gly Leu Gly Leu Cys
1               5                   10                  15

Ser Pro Leu Val Ser Ala Arg Thr Arg Gly Pro Arg Pro Gly Thr Asp
            20                  25                  30

Pro Thr Asn Gly Thr Leu Gly Pro Arg
            35                  40

<210> SEQ ID NO 9
<211> LENGTH: 26
<212> TYPE: PRT
<213> ORGANISM: Homo sapiens

<400> SEQUENCE: 9

Met Gly Pro Arg Arg Leu Leu Leu Val Ala Ala Cys Phe Ser Leu Cys
1               5                   10                  15

Gly Pro Leu Leu Ser Ala Arg Thr Arg Ala
            20                  25

<210> SEQ ID NO 10
<211> LENGTH: 41
<212> TYPE: PRT
<213> ORGANISM: Artificial Sequence
<220> FEATURE:
<223> OTHER INFORMATION: Scrambled synthetic peptide

<400> SEQUENCE: 10

Met Gly Pro Arg Arg Leu Leu Leu Val Ala Ala Cys Phe Ser Leu Cys
1               5                   10                  15

Gly Pro Leu Leu Ser Ala Arg Ala Leu Thr Arg Ser Ala Pro Thr Pro
            20                  25                  30
```

```
Arg Asp Arg Ala Asn Lys Glu Thr Arg
        35                  40

<210> SEQ ID NO 11
<211> LENGTH: 41
<212> TYPE: PRT
<213> ORGANISM: Homo sapiens
<220> FEATURE:
<221> NAME/KEY: MISC_FEATURFE
<222> LOCATION: (1)..(1)
<223> OTHER INFORMATION: Fluorescein isothiocyanate, FTTC, is linked to
      the N-terminal methionine via aminohexanoic acid (Ahx)

<400> SEQUENCE: 11

Met Gly Pro Arg Arg Leu Leu Leu Val Ala Ala Cys Phe Ser Leu Cys
1               5                   10                  15

Gly Pro Leu Leu Ser Ala Arg Thr Arg Ala Arg Arg Pro Glu Ser Lys
            20                  25                  30

Ala Thr Asn Ala Thr Leu Asp Pro Arg
        35                  40

<210> SEQ ID NO 12
<211> LENGTH: 19
<212> TYPE: PRT
<213> ORGANISM: Homo sapiens
<220> FEATURE:
<221> NAME/KEY: MISC FEATURE
<222> LOCATION: (19)..(19)
<223> OTHER INFORMATION: Fluorescein isothiocyanate, FITC, is linked to
      the C-terminal lysine

<400> SEQUENCE: 12

Thr Arg Ala Arg Arg Pro Glu Ser Lys Ala Thr Asn Ala Thr Leu Asp
1               5                   10                  15

Pro Arg Lys

<210> SEQ ID NO 13
<211> LENGTH: 41
<212> TYPE: PRT
<213> ORGANISM: Artificial Sequence
<220> FEATURE:
<223> OTHER INFORMATION: Scrambled synthetic peptide
<220> FEATURE:
<221> NAME/KEY: MISC_FEATURE
<222> LOCATION: (1)..(1)
<223> OTHER INFORMATION: Fluorescein isothiocyanate, FITC, is linked to
      the N-terminal methionine via aminohexanoic acid (Ahx)

<400> SEQUENCE: 13

Met Gly Pro Arg Arg Leu Leu Leu Val Ala Ala Cys Phe Ser Leu Cys
1               5                   10                  15

Gly Pro Leu Leu Ser Ala Arg Ala Leu Thr Arg Ser Ala Pro Thr Pro
            20                  25                  30

Arg Asp Arg Ala Asn Lys Glu Thr Arg
        35                  40

<210> SEQ ID NO 14
<211> LENGTH: 23
<212> TYPE: PRT
<213> ORGANISM: Homo sapiens

<400> SEQUENCE: 14

Met Gly Pro Arg Arg Leu Leu Leu Val Ala Ala Cys Phe Ser Leu Cys
1               5                   10                  15
```

```
Gly Pro Leu Leu Ser Ala Arg
            20

<210> SEQ ID NO 15
<211> LENGTH: 6
<212> TYPE: PRT
<213> ORGANISM: Artificial Sequence
<220> FEATURE:
<223> OTHER INFORMATION: Sythentic recognition sequence peptide

<400> SEQUENCE: 15

Ser Phe Leu Leu Arg Asn
1               5
```

PARSTATIN PEPTIDES

RELATED APPLICATIONS

The present application is a National Stage entry of the PCT Application No. PCT/IB2010/002142 filed Aug. 5, 2010, which is a continuation of U.S. Utility patent application Ser. No. 12/572,018, filed Oct. 1, 2009, which claims the benefit of U.S. Provisional Patent Application No. 61/247,611, filed Oct. 1, 2009, and PCT Application No. PCT/IB2010/002142 is a continuation of U.S. Utility patent application Ser. No. 12/645,991, filed Dec. 23, 2009. The entire contents of each of the above documents are incorporated herein by reference.

FIELD OF THE INVENTION

The present invention relates to parstatin peptides, compositions comprising parstatin peptides and their use in the treatment of various disorders, including angiogenesis-related diseases, ocular neovascularisation and related disease states, ischemia-reperfusion injury, myocardial-related disease states and renal disorders.

BACKGROUND OF THE INVENTION

A. Angiogenesis and Neovascular Ocular Diseases
A1. Angiogenesis and Angiogenesis-Related Diseases Angiogenesis is the generation of new blood vessels in a tissue or organ (Carmeliet, 2005, Nature, 438: 932-936). Under normal physiological conditions, humans and animals undergo angiogenesis only in very specific and restricted situations. For example, angiogenesis is normally observed in wound healing, fetal and embryonic development, and formation of the corpus luteum, endometrium and placenta.

Angiogenesis is controlled through a highly regulated system of angiogenic stimulators and inhibitors (Yancopoulos et al., 2000, Nature, 407: 242-248). Angiogenesis is turned on by specific angiogenic molecules such as basic fibroblast growth factor (bFGF), vascular endothelial growth factor (VEGF), angiogenin, transforming growth factor, tumor necrosis factor-alpha (TNF-alpha) and platelet derived growth factor (PDGF). On the other hand, angiogenesis can be suppressed by inhibitory molecules such as interferon-α, thrombospondin-1, angiostatin, and endostatin. It is the balance of these naturally occurring stimulators and inhibitors that controls the normally quiescent capillary vasculature. When this balance is upset, as in certain disease states, capillary endothelial cells are induced to proliferate, migrate and ultimately differentiate.

The control of angiogenesis has been found to be altered in certain disease states and, in many cases, the underlying pathology associated with the diseases is related to uncontrolled angiogenesis. Both controlled and uncontrolled angiogenesis are thought to proceed in a similar manner. Endothelial cells and pericytes, surrounded by a basement membrane, form capillary blood vessels. Angiogenesis begins with the local dissolution of the basement membrane by enzymes released by endothelial cells and leukocytes. Endothelial cells, lining the lumen of blood vessels, then protrude through the basement membrane. Angiogenic stimuli promote endothelial cell migration through the eroded basement membrane. The migrating cells form a "sprout" off the parent blood vessel where the endothelial cells undergo mitosis and proliferate. The endothelial sprouts merge with each other to form capillary loops, creating a new blood vessel.

Persistent, upregulated angiogenesis occurs in many disease states, including tumor growth metastases. The diverse pathological diseases states in which upregulated angiogenesis is present have been grouped together as angiogenic-diseases, angiogenesis-associated or angiogenesis-related diseases.

One example of diseases dependent on angiogenesis is ocular neovascular diseases (Gariano and Gardner, 2005, Nature, 438: 960-966). These diseases are characterized by invasion of new blood vessels into the structure of the eye, such as the retina or cornea. They are the most common cause of blindness and comprise approximately twenty eye diseases. In age-related macular degeneration, the associated visual problems are caused by an ingrowth of choroidal capillaries through defects in Bruch's membrane, with proliferation of fibrovascular tissue beneath the retinal pigment epithelium. Angiogenic damage is also associated with diabetic retinopathy, retinopathy of prematurity, corneal graft rejection, neovascular glaucoma, and retrolental fibroplasias. Other diseases associated with corneal neovascularization include, but are not limited to, epidemic keratoconjunctivitis, Vitamin A deficiency, contact lens overwear, atopic keratitis, superior limbic keratitis, and pterygium keratitis sicca.

Another example of angiogenesis-related disease is rheumatoid arthritis (Bainbridge et al., 2006, Curr Pharm Des, 12: 2631-2644). The blood vessels in the synovial lining of the joints undergo angiogenesis. In addition to forming new vascular networks, the endothelial cells release factors and reactive oxygen species that lead to pannus growth and cartilage destruction. Angiogenesis may also play a role in osteoarthritis. The activation of the chondrocytes by angiogenic-related factors contributes to the destruction of the joint. At a later stage, the angiogenic factors promote new bone growth. Therapeutic intervention that prevents the cartilage destruction could halt the progress of the diseases and provide relief for persons suffering from arthritis.

Chronic inflammation may also involve pathological angiogenesis. Such disease as ulcerative colitis and Crohn's disease show histological changes with the ingrowth of new blood vessels into inflamed tissue. Bartonellosis, a bacterial infection found in South America, in a chronic stage is characterized by proliferation of vascular endothelial cells.

Several lines of direct evidence now suggest that angiogenesis is essential for the growth and persistence of solid tumors and their metastases. To stimulate angiogenesis, tumors upregulate the production of a variety of angiogenic factors, including the bFGF and VEGF (Yancopoulos et al., 2000, Nature, 407: 242-248). However, many malignant tumors also generate inhibitors of angiogenesis, including angiostatin, endostastin, and thrombospondin (Nyberg et al., 2005, Cancer Res, 65: 3967-3979). It is postulated that the angiogenic phenotype is the result of a net balance between these positive and negative regulators of neovascularization. Several other endogenous inhibitors of angiogenesis have been identified, although not all are associated with the presence of a tumor. These include, platelet factor 4, interferon-alpha, interferon-inducible protein 10, which is induced by interleukin-12 and/or interferon-gamma, the 16 kDa N-terminal fragment of prolactin, tumstatin, arresten, canesten, anastellin, vasostatin, and vasohibin.

A2. Ocular Neovascularization and Related Disease States

Pathologic or aberrant angiogenesis/neovascularization, aberrant remodeling, fibrosis and scarring and inflammation occur in association with retinal and ocular ischemic diseases such as age-related macular degeneration (AMD), diabetic retinopathy (DR) and in retinopathy of prematurity (ROP) and other developmental disorders (Eichler et al., 2006, Curr Pharm Des, 12: 2645-60) as well as being a result of infections and mechanical or chemical injury to the cornea and the eye in general (Ciulla et al., 2001, Curr Opin Opthalmol, 12: 442-9; Dart et al., 2003, Eye, 17: 886-92).

Diabetic retinopathy is a leading cause of blindness in adults of working age. The leading cause of vision loss for Americans under the age of 65 is diabetes; 16 million individuals in the United States are diabetic and 40,000 per year suffer from ocular complications of the disease, often a result of retinal neovascularization. DR, therefore, is a retinal microvascular disease that is manifested as a cascade of stages with increasing levels of severity and a worsening prognosis for vision. DR is broadly classified into 2 major clinical stages: nonproliferative diabetic retinopathy and proliferative diabetic retinopathy (PDR), where the term "proliferative" refers to the presence of preretinal neovascularization (PNV) emanating from the retina into the vitreous. Ocular neovascularization occurs in areas where capillary occlusions have developed, creating areas of ischemic retina and acting as a stimulus for neovascular proliferation that originate from pre-existing retinal venules at the optic disk and/or elsewhere in the retina posterior to the equator of the eye. Vitreous haemorrhage and tractional retinal detachment from PDR can cause severe vision loss (Boulton et al., 1997, Br J Ophthalmol, 81: 228-223). Diabetic macular edema (DME) is a further common cause of blindness (Levin, 2001, J Glaucoma 10:19-21; Stefansson et al., 1992, Am J. Ophthalmol. 113:36-38). A clinical hallmark of PDR includes the increased vascular permeability, leading to DME, and endothelial cell proliferation.

Age-related macular degeneration is a leading cause of vision loss in people over 65 years old. For example, AMD affects 12-15 million American over the age of 65 and causes vision loss in 10-15% of them. In contrast to ROP and PDR, in which neovascularization emanates from the retinal vasculature and extends into the vitreous cavity, AMD is associated with neovascularization originating from the choroidal vasculature and extending into the subretinal space. Choroidal neovascularization (CNV) causes severe vision loss in AMD patients because it occurs in the macula, the area of retina responsible for central vision (Kitaoka et al., 1997, Curr Eye Res, 16:396-399).

Multiple theories exist but, the exact etiology and pathogenesis of AMD are still not well understood. Aging is associated with cumulative oxidative injury, thickening of Bruch's membrane and drusen formation. Oxidative stress results in injury to retinal pigment epithelial cells (RPE) and, in some cases, the choriocapillaris (Zarbin, 2004, Arch Opthalmol, 122: 598-614; Gorin et al., 1999, Mol Vis, 5: 29). Injury to RPE likely elicits a chronic inflammatory response within Bruchs membrane and the choroid (Johnson et al., 2000, Exp Eye Res, 70: 441-9). This injury and inflammation fosters and potentiates retinal damage by stimulating CNV and atrophy (Zarbin, 2004, Arch Opthalmol, 122: 598-614; Witmer et al., 2003, Prog Retin Eye Res, 22: 1-29). CNV results in defective and leaky blood vessels (BV) that are likely to be recognized as a wound (Kent and Sheridan, 2003, Mol Vis, 9: 747-55).

Retinopathy of prematurity (ROP) occurs most prominently in premature neonates. In various cases, the retina becomes completely vascularized at full term/near birth. In the premature baby, the retina remains incompletely vascularized at the time of birth. Rather than continuing in a normal fashion, vasculogenesis in the premature neonatal retina becomes disrupted. Abnormal new proliferating vessels develop at the juncture of vascularized and avascular retina. These abnormal new vessels grow from the retina into the vitreous, resulting in haemorrhage and tractional detachment of the retina (Neely et al., 1998, Am. J. Pathol, 153:665-670). It is estimated that visual impairment from this disease affects 3400 infants and causes blindness in 650 infants annually in the United States. Angiogenesis is the hallmark of this debilitating condition.

Others retinal diseases associated with retinal neovascularization include sickle cell retinopathy, retinal vein occlusion, certain inflammatory diseases of the eye, ocular tumorigenesis, Eale's disease, myopic choriodal neovascularization, and polypoidal choriodal vasculopathy. These, however, account for a much smaller proportion of visual loss caused by ocular neovascularization (Neely et al., 1998, American J. of Path. 153:665-670).

Corneal neovascularization, the abnormal formation of blood vessels in the cornea, is a common and serious complication of many corneal diseases and is a major cause of blindness that affects millions of people (Adamis, 2005, Retina, 25: 111-118). The condition is associated with severe visual impairment and is a high risk factor for graft rejection after allograft corneal transplantation. In addition, corneal neovascularization and subsequent opacification remain the most frequent causes of blindness after severe alkali burn trauma. To date, there are no pharmacological or surgical treatment options for the inhibition of corneal neovascularization that have been proven to be both safe and effective. Despite the routine use of topical steroids, the inflammatory response can lead to oedema, lipid deposition and corneal scarring that may not only significantly alter visual acuity, but also worsen the prognosis of subsequent penetrating keratoplasty. In addition, longer-term use of these drugs can lead to various adverse side effects such as cataracts, glaucoma, infection, and delay corneal epithelial healing.

VEGF plays a dominant role in iris neovascularization and neovascular retinopathies. While reports clearly show a correlation between intraocular VEGF levels and ischemic retinopathic ocular neovascularization, FGF likely plays an essential role. Basic FGF is known to be present in the normal adult retina, even though detectable levels are not consistently correlated with neovascularization. This may be largely due to the fact that FGF binds very tightly to charged components of the extracellular matrix and may not be readily available in a freely diffusible form that would be detected by standard assays of intraocular fluids. Furthermore, overexpression of bFGF in the eye does not stimulate neovascularization because it is sequestered (Osaki et al., 1998, Am J Pathol, 153: 757-765), but bFGF does contribute to choriodal neovascularization when there is tissue disruption from the disease process itself or attempts at treatment (Yamada et al., 2000, J Cell Physiol, 185:135-142).

Viable and approved current treatments for diseases related to ocular neovascularization are limited. The approved treatments for AMD are photodynamic therapy with VISUDYNE® (QLT/Novartis) and intravitreal injection of Macugen® (pegaptanib) (Eyetech/Pfizer) or Lucentis® (ranibizumab) (Genentech). Laser photocoagulation alone or photodynamic therapy with VISUDYNE® are therapies that involve laser-induced occlusion of the affected vasculature, which can result in localized damage to the retina. Macugen® (Eyetech/Pfizer) is an anti-VEGF aptamer that binds to VEGF165 preventing ligand-receptor interaction and is labeled for intravitreal injections every 4 weeks. Lucentis® (Genentech) is a humanized anti-VEGF antibody fragment that also binds directly to all isoforms of human VEGF and is labeled for intravitreal injections every 6 weeks. A variety of other pharmacologic therapies are undergoing clinical evaluation for AMD, such as RETAANE® 15 mg (anecortave acetate suspension, Alcon Research, Ltd.), Envision (squalamine, Genera), the VEGF R1R2 Trap, (Regeneron), Cand5 (anti-VEGF siRNA, Acuity), Sirna-027 (anti-VEGFR1 siRNA, SIRNA/Allergan), a topical receptor tyrosine kinase antagonist (TargeGen), sirolimus (rapamycin, MacuSight), etc.

Grid and pan retinal laser photocoagulation are the only proven options currently available for patients with diabetic macular edema or PDR, respectively. Multifocal laser photocoagulation may reduce retinal ischemia and inhibit angiogenesis by destroying healthy tissue and thus decreasing the total metabolic demand of the retina. Laser photocoagulation may also modulate the expression and production of various cytokines and trophic factors. Unfortunately, laser photocoagulation is a cytodestructive procedure and the visual field of the treated eye is irreversibly compromised. Surgical interventions, such as vitrectomy and removal of preretinal membranes, are widely used with or without laser treatment. Similar to the AMD trials, various pharmacologic agents are in clinical trials for DME, such as ARXXANT™ (ruboxystaurin mesylate, Lilly), RETISERT™ (fluocinolone acetonide, Bausch & Lomb), Posurdex (fluocinolone acetonide erodible implant, Occulex/Allergan), I-vation (nonerodible Dexamethasone implant, Occulex), Medidur (fluocinolone acetonide erodible implant, Alimera), etc. Intravitreal or periocular injection of triamcinolone acetonide, a corticosteroid (Kenalog®, Schering-Plough), and intravitreal Avastin® (anti-VEGF Mab (bevacizumab), Genentech) are also being used "off-label" for the treatment of both macular edema and wet AMD.

Anti-VEGF therapies represent a recent, significant advance in the treatment of exudative AMD. However, the phase III VISION Trial with PEGAPTANIB, a high affinity aptamer which selectively inhibits the 165 isoform of VEGF-A, demonstrated that the average patient continues to lose vision and only a small percent gained vision (Gragoudas et al., 2004, N Engl J Med, 351: 2805-16). Inhibition of all isoforms of VEGF-A (pan-VEGF inhibition) with the antibody fragment RANIBIZUMAB yielded much more impressive results (Brown et al., 2006, N Eng J Med, 355:1432-44; Rosenfeld et al., 2006, N Eng J Med 355:1419-31). The 2 year MARINA trial and the 1 year ANCHOR trial demonstrated that approximately 40% of patients achieve some visual gain. Although these results represent a major advance in our ability to treat exudative AMD, they also demonstrate that 60% of patients do not have visual improvement. Furthermore, these patients had to meet strictly defined inclusion and exclusion criteria. The results in a larger patient population may be less robust. In addition, adverse effects on neurons and vessels have been observed in primates after a single administration of the humanized anti-VEGF antibody (Bevacizumab) (Peters et al., 2007, Am J Ophthalmol, 91: 827-831) and sporadic case reports of complications of anti-VEGF therapy related to regression of blood vessels, increased risk for stroke and myocardial infarction, and local side effects due to the intravitreal application mode have appeared (Fraunfelder et al., 2005, Drugs Today, 41: 703-709; Tobin et al., 2006, Insight, 31: 11-14; Rosenfeld et al., 2006, Ophthalmol Clin NA, 19: 361-372; Baffert et al., 2006, Am J Physiol Heart Circ Physiol, 290: H547-H559; Hurwitz et al., 2004, Clin Colorectal Cancer, 4(suppl): 2: S62-S68). The limited efficacy and potential adverse effects of currently implemented therapies emphasize the need for alternative therapeutic strategies.

B. Ischemia-Reperfusion Injury and Myocardial-Related Disease States

Ischemia-reperfusion injury (I/R injury) refers to an event in which the blood supply to a tissue is obstructed, such as myocardial infarction. Whenever there is a transient decrease or interruption of blood flow the net injury is the sum of two components: the "direct" injury occurring during the ischemic interval and the "indirect" or reperfusion injury which follows. Reperfusion injury can be defined as the damage that occurs to an organ that is caused by the resumption of blood flow after an episode of ischemia. This damage is distinct from the injury resulting from the ischemia per se. One hallmark of reperfusion injury is that it may be attenuated by interventions initiated before or during the reperfusion. Reperfusion injury results from several complex and interdependent mechanisms that involve the production of reactive oxygen species, endothelial cell dysfunction, microvascular injury, alterations in intracellular $Ca^{2+}$ handling, changes in tissue metabolism, and activation of neutrophils, platelets, cytokines and the complement system. All of the deleterious consequences associated with reperfusion constitute a spectrum of reperfusion-associated pathologies that are collectively called reperfusion injury. Reperfusion injury can extend not only acutely, but also over several days following the tissue attack.

During blood vessel obstruction, the endothelial tissue lining the affected blood vessels becomes "sticky" and begins to attract circulating white blood cells (Tohoku, 2008, J Exp Med, 215: 257-266). The white cells bound to the endothelium eventually migrate into the cardiac tissue causing significant tissue destruction. Although acute myocardial infarction is not directly caused by inflammation, much of the underlying pathology and the damage that occurs after an acute ischemia-reperfusion injury is caused by acute inflammatory responses during reperfusion, the restoration of blood flow to the affected myocardium. White blood cells present to the area by the newly returning blood release a host of inflammatory factors such as interleukins as well as free radicals in response to tissue damage. The restored blood flow reintroduces oxygen within cells that damages cellular proteins, DNA and the plasma membranes. Damage of the cell membrane may in turn causes release of more free radicals signaling apoptosis. Leukocytes may also build up in small capillaries, obstructing them and leading to more ischemia.

Cardiovascular disease is the leading cause of death in the western world. Coronary artery disease can lead to prolonged or irreversible episodes of cardiac ischemia that result in myocardial infarction (MI) which is associated with a high rate of mortality. The reduced blood flow in heart diseases is typically caused by blockage of a vessel by an embolus (blood clot); the blockage of a vessel due to atherosclerosis; the breakage of a blood vessel (a bleeding stroke); the blockage of a blood vessel due to vasoconstriction such as occurs during vasospasms and possibly, during transient ischemic attacks (TIA) and following subarachnoid haemorrhage. Conditions in which ischemia occurs further include myocardial infarction; trauma; and during cardiac and thoracic surgery and neurosurgery (blood flow needs to be reduced or stopped to achieve the aims of surgery). Procedures that can cause myocardial ischemia include coronary thrombolysis, coronary angioplasty (with or without stent placement), and coronary artery bypass grafts. During myocardial infarct, stoppage of the heart or damage occurs which reduces the flow of blood to myocardium, and ischemia results. Cardiac tissue itself is also subjected to ischemic damage. During various surgeries, reduction of blood flow, clots or air bubbles generated can lead to significant ischemic damage of the myocardium.

During an ischemic event, there is a gradation of injury that arises from the ischemic site. Cells at the site of blood flow restriction, undergo necrosis and form the core of a lesion. A penumbra is formed around the core where the injury is not immediately fatal but progresses slowly toward cell death. This progression to cell death may be reversed upon reestablishment of blood flow within a short time of the ischemic event. Timely reperfusion to reduce the duration of ischemia is the definitive treatment to prevent cellular injury and necrosis in an ischemic myocardium. Typically reperfusion, after a short episode of myocardial ischemia (up to 15 min), is followed by the rapid restoration of cellular metabolism and function. Even with the successful treatment of occluded vessels, a significant risk of additional tissue injury after reperfusion may still occur. If the ischemic episode has been of sufficient severity and/or duration to cause significant changes in the metabolism and the structural integrity of heart muscle, reperfusion may paradoxically result in a worsening of heart function, out of proportion to the amount of dysfunction expected simply as a result of the duration of blocked flow. Although the beneficial effects of early reperfusion of ischemic myocardium with thrombolytic therapy, PTCA, or CABG are now well established, an increasing body of evidence indicates that reperfusion also induces an additional injury to ischemic heart muscle, such as the extension of myocardial necrosis, i.e., extended infarct size and impaired contractile function and metabolism. Hearts undergoing reperfusion after transplantation also undergo similar reperfusion injury events.

Despite efforts towards the development of new therapies for the treatment of diseases and conditions such as heart failure and cardiac ischemia/reperfusion injury, this remains an unmet need for additional or alternative agents to treat or prevent the onset or severity of this condition (Ferdinandy et al., 2007, Pharmacol Rev, 59: 418-458). Current therapies include the use of vasodilators, anti-thrombotics/thrombolytics, beta-blockers and coronary artery bypass graft are used pre and post myocardial ischemia to maintain/restore coronary blood flow and limit oxygen demand.

C. Acute Renal Failure and Related Disease States

Acute renal failure (ARF), also known as acute renal injury (ARI) or acute kidney injury (AKI), is a clinical syndrome characterized by rapid deterioration of renal function that occurs within days. ARF is estimated to occur in at least 5% of all hospitalized patients, and in 30-50% of those admitted to the intensive care unit. ARF secondary to a renal tubular cell injury, including an ischemic injury or a nephrotoxic injury remains a common and potentially devastating problem in clinical medicine and nephrology, with a persistently high rate of mortality and morbidity despite significant advances in supportive care (Chatterjee and Thiemermann, 2003, Expert Opin Emerg Drugs, 8: 389-435).

Pioneering studies over several decades have illuminated the roles of persistent vasoconstriction, tubular obstruction, cellular structural and metabolic alterations, and the inflammatory response in the pathogenesis of ARF. While these studies have suggested possible therapeutic approaches in animal models, translational research efforts in humans have yielded disappointing results. The reasons for this may include the multifaceted response of the kidney to ischemic injury and nephrotoxins, and a paucity of early biomarkers for ARF with a resultant delay in initiating therapy.

The most common cause of ARF—acute tubular necrosis—is most frequently observed in the setting of renal ischemia reperfusion injury, post-renal transplant, sepsis, post-myocardial infarct, in the elderly with diminished fluid intake, and as a consequence of exposure to radiocontrast agents and a wide range of toxins, including cis-platinum, aminoglycosides, amphotericin B, and acyclovir. The notion that only severe renal failure impacts on long-term morbidity is dispelled by the fact that even modest degrees of renal insufficiency significantly increase the risk of death for critically ill patients Renal ischemia-reperfusion injury refers to an event in which the blood supply to kidneys is obstructed, such as renal occlusion (Chatterjee, 2007, Naunyn-Schmiedeberg's Arch Pharmaco J, 376: 1-43). Reperfusion injury can be defined as the damage that occurs to kidney that is caused by the resumption of blood flow after an episode of ischemia. This damage is distinct from the injury resulting from the ischemia per se. Renal ischemia-reperfusion injury results from several complex and interdependent mechanisms that involve the production of reactive oxygen species, endothelial cell dysfunction, microvascular injury, alterations in intracellular $Ca^{2+}$ handling, changes in tissue metabolism, and activation of neutrophils, platelets, cytokines and the complement system. All of the deleterious consequences associated with reperfusion constitute a spectrum of reperfusion-associated pathologies that are collectively called reperfusion injury. Reperfusion injury can extend not only acutely, but also over several days following the tissue attack.

Due to obstruction, the endothelial tissue lining the affected blood vessels becomes "sticky" and begins to attract circulating white blood cells (Tohoku, 2008, J Exp Med, 215: 257-266). The white cells bind to the endothelium and eventually migrate into the kidneys causing significant tissue destruction. Although acute renal occlusion is not directly caused by inflammation, much of the underlying pathology and the damage that occurs after an acute ischemia-reperfusion injury is caused by acute inflammatory responses during reperfusion, the restoration of blood flow to the kidney. White blood cells present to the area by the newly returning blood release a host of inflammatory factors such as interleukins as well as free radicals in response to tissue damage. The restored blood flow reintroduces oxygen within cells that damages cellular proteins, DNA, and the plasma membranes. Damage of the cell membrane may in turn promotes release of more free radicals signaling apoptosis. Leukocytes may also built up in small capillaries obstructing them and leading to more ischemia.

During an ischemic event, there is a gradation of injury that arises from the ischemic site. Cells at the site of blood flow restriction, undergo necrosis and form the core of a lesion. A penumbra is formed around the core where the injury is not immediately fatal but progresses slowly toward cell death. This progression to cell death may be reversed upon reestablishment of blood flow within a short time of the ischemic event. Timely reperfusion to reduce the duration of ischemia is the definitive treatment to prevent cellular injury and necrosis in an ischemic kidney. Typically reperfusion, after a short episode of renal ischemia (up to 30 min), is followed by the rapid restoration of cellular metabolism and function. Even with the successful treatment of occluded vessels, a significant risk of additional tissue injury after reperfusion may still occur. If the ischemic episode has been of sufficient severity and/or duration to cause significant changes in the metabolism and the structural integrity of renal tissue, reperfusion may paradoxically result in a worsening of renal function, out of proportion to the amount of dysfunction expected-simply as a result of the duration of blocked flow.

Without being bound by theory acute kidney injury may be the result of renal ischemia-reperfusion injury (ischemia-reperfusion) that occurs, for example, in patients undergoing major surgery such as major cardiac surgery (Padanilam, 2003, Am J Physiol, 284: F608-F627). Renal ischemia, whether caused by shock or during surgery or transplantation, is a major cause of acute kidney injury. Although reperfusion is essential for the survival of ischemic tissue, there is strong evidence that reperfusion itself caused additional cellular injury and together ischemia-reperfusion of the kidney leads to ischemic ARF. Renal ischemia-reperfusion injury is caused by multiple insults involving tubular cell apoptosis, oxygen free radical formation, mitochondrial dysfunction, inflammatory cytokine generation and neutrophils sequestration.

Contrast-induced nephropathy (CIN) is generally recognized as acute renal failure occurring within 48 hours of exposure to intravascular contrast material, and where other causes of renal failure are not attributable. Its presence is generally determined when an increase in serum creatinine levels is exhibited in a subject who has been exposed to intravascular contrast material. CIN is an important problem in clinical practice and contrast-induced morbidity has become a significant cause of hospital morbidity and mortality with the increasing use of iodinated contrast media in diagnostic imaging and interventional procedures such as angiography. In 2003, over 80 million doses of iodinated intravascular contrast media were administrated, corresponding to approximately 8 million liters according to Katzberg et al. (2006, Kidney International, 69: S3-S7). With the increasing use of contrast media in diagnostic and interventional procedures, CIN has become the third leading cause of hospital-acquired acute renal failure, accounting for 10 to 25% of all acute renal failure cases, despite the introduction of newer and safer contrast media, the improvement of hydration protocols, and the introduction of additional preventive strategies.

There are different classes of contrast agents in use such as:
  High osmolar agents, such as Iothalamate and Diatrizoate. The osmolality of these agents is about 5 times greater than the osmolality of blood.
  Low osmolar agents, such as Iohexyl, Ioversol, Iopamidol, Iopromide, Iomeprol and Ioxaglate. The osmolality of these agents is about 2-3 times greater than the osmolality of blood.
  Iso-osmolar agents, such as Iotrolan and Iodixanol. The osmolality of these agents is the same as the osmolality of blood.

The pathophysiological mechanisms that underlie the development of CIN are not fully understood (ref). Nevertheless, there are recognized risk factors that pre-dispose individuals for the development of contrast agent-induced acute renal failure and these include subject-related factors and procedure-related factors (Kagan and Sheikh-Hamad, 2010, Clinical Cardiology, 33: 62-66). It has been the subject of numerous studies addressing characteristics of the populations at risk and prophylactic strategies. Evidence-based reviews, summarizing recent literature, provides a nephrologists' perspective on contrast-induced nephropathy, focusing on: the pathophysiology of contrast-induced nephropathy; identification of populations at risk; correlation between contrast-induced nephropathy and the type of contrast agent used; and finally, measures to prevent contrast-induced nephropathy, including intravenous fluids, sodium bicarbonate, N-acetylcysteine, and hemofiltration/hemodialysis.

In addition, sepsis and septic shock remain the most important cause of ARF in critically ill patients and account for more than 50% of cases of ARF in the intensive care unit. Despite increasing ability to support vital organs and resuscitate patients, the incidence and mortality of septic ARF remain high. Its mortality varies with the severity of acute kidney injury from 21% to 57%.

Therefore, there is a great need for new, effective strategies for prevention of ARF and in particular therapies for the treatment of diseases and conditions such as I/R injury-, pharmacotherapy-, contrast- and sepsis-induced ARF. This unmet medical need for novel agents to treat, prevent or protect from the onset or severity of these conditions presents opportunities for developing blockbuster drugs.

D. Parstatin: a Protease-Activated Receptor 1-Derived Peptide

Thrombin is a serine protease, which plays a pivotal role in haemostasis. It acts as procoagulant converting fibrinogen into fibrin that anchors platelets at the site of lesion and stabilizes the clot by activating factor XIII and enhances its own generation from prothrombin by activation of factors V, VIII and XI. On the other hand, thrombin acts as an anti-coagulant by activating protein C (Di Cera, 2003).

Apart from its role in blood clotting and fibrin generation, thrombin has important roles in the initiation of angiogenesis (Tsopanoglou and Maragoudakis, 2004, Sem Thromb Hemost, 30: 63-69). Thrombin's angiogenic activity is mostly independent of its coagulant activity and is more dependent on signaling via the protease-activated receptors 1 (PAR1). This supported by the observations obtained in mouse models, wherein a lack of thrombin generation (TF−/−, FX−/−, FV−/−, FII−/−) results in severe vascular defects in embryonic development (Moser and Patterson, 2003, Arterioscler Thromb Vasc Biol, 23: 922-930). Similar phenotypes occur in models of impaired thrombin binding to its PAR receptor (PAR1−/−).

Protease-activated receptors (PARs) consists a family of G protein-coupled receptors which can be activated by proteolytic cleavage of their N-terminal extracellular domain (Ossovskaya and Bunnett, 2004, Physiol Rev, 84: 579-621). PAR1 is the first member of this family to be cloned in which the extracellular amino terminus is cleaved to expose a new amino terminus that is involved in receptor activation (Vu et al., 1991, Cell, 64: 1057-1068). Subsequently, three other members of this receptor family have been identified, designated as PAR2, PAR3 and PAR4. Proteolytic cleavage at the $R_{41}/S_{42}$ bond of human PAR1 by thrombin releases a 41 amino acid peptide and unveils a tethered peptide ligand with the recognition sequence SFLLRN (SEQ ID NO: 15). This sequence binds to conserved regions in the second extracellular loop of the cleaved receptor, resulting in the initiation of signal transduction. There is evidence that not only thrombin but also other molecules, such as plasmin, factor Xa, activated protein C, as well as matrix metalloprotease-1, might be able to activate this receptor under certain conditions and induce down-stream signals (Leger et al., 2006, Circulation, 114: 1070-1077).

Thrombin, through PAR1 signaling, interacts and stimulates a variety of vascular cells including, but is not limited to, platelets, endothelial cells, smooth muscle cells and regulates the release, expression and activation of the majority of angiogenesis mediators. For example, thrombin-induced angiogenesis in a chick chorioallontoic membrane system is associated with up-regulation of VEGF as well as angiopoietin-2 (Ang-2) (Caunt et al, 2003, J Thromb Haemost, 1: 2097-2102). Also, in endothelial cells thrombin up-regulates VEGF (Huang et al, 2001, Thromb Haemost, 86: 1094-1098), Ang-2 (Huang et al., 2002, Blood, 99: 1646-1650) and the major VEGF receptor KDR (Tsopanoglou and Maragoudakis, 1999, J Biol Chem, 274: 23969-23976), and activates metalloproteinase-2 (Zucher et al., 1995, J Biol Chem, 270: 23730-23738). It was recently shown that thrombin markedly up-regulates growth-regulated oncogene-α and this chemokine in turn mediates the thrombin-induced increase of vascular regulatory proteins (MMP-1, MMP-2), growth factors (VEGF, Ang-2), and receptors (KDR) (Gaunt et al, 2006, Cancer Res, 66: 4125-4132). In addition thrombin induces the secretion of VEGF (Mohle et al., 1997, Proc Natl Acad Sci USA, 94: 663-668) and Ang-1 (Li et al., 2001, Thromb Haemost, 85: 204-206) from platelets. Furthermore, it was demonstrated that thrombin regulates in an opposing fashion the release of VEGF and endostatin (the potent endogenous inhibitor of angiogenesis) in platelets (Ma et al., 2005, Proc Natl Acad Sci USA, 102: 216-220). Thrombin has also been shown to activate the proliferation of endothelial cells by acting directly as mitogenic factor (Olivot et al., 2001, Circ Res, 88: 681-687).

The fact that thrombin plays an important role in angiogenesis, suggests a crucial role for thrombin and its receptor, PAR1 in tumor progression and metastasis (Nierodzik and Karpatkin, 2006, Cancer Cell, 10: 355-362). Thrombin, through PAR1 signaling, contributes to a more malignant phenotype by activating platelet-tumor aggregation, tumor adhesion to subendothelial matrix, tumor growth and metastasis.

In addition, PAR1 expressed on platelets and the vascular endothelium, has been shown to play important roles in normal blood vessel biology (Coughlin, 2005, J Thromb Hemost, 3: 1800-1814) and to contribute to the pathogenesis of several cardiovascular diseases including atherosclerosis, restenosis and thrombosis (Leger et al., 2006, Circulation, 114: 1070-1077). In particular, aberrant over-expression of PAR1 has been documented in the endothelium and vascular smooth muscle cells of human atheroscrerotic arteries, including regions of intimal thickening (Nelken et al., 1992, J Clin Invest, 90: 1614-1621). Activation of PAR1 triggers mitogenic responses in smooth muscle cells and fibroblast and angiogenesis. Targeting PAR1 with a blocking antibody reduced intimal hyperplasia by approximately 50% in a catheter-induced injury model of restenosis (Takada et al., 1998, Circ Res, 82: 980-987). PAR1 deficiency also reduced restenosis in arterial injury models (Cheung et al., 1999, Arterioscler Thromb Vasc Biol, 19: 3014-3024). Recently, it has been shown that thrombin contributes to ischemia/reperfusion injury independently of its effects on platelets and fibrinogen. In addition, PAR1 inhibition has been demonstrated to protect against myocardial ischemia/reperfusion injury by recruiting cardioprotective pathways (Strande et al, 2007, Basic Res Cardiol, 102: 350-358).

Despite the wealth of information relating to the role of thrombin and PAR1 in physiology and diseases states, the information regarding the biological role of cleaved peptides upon activation of PAR1 is very limited. There are only three reports which associate the 41 amino acid cleaved peptide of the PAR1 with potential biological functions (Furman et al., 1998, Proc Natl-Acad Sci USA, 95: 3082-3087; Furman et al., 2000, Thromb Haemost, 84: 897-903; Furman et al., 2003, J Vasc Surg, 37: 440-445). The name of "parstatin" has been coined for this peptide.

The present invention seeks to provide novel peptides derived from parstatin, together with new therapeutic applications for full length parstatin peptide and various peptide fragments thereof.

SUMMARY OF THE INVENTION

A first aspect of the invention relates to an isolated peptide comprising a sequence selected from SEQ ID NO:1 (1-41), SEQ ID NO:9 (1-26) and SEQ ID NO:4 (24-41), or a variant, derivative, fragment or homologue thereof.

A second aspect of the invention relates to a composition comprising an isolated peptide as described above and a pharmaceutically acceptable diluent, excipient or carrier.

A third aspect of the invention relates to an isolated peptide or a composition as described above for use as a medicament.

A fourth aspect of the invention relates to an isolated peptide or a composition as described above for preventing, ameliorating or treating a renal disorder.

A fifth aspect of the invention relates to the use of an isolated peptide or a composition as described above in the preparation of a medicament for the treatment of a renal disorder.

A sixth aspect of the invention relates to the use of an isolated peptide or a composition as described above as a renal protective agent.

A seventh aspect of the invention relates to a method of preventing or treating a renal disorder in a subject, said method comprising administering to the subject an isolated peptide or a composition as described above.

An eighth aspect of the invention relates to an isolated peptide or a composition as described above for preventing, ameliorating or treating-angiogenesis or an angiogenesis associated disease.

A ninth aspect of the invention relates to an isolated peptide or a composition as described above in the preparation of a medicament for the treatment of angiogenesis or an angiogenesis associated disease.

A tenth aspect of the invention relates to the use of an isolated peptide or a composition as described above for inhibiting angiogenesis.

An eleventh aspect of the invention relates to a method of preventing or treating angiogenesis or an angiogenesis associated disease in a subject, said method comprising administering to the subject an isolated peptide or a composition as described above.

A twelfth aspect of the invention relates to an isolated peptide or a composition as described above for preventing, ameliorating or treating myocardial-related disease or ischemia-reperfusion injury.

A thirteenth aspect of the invention relates to the use of an isolated peptide or a composition as described above in the preparation of a medicament for the treatment of myocardial-related disease or ischemia-reperfusion injury.

A fourteenth aspect of the invention relates to the use of an isolated peptide or a composition as described above as a myocardial protective agent.

A fifteenth aspect of the invention relates to a method of preventing or treating myocardial-related disease or ischemia-reperfusion injury in a subject, said method comprising administering to the subject an isolated peptide or a composition as described above.

A sixteenth aspect of the invention relates to an isolated peptide or a composition as described above for preventing or inhibiting endothelial cell growth.

A seventeenth aspect of the invention relates to the use of an isolated peptide, or a composition as described above in the preparation of a medicament for preventing or inhibiting endothelial cell growth.

An eighteenth aspect of the invention relates to a method of inducing cell death and/or apoptosis or cell cycle arrest in mammalian endothelial cells, said method comprising contacting mammalian endothelial cells with an isolated peptide or a composition as described above.

A ninteenth aspect of the invention relates to a nucleic acid sequence encoding a peptide as defined above, or a variant derivative, fragment or homologue thereof.

A twentieth aspect relates to a nucleic acid sequence which is complementary to the nucleotide sequence of the invention, or a variant, derivative, fragment or homologue thereof.

A further aspect of the invention relates to an antibody targeted to a peptide as described above, or a variant, derivative, fragment or homologue thereof.

A further aspect of the invention relates to a kit comprising an antibody as described above.

Results are expressed as mean±SD, n=6/group. Statistical analysis was performed versus control group. *p<0.05.

Figure 22:
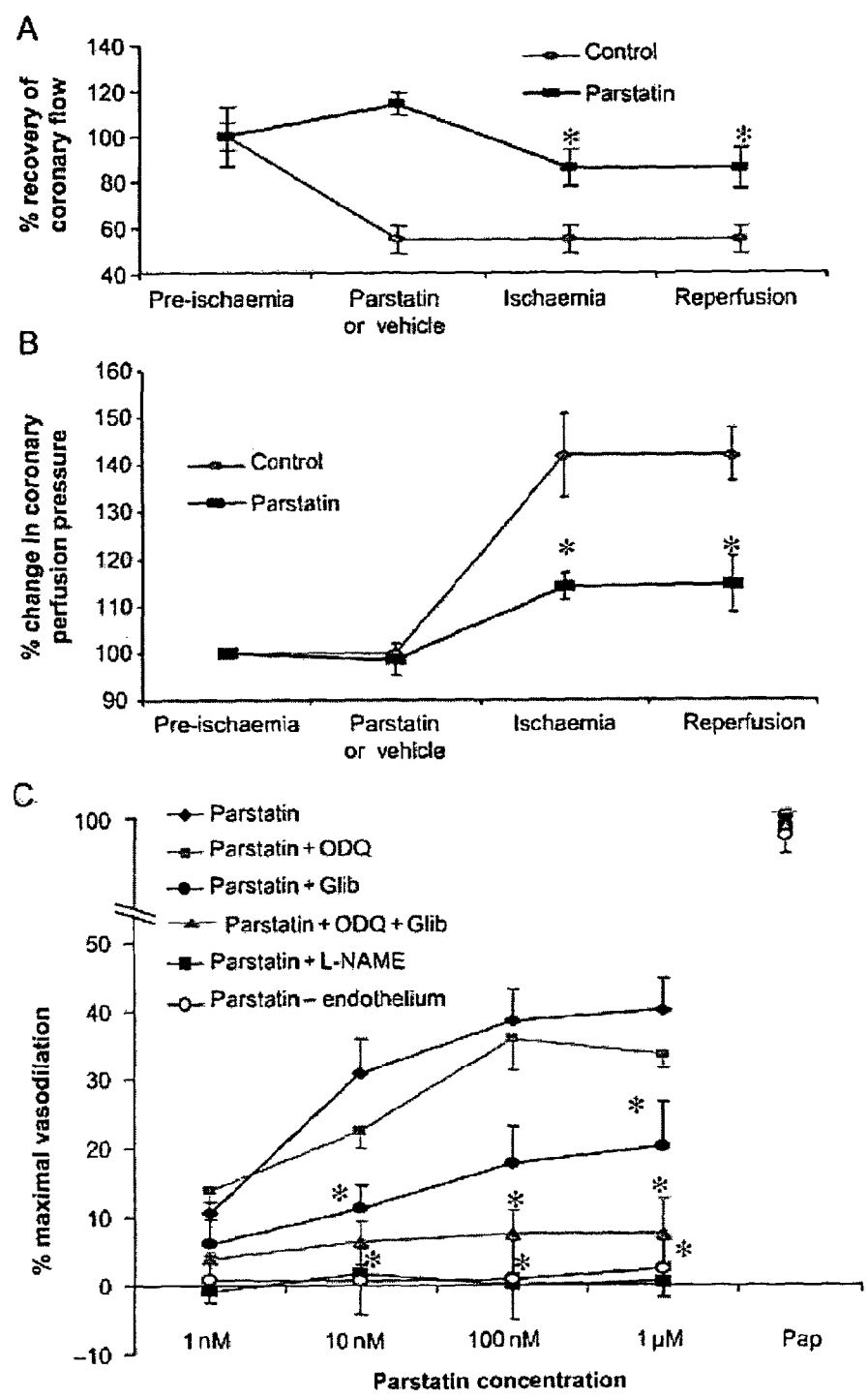

FIG. 22. Coronary response to parstatin (1-41) during ischemia and reperfusion. A, Parstatin (1-41) increases coronary flow during ischemia and reperfusion. Administration of parstatin (1-41) (1 µM) 15 min prior to ischemia and reperfusion resulted in an increase in coronary flow when compared with control values. B, Parstatin (1-41) decreases perfusion pressure in isolated rat hearts during ischemia and reperfusion. Isolated rat hearts were perfused with or without parstatin (1-41) (1 µM) for 15 min prior to regional ischemia and reperfusion. Perfusion pressure was monitored throughout the procedure. Average pressures from pre-ischemia, ischemia, and post-ischemia were compared. Results are expressed as mean±SD, n=6/group. Statistical analysis was performed versus control group. *p<0.05. C, Parstatin (1-41) causes vasodilation in rat coronary arterioles that were pre-constricted with endothelin-1. This vasodilation is completely abolished by the pre-treatment with L-NAME and partially abolished with ODQ or glibenclamide. In addition, denuding the vessels also abolish the vasodilatory effects of parstatin. Maximal dilation was achieved with papaverine (Pap). Results are expressed as mean±SD, n=6/group. Statistical analysis was performed versus control group. *p<0.05.

Figure 23:
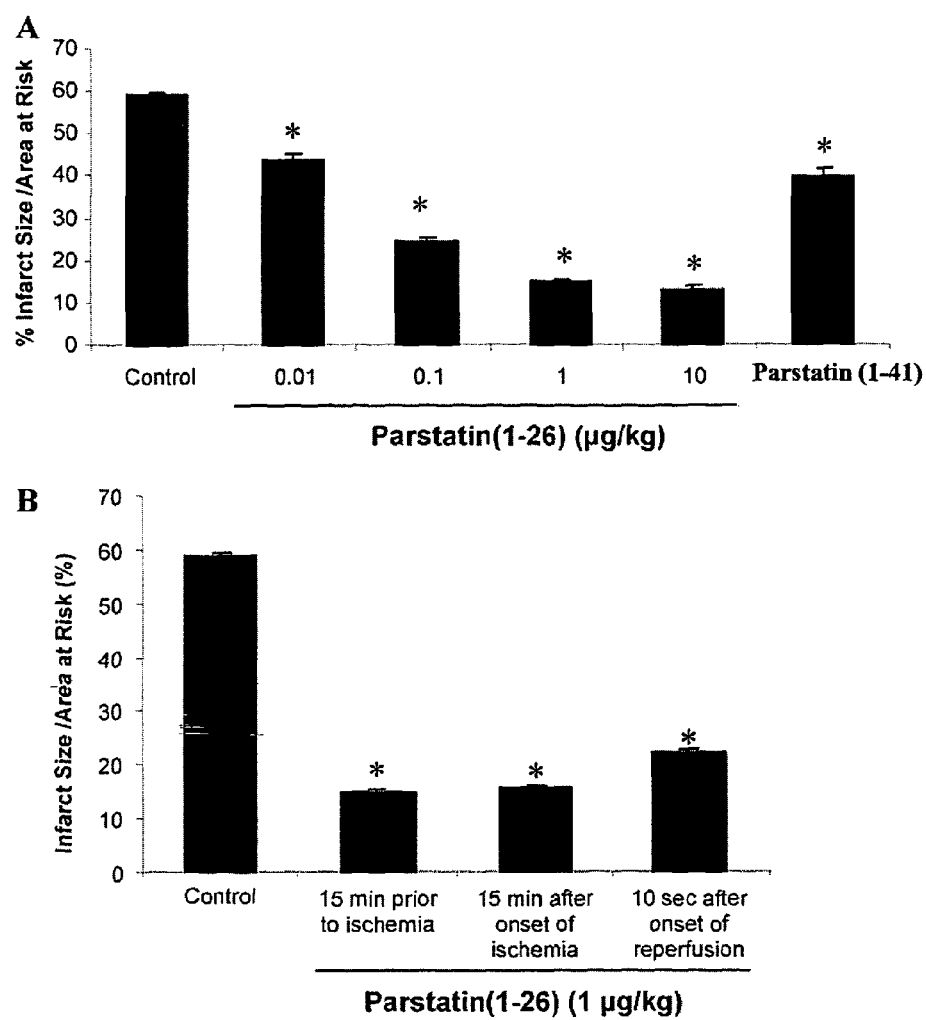

FIG. 23. Parstatin (1-26) fragment attenuates myocardial ischemia-reperfusion injury in rats. Analysis of the cardioprotective effects of parstatin (1-26) in vivo. A, Dose-response curve of parstatin (1-26). Rats were treated with either vehicle (DMSO), or parstatin (1-41) (10 µg/kg), or parstatin (1-26) (0.01-10 µg/kg) administered as an intravenous bolus 15 min before ischemia. Infarct size was determined after 30 min of regional ischemia and 120 min of reperfusion. B, Phase of action of parstatin (1-26) (1 µg/kg). Results are expressed as mean±SE, n=6 rats/group. Statistical analysis was performed versus control group. *p<0.05.

Figure 24:
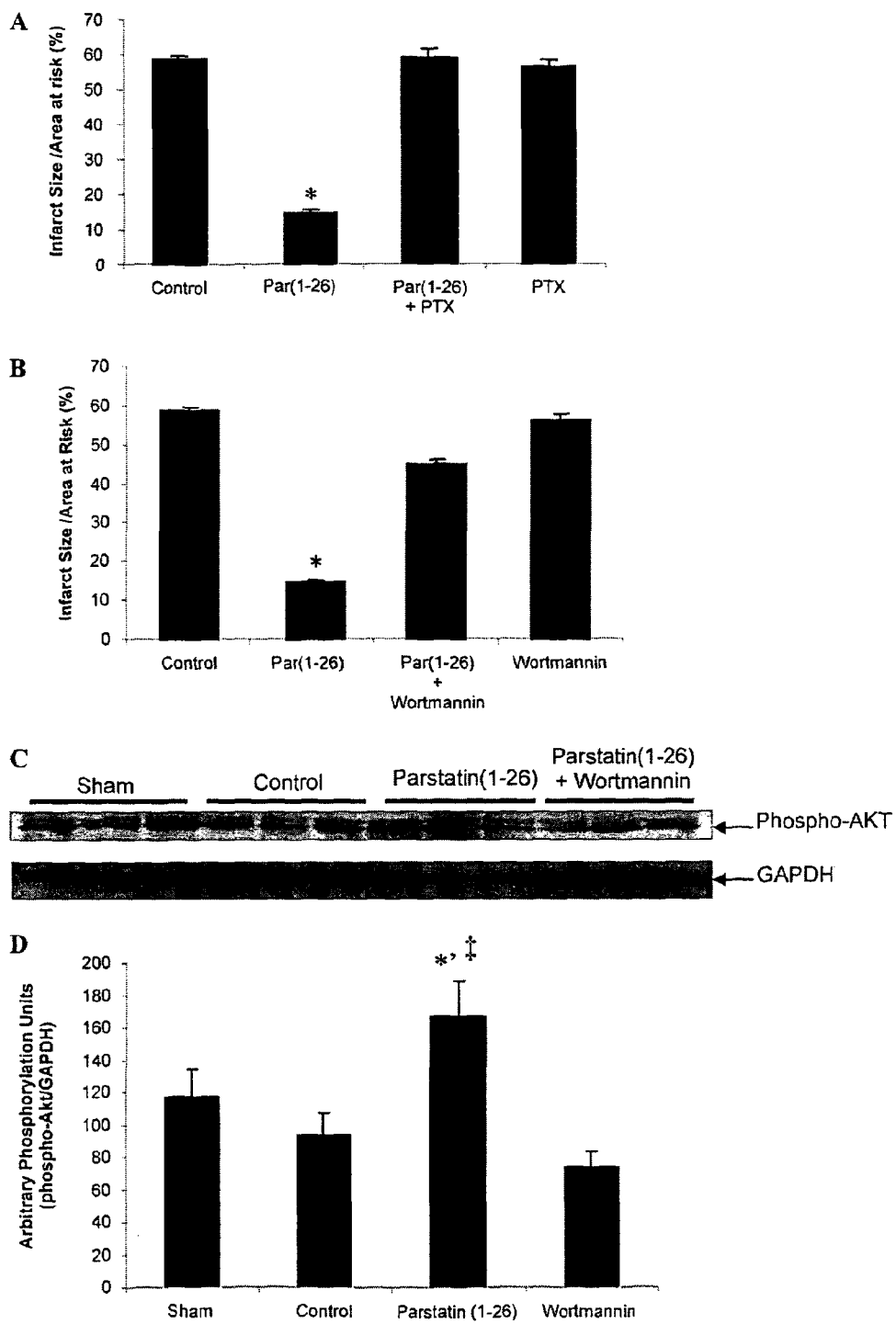

FIG. 24. The cardioprotective effects of parstatin (1-26) depend on Gi proteins and PI3K/Akt activation. Inhibition of Gi protein activation by pertussis toxin (PTX) completely abolished the cardioprotective effects of parstatin (1-26). PTX was injected 48 h before ischemia. The rats were treated with parstatin (1-26) (1 µg/kg) and subjected to 30 min of ischemia and 120 min of reperfusion. A, Infarct size expressed as a percentage of area at risk. Inhibition of PI3K/Akt with wortmannin (15 µg/kg) negates the cardioprotective effects of parstatin (1-26) (1 µg/kg). B, Infarct size expressed as a percentage of area at risk. Parstatin (1-26) increased activation of Akt after 5 min of reperfusion as measured by phosphorylation of Akt. Rats were treated with parstatin (1-26) (1 µg/kg) with or without wortmannin (15 µg/kg) and subjected to 30 min of regional ischemia and 5 min of reperfusion before the free wall of the left ventricle was harvested for protein extraction. Sham rats did not receive ischemia. Control rats received vehicle only. Results are expressed as mean±SE, n=6 rats/group. Statistical analysis was performed versus control group. *p<0.05. C, Immunoblot for phosphorylated Akt. GAPDH is the loading control. n=3/group. D, Bar graph showing expression strength of phosphorylated Akt after densitometric evaluation of signal strengths and normalization to the corresponding GAPDH expression. n=3/group. *p<0.05 versus drug-free control; ‡p<0.05 versus wortmannin-treated group.

Figure 25:
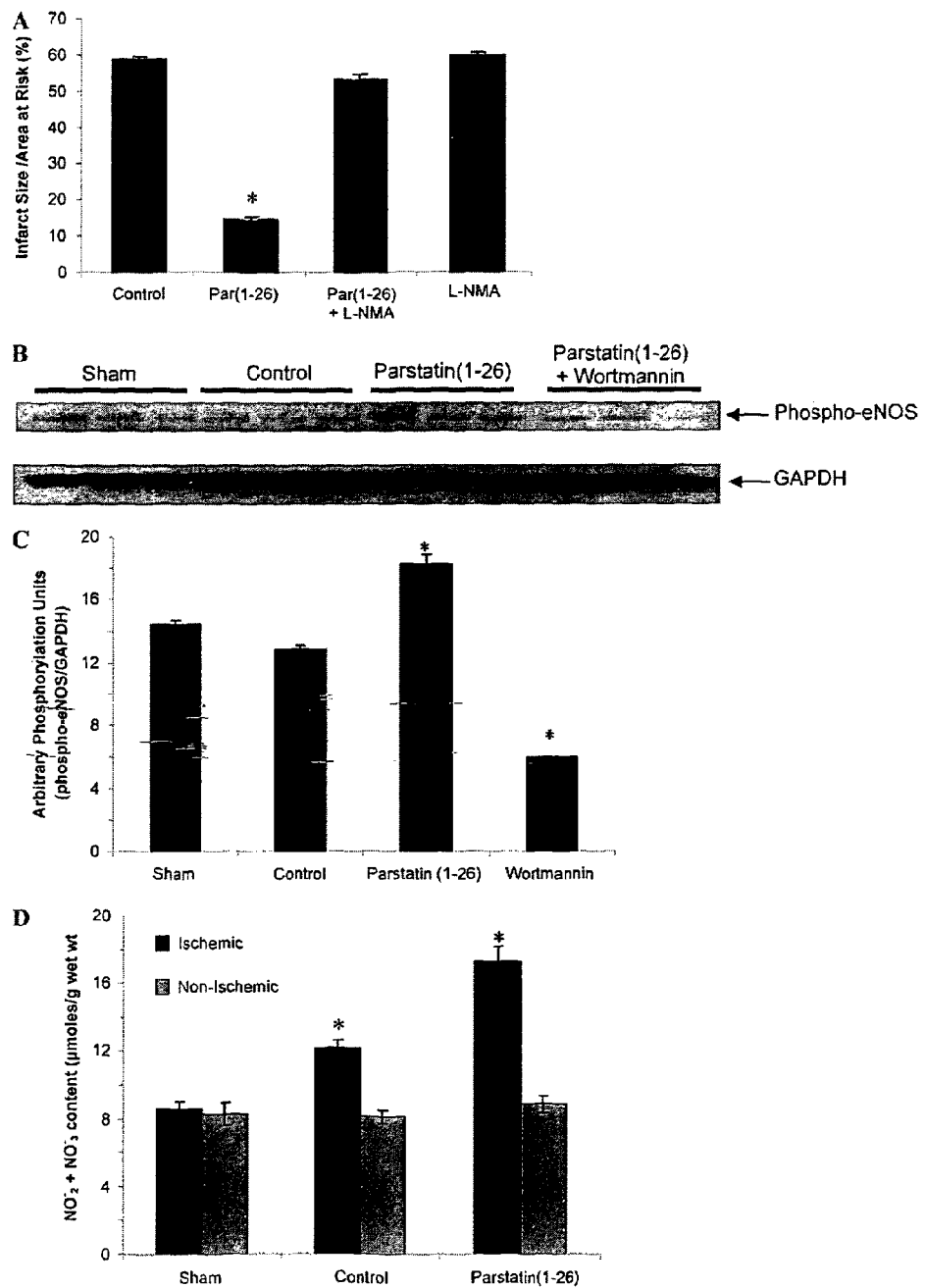

FIG. 25. The cardioprotective effects of parstatin (1-26) depend on NOS activation and nitric oxide production. Inhibition of NOS with L-NMA (15 mg/kg) negates the cardioprotective effects of parstatin (1-26) (1 µg/kg). A, Infarct size expressed as a percentage of area at risk. Results are expressed as mean±SE, n=6 rats/group. Statistical analysis was performed versus drug-free control group. *p<0.001. B, Immunoblot for phosphorylated eNOS. Parstatin (1-26) increased activation of endothelial NOS after 5 min of reperfusion as measured by phosphorylation of eNOS. Rats were subjected to 30 min of regional ischemia and 5 min of reperfusion before the free wall of the left ventricle was harvested for protein extraction. Sham rats did not receive ischemia. Control rats received vehicle only. Treated rats received parstatin (1-26) (1 µg/kg) with or without wortmannin (15 mg/kg). GAPDH is the loading control. n=3/group. C, The bar graph shows band intensities after densitometric evaluation and normalization of phosphorylated eNOS protein to the corresponding GAPDH protein. n=3/group; *p<0.05, versus drug-free control. D, Measurement of total nitrite plus nitrate from ischemic and nonischemic myocardium. Preischemic treatment with parstatin (1-26) (1 µg/kg) increases the myocardial nitric oxide content in ischemic tissue. Results are expressed as mean±SE, n=6 rats/group. Statistical analysis was performed versus drug-free control group. *p<0.001.

Figure 26:
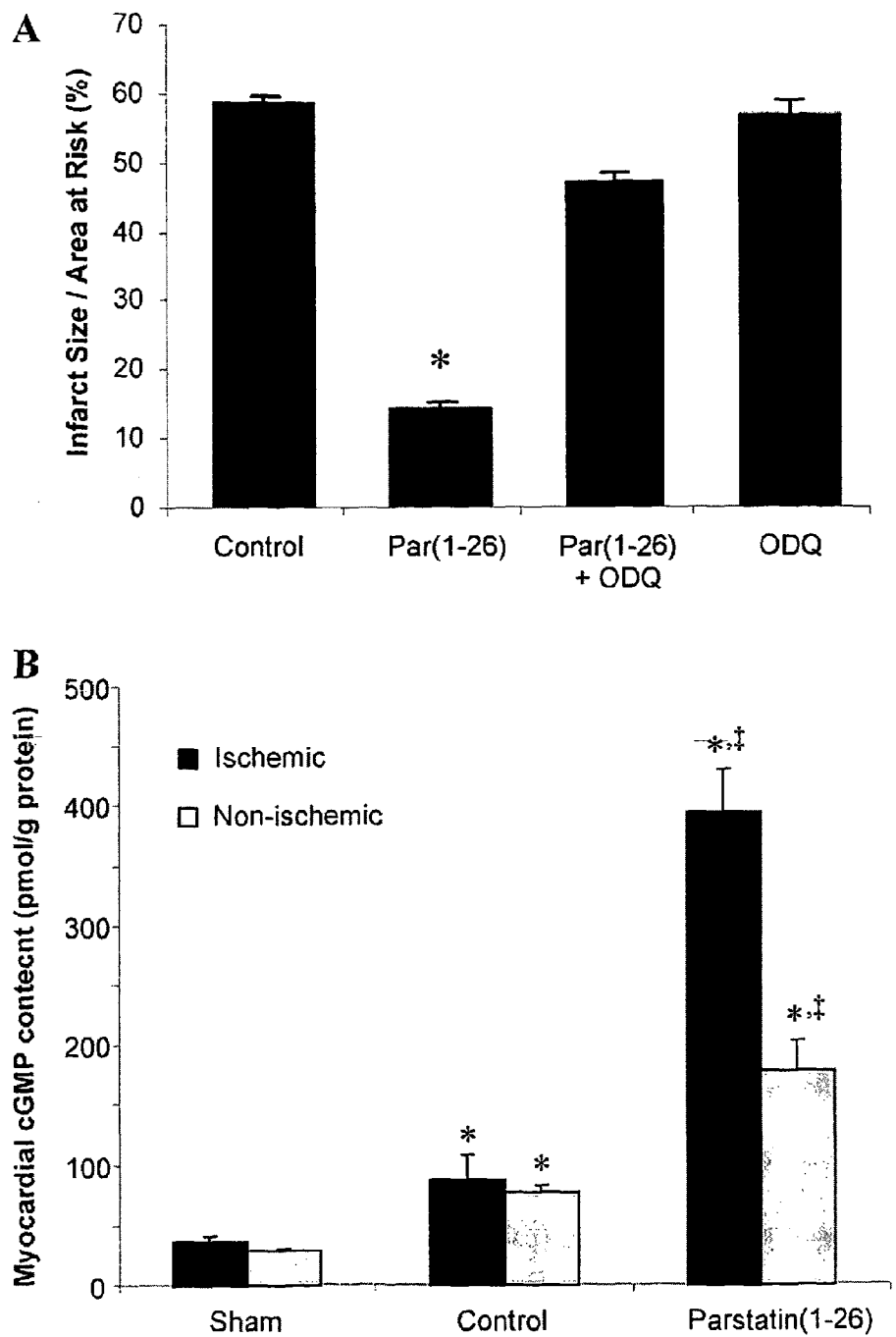

FIG. 26. The cardioprotective effects of parstatin (1-26) depend on soluble guanylyl cyclase activation and increased cyclic GMP production. Inhibition of sGC with ODQ (1 mg/kg) negates the cardioprotective effects of parstatin (1-26) (1 µg/kg). A, Infarct size expressed as a percentage of area at risk. Pre-ischemic treatment with parstatin (1-26) (1 µg/kg) increases the myocardial cGMP content. B, Measurement of cyclic GMP in ischemic and nonischemic tissue. Results are expressed as mean±SE, n=6 rats/group. Statistical analysis was performed versus drug-free control group. *p<0.001.

Figure 27:
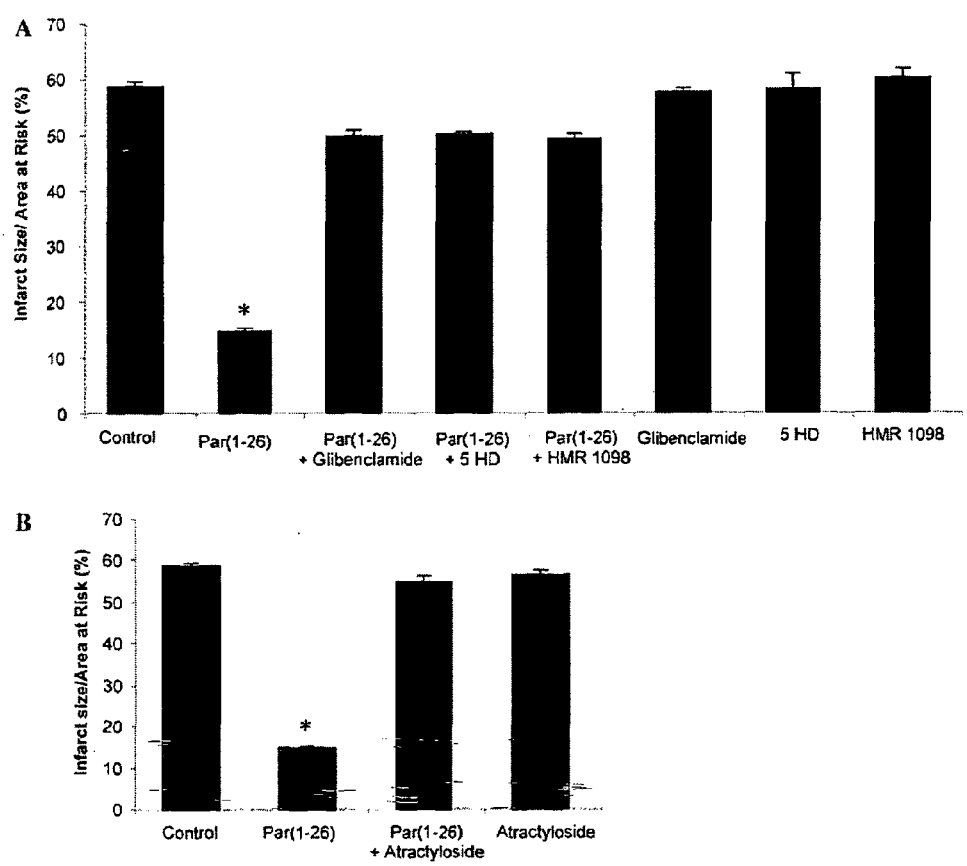

FIG. 27. The cardioprotective effects of parstatin (1-26) depend on $K_{ATP}$ channels and mPTP. Inhibition of $K_{ATP}$ channel activation with glibenclamide (3 mg/kg), HMR 1098 (3 mg/kg); or 5-HD (10 mg/kg) abolishes the cardioprotective effects of parstatin (1-26). Rats were treated with the inhibitors with or without parstatin (1-26) (1 µg/kg) before 30 min of regional ischemia and 120 min of reperfusion. A, Infarct size expressed as a percentage of area at risk. The cardioprotection of parstatin (1-26) was abolished by the mPTP opener, atractyloside. Treated rats received parstatin (1-26) (1 µg/kg) with or without atractyloside (3 mg/kg). B, Infarct size expressed as a percentage of area at risk. Results are expressed as mean±SE, n=6 rats/group. Statistical analysis was performed versus drug-free control group. *p<0.001.

Figure 28:
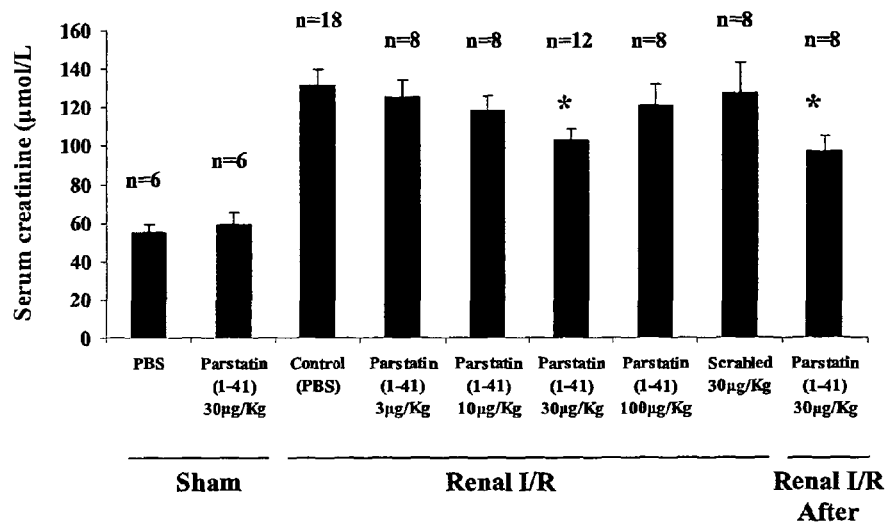
Figure 28:
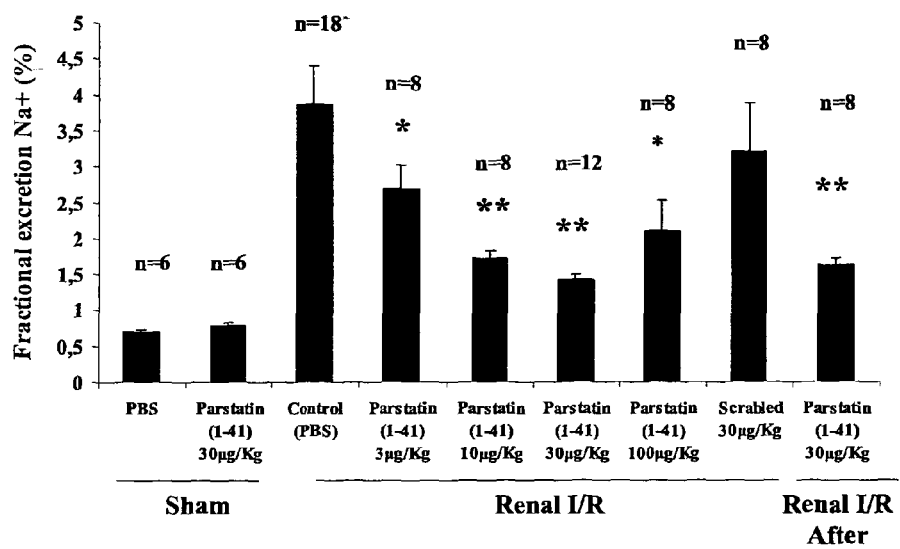
Figure 28:
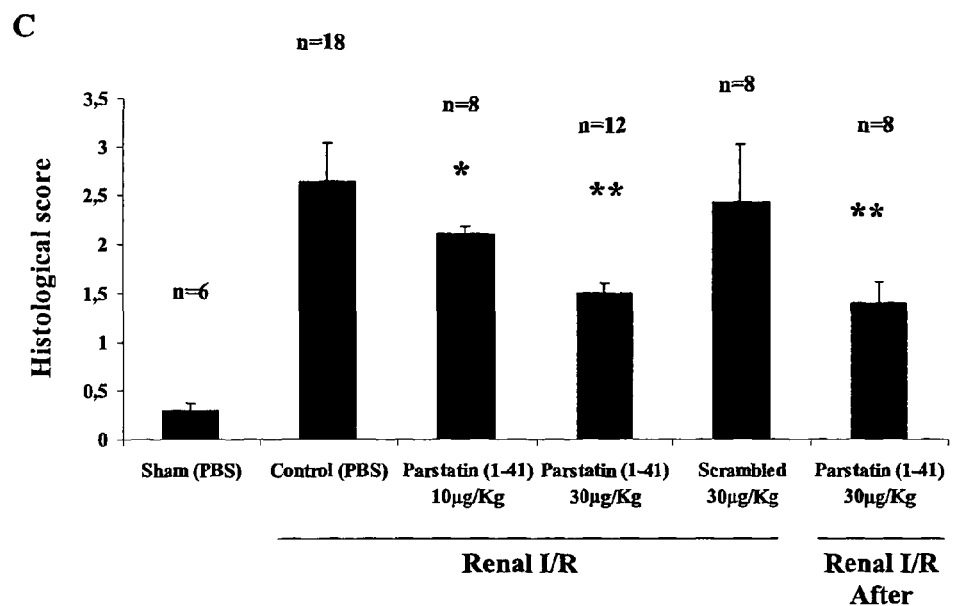

FIG. 28. Parstatin (1-41) protects from acute renal injury in a rat model of ischemia and reperfusion-induced nephropathy. Wistar rats were subjected to 45 min of renal ischemia followed by 4 hours of reperfusion. Parstatin (1-41), at doses ranging from 3 to 100 µg/Kg, was administered intravenously 15 min prior to ischemia (renal I-R) or 10 seconds after the onset of reperfusion (Renal I-R After). Scrambled parstatin (30 µg/Kg) was administrated intravenously 15 min prior to ischemia. Control rats were treated with vehicle only (PBS), while sham rats did not undergo ischemia and reperfusion. At the end of reperfusion, the ischemia-reperfusion injury was assessed by analyzing biochemical markers of renal impairment and histologically. Serum creatinine (A), franctional excretion of Na+ (B), and histological score (C) were estimated. Results are expressed as mean±SE for each group calculated from the indicated number (n) of rats. *p<0.05, **p<0.01.

Figure 29:
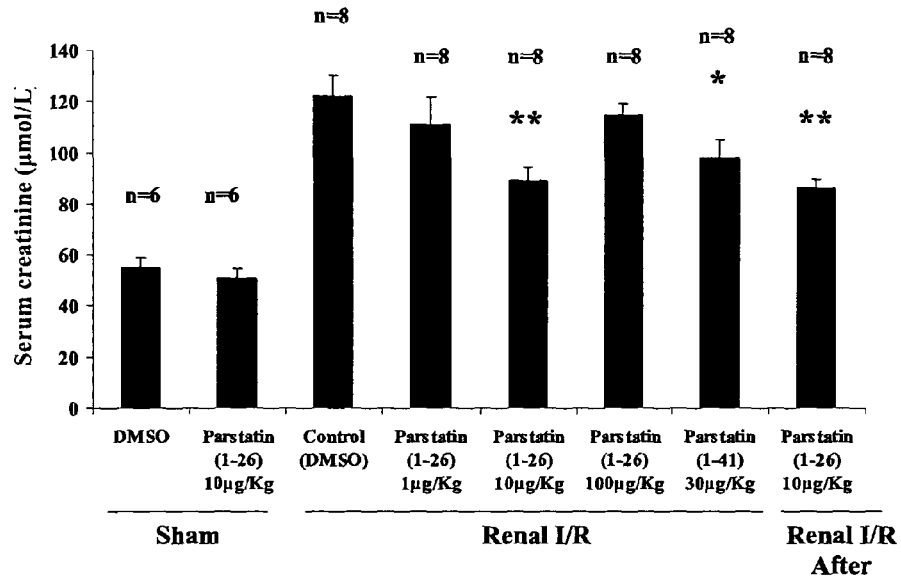
Figure 29:
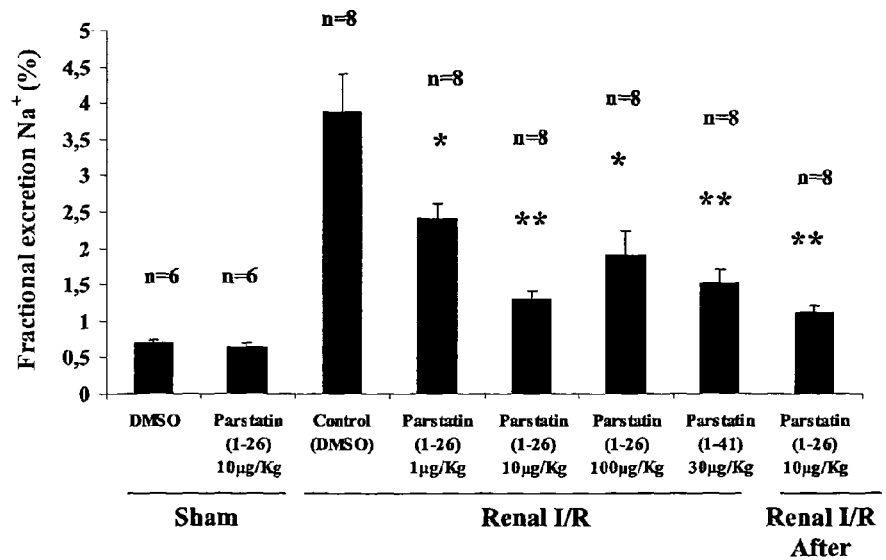
Figure 29:
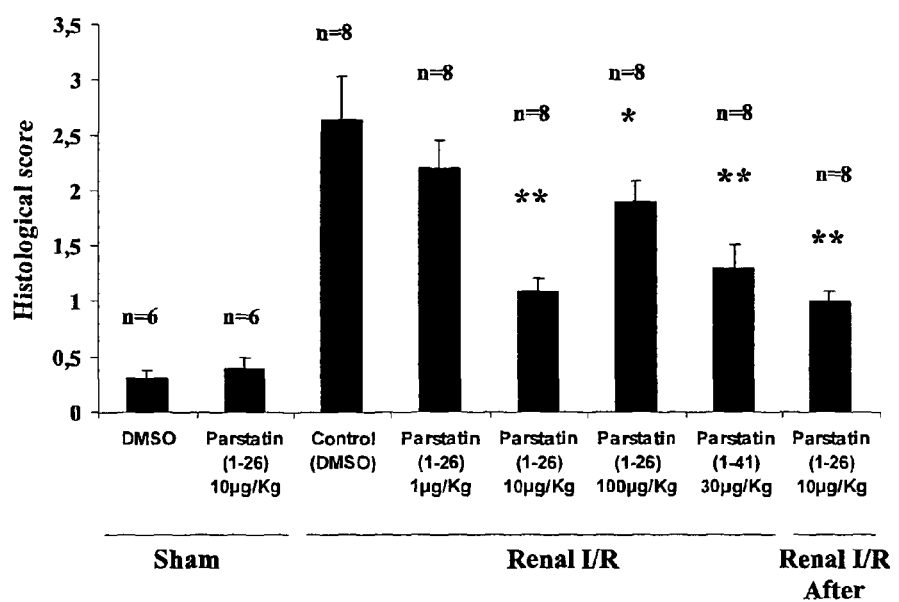

FIG. 29. Parstatin (1-26) protects from acute renal injury in a rat model of ischemia and reperfusion-induced nephropathy. Wistar rats were subjected to 45 min of renal ischemia followed by 4 hours of reperfusion. Parstatin (1-26), at doses ranging from 1 to 100 µg/Kg, was administered intravenously 15 min prior to ischemia (renal I-R) or 10 seconds after the onset of reperfusion (Renal I-R After). Control rats were treated with vehicle only (DMSO), while sham rats did not undergo ischemia and reperfusion. At the end of reperfusion, the ischemia-reperfusion injury was assessed by analyzing biochemical markers of renal impairment and histologically. Serum creatinine (A), franctional excretion of Na+ (B), and histological score (C) were estimated. Results are expressed as mean±SE for each group calculated from the indicated number (n) of rats. *$p<0.05$, **$p<0.01$.

DETAILED DESCRIPTION OF THE INVENTION

Aspects of the invention are set forth in the paragraphs below and in the accompanying claims.

The invention includes a class of bioactive peptide molecules that have the ability to modulate cell functions and physiological and pathological processes. These peptides are collectively referred to as parstatin peptides. The invention further includes various therapeutic uses of said parstatin peptides.

For the avoidance of doubt, the invention encompasses the following embodiments which may be read separately or in combination with one or more other embodiments. The preferred features described below apply mutatis mutandis to all aspects of the invention. Specifically, the therapeutic applications described below apply to each of the various parstatin peptides disclosed herein.

Parstatin Polypeptides and Peptides

A first aspect of the invention relates to an isolated peptide comprising a sequence selected from SEQ ID NO:1 (1-41), SEQ ID NO:9 (1-26) and SEQ ID NO:4 (24-41), or a variant, derivative, fragment or homologue thereof.

The term "isolated" means that the peptide is at least substantially free from at least one other component with which the sequence is naturally associated in nature and as found in nature. In one aspect, preferably the substance is in a purified form. The terms "purified" or "substantially purified" or "substantially isolated" mean that a substance is in a relatively pure state—least 60% free, preferably 75% free, preferably 90% free, preferably 95% free and more preferably 99% free from other components with which it is naturally associated.

In one preferred embodiment, the invention relates to an isolated peptide consisting of a sequence selected from SEQ ID NO:1 (1-41), SEQ ID NO:9 (1-26) and SEQ ID NO:4 (24-41), or a variant derivative, fragment or homologue thereof.

The peptides of the invention comprise at least an active portion of the peptides of SEQ ID NOS: 1-3 including the full-length peptide or substantially homologous polypeptides thereto.

In one preferred embodiment, the peptide of the invention comprises amino acids 1-41 of SEQ ID NO:1, or is a variant, derivative, fragment or homologue thereof.

In a more preferred embodiment, the peptide of the invention consists of amino acids 1-41 of SEQ ID NO:1, or is a variant, derivative, fragment or homologue thereof.

In another preferred embodiment, the peptide of the invention comprises amino acids 1-26 of SEQ ID NO:1, or is a variant, derivative, fragment or homologue thereof.

In a more preferred embodiment, the peptide of the invention consists of amino acids of SEQ ID NO:9, or is a variant, derivative, fragment or homologue thereof.

In another preferred embodiment, the peptide of the invention comprises amino acids 24-41 of SEQ ID NO:1, or is a variant, derivative, fragment or homologue thereof.

In a more preferred embodiment, the peptide of the invention consists of amino acids of SEQ ID NO:4, or is a variant, derivative, fragment or homologue thereof.

The peptide of the invention may be an isolated polypeptide and/or may be a non-naturally occurring polypeptide. The peptide may be a human peptide or a peptide originating from another species.

The terms "parstatin", "parstatin peptide" and "parstatin polypeptide" are used interchangeably and refer to a peptide comprising at least an active portion of the peptide of cleaved peptide of human PAR1 (Genbank Accession Number AF019616) with the sequence: MGPRRLLLVAA-CFSLCG-PLLSARTRARRPESKATNATLDPR (SEQ ID NO: 1) including the full-length peptide of SEQ ID NO:1 or a substantially homologous polypeptide thereto. The parstatin peptides described herein may also be referred to as the bioactive molecules of the invention.

In one preferred embodiment, the peptide of the invention is at least 41 amino acids in length. Preferably, the peptide is around 41 amino acids or greater in length.

In another preferred embodiment, the peptide of the invention is from 26 to 35 amino acids in length.

In another preferred embodiment, the peptide of the invention is from 26 to 30 amino acids in length.

In one highly preferred embodiment, the peptide is about 41 amino acids and approximately 4.5 kDa in size. Such peptides are naturally generated by cleavage of the N-terminal domain of the protease activated receptor-1 (PAR1). Cleavage and release of the N-terminal domain results in the generation of a new N-terminus on the receptor, activating the receptor. Full length Parstatin is predicted to be less than 41 residues in length because of an initial hydrophobic domain of approximately 21 to 23 amino acids (MG-PRRLLLVAACFSLCGPLLSAR (amino acids 1-23 of SEQ ID NO: 1) that may represent a putative signal sequence.

PAR1 belongs to the small subgroup of G protein-coupled receptors (5-10%) possessing N-terminal signal peptides. Signal peptides have been shown to facilitate export of many secretory proteins across eukaryotic endoplasmic reticulum and are believed to be cleaved-off after mediating the endoplasmatic reticulum targeting/insertion process. However, this may not always be the case. Interestingly, parstatin contains an asparagine-linked (Asn35) glycosylation site, which may prevent proteolysis of signal sequence. In addition some evidence that parstatin may released from thrombin-activated platelets has also been reported (Ramachandran et al, 1994, Thromb Haemost, 78: 1119-1124; Furman et al, 2000, Thromb Haemost, 84: 897-903).

As used herein, the term "amino acid sequence" is synonymous with the term "polypeptide" and/or the term "protein" and/or the term "peptide" and/or the term "polypeptide sequence" and/or the term "peptide sequence" and/or the term "protein sequence". The parstatin polypeptides of the invention may be prepared and/or isolated from a suitable source, or may be made synthetically or may be prepared by use of recombinant DNA techniques. The terms apply to amino acid polymers in which one or more amino acid residue is an artificial chemical mimetic of a corresponding naturally occurring amino acid, as well as to naturally occurring amino acid polymers and non-naturally occurring amino acid polymer.

As demonstrated herein, the parstatin peptides of the invention are potent inhibitors of angiogenesis, endothelial cell growth, migration, and differentiation. As further demonstrated herein, the parstatin peptides of the invention promote endothelial cell apoptosis and block the angiogenesis process. In addition, the parstatin peptides of the invention have been demonstrated to be effective in the prevention and treatment of myocardial ischemia/reperfusion injury and of acute renal failure and associated disease states. Moreover, the parstatin peptides of the invention are demonstrated to work cross species with mouse parstatin having an effect on human cells and tissues, and both mouse and human parstatin having an effect on rat cells and tissue.

Parstatin Variants

The present invention also encompasses variants and derivatives and homologues of the parstatin peptides that are active in vitro and/or in vivo. The present invention therefore includes a 41 amino acid parstatin peptide (full length SEQ ID NO: 1), derivatives and variants of the parstatin peptide, and biologically-active fragments of the parstatin peptide, including truncations of the N- and/or C-terminus of SEQ ID NO: 1, and/or internal deletions.

As used herein, the term "variant" is used to include the peptides of SEQ ID Nos 1, 2, 3, 4, 5, 6, 7, 8, 9 and 10 being modified by at least one of deletion, addition or substitution of one or more amino acid residues, or by substitution of one or more natural amino acid residues by the corresponding D-stereomer or by a non-natural amino acid residue, chemical derivatives of the peptides, cyclic peptides derived from the peptides or from the peptide derivatives, dual peptides, multimers of the peptides and any of said peptides in the D-stereisomer form or the order of the final two residues at the C-terminus residues are reversed; provided that such variants retain the activity of the parent peptide. As used hereinafter, the term "substitution" is used as to mean "replacement" i.e. substitution of an amino acid residue means its replacement.

As used herein, the term "derivative" refers to a peptide arising from the modification of the peptides of the invention, wherein the peptides of the invention serve as the starting point. For example, a longer polypeptide incorporating the peptide of the invention may be a derivative, as may a peptide of the invention which incorporates the addition of further chemical groups.

As used herein, the term "fragment" refers to a portion of the parstatin peptides of the invention or their variants or derivatives. A fragment typically lacks one or more amino acids compared to the full length peptides of the invention.

The term "parstatin peptides" or "parstatin polypeptides" includes longer peptides with N- and/or C-terminal extensions or insertions in the 4.5 kDa peptide of SEQ ID NO: 1, and modified peptides and proteins that have a substantially similar amino acid sequence, and which have the ability to modulate endothelial cell functions and physiological and pathological processes. The term "parstatin peptides" or "parstatin polypeptides" also includes shorter peptides with one or more amino acids is removed from either or both N- and C-terminal or from internal regions in the 4.5 kDa peptide of SEQ ID NO: 1 and modified peptides that have a substantially similar amino acid sequence, and which have the ability to modulate endothelial cell functions and physiological and pathological processes.

For example, substitutions of amino acids, wherein the replacement of an amino acid with a structurally or chemically similar amino acid does not significantly alter the structure, conformation or activity of the peptide (i.e., a conservative substitution), is well known in the art. As demonstrated herein, mouse parstatin has an effect on both human and rat cells and tissues. Human parstatin has an effect on rat cells and tissues. Sequence alignments demonstrate that human and mouse parstatin (N-terminus of Accession No. AAB38308.1) are 63% identical and 80% similar over the 41 amino acid length of the peptide sequences. The N-terminal 41 amino acids of the thrombin receptor of *Cricetulus longi-caudatus* (long-tailed dwarf hamster, Accession No. CAA43957.1) are 68% identical and 85% similar to human parstatin. The N-terminal 41 amino acids of rat thrombin receptor (Accession No. P26824) are 67% identical and 75% similar to human parstatin over amino acids 1-37. The N-terminal 41 amino acids of the thrombin receptor of *Bos Taurus* (cow, Accession No. A7YY44) are 63% identical and 68% similar over the first 41 amino acids. The N-terminal 41 amino acids of the thrombin receptor of *Macaca mulatta* (rhesus monkey, Accession No. XP.sub.-001106136) are 92% identical and 92% similar over the first 41 amino acids. An alignment of the sequences generated using ClustalW2 is presented below and can be used to identify amino acids likely more or less tolerant to mutation.

| SEQ ID | | | |
|---|---|---|---|
| human | MGPRRLLLVAACFSLCGPLLSARTRARRPESKATN ATLDPR | 41 | 1 |
| monkey | MGPRRLLLVAACLCLCGPLLSARTRARRPASKATN ATLDPR | 41 | 5 |
| mouse | MGPRRLLIVALGLSLCGPLLSSRVPMSQPESERTD ATVNPR | 41 | 2 |
| rat | MGPRRLLLVAVGLSLCGPLLSSRVPMRQPESERMY ATPYAT | 41 | 6 |
| hamster | MGPQRLLLVAAGLSLCGPLLSSRVPVRQPESEMTD ATVNPR | 41 | 7 |
| bovine | MGPRWLLLWAAGLGLCSPLVSARTRGPRPGTDPTN *::* :.:*:*. :* :. GTLGPR .* . | 41 | 8 |

For example, mutation of amino acids conserved across all species which are indicated with an * (e.g., amino acids 1-3, 6-7, 10, 15-16, 18-19, 21, 23, 29, and 37) would likely be more disruptive to function than mutations at amino acids that are not conserved across species. Mutations at non-conserved amino acids (e.g., amino acids 5, 9, 11-12, 14, 17, 20, 22, 24, 25-27, 30, 33-35, 38-39, and 41) would likely be more well tolerated. Conservative amino acid substitutions would likely be tolerated at positions indicated with : or . (e.g., positions 4, 8, 13, 17, 20, 22, 28, 31, 32, 36, 40).

The peptides of the inventions may also have deletions, insertions or substitutions of amino acid residues which produce a silent change and result in a functionally equivalent substance. Deliberate amino acid substitutions may be made on the basis of similarity in amino acid properties (such as polarity, charge, solubility, hydrophobicity, hydrophilicity, and/or the amphipathic nature of the residues) and it is therefore useful to group amino acids together in functional groups. Amino acids can be grouped together based on the properties of their side chain alone. However it is more useful to include mutation data as well. The sets of amino acids thus derived are likely to be conserved for structural reasons. These sets can be described in the form of a Venn diagram (Livingstone C. D. and Barton G. J. (1993) "Protein sequence alignments: a strategy for the hierarchical analysis of residue conservation" *Comput. Appl Biosci.* 9: 745-756) (Taylor W. R. (1986) "The classification of amino acid conservation" *J. Theor. Biol.* 119; 205-218). Conservative substitutions, as described above, may be made, for example according to the table below which describes a generally accepted Venn diagram grouping of amino acids.

| Set | | Sub-set | |
|---|---|---|---|
| Hydrophobic | F W Y H K M I L V A G C | Aromatic | F W Y H |
| | | Aliphatic | I L V |
| Polar | W Y H K R E D C S T N Q | Charged | H K R E D |
| | | Positively charged | H K R |
| | | Negatively charged | E D |
| Small | V C A G S P T N D | Tiny | A G S |

The invention further encompasses parstatin peptides comprising homologous substitution (substitution and replacement are both used herein to mean the interchange of an existing amino acid residue, with an alternative residue) that may occur i.e. like-for-like substitution such as basic for basic, acidic for acidic, polar for polar etc. Non-homologous substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as 0), pyriylalanine, thienylalanine, naphthylalanine and phenylglycine.

Parstatin peptides having mutations or alterations that do not eliminate parstatin peptide function are also included within the scope of the invention. Such mutations or alterations can alter properties of the peptide such as bioavailability or allow for modification of the peptide with various groups. Groups may be to allow for detection of parstatin peptides (e.g., radioactive or fluorescent label) or to change or augment the activity of the peptide (e.g., a chemotherapeutic agent). Such substitutions fall within the scope of the invention. These include peptides with parstatin activity that have amino acid substitutions or have sugars or other molecules attached to amino acid functional groups. Methods for site directed mutagenesis are well known and saturation mutational analysis is a common method, especially in short peptides that can be generated by synthetic methods. Moreover, as demonstrated herein, parstatin peptides have activity across species demonstrating that sequence variation is tolerable and does not completely disrupt activity of parstatin peptides. Moreover, sites of variation between species can provide an indication of sites that can be altered while retaining function.

Preferably the parstatin peptides have at least 30%, 40%, 50%, 60%, 70%, 80%, 85%, 90%, or 95% activity as compared to the peptide of SEQ ID NO: 1 in at least one of the assays taught herein. Such assays are routine in the art. In one embodiment, the assay is an angiogenesis assay. In another embodiment, the assay is a cell proliferation assay. In another embodiment, the assay is a cell mitogenesis assay. In another embodiment, the assay is a cell migration assay. In another embodiment, the assay is a cell differentiation assay. In another embodiment, the assay is an apoptosis assay. In another embodiment, the assay is a cell cycle progression assay. In another embodiment, the assay is a kinase activation assay. In another embodiment, the assay is an ischemia/reperfusion assay.

In certain preferred embodiments, the peptide includes 5 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, 30 or more, 31 or more, 32 or more, 33 or more, 34 or more, 35 or more, 36 or more, 37 or more, 38 or more, 39 or more, 40 or more, or 41 consecutive amino acids of SEQ ID NO: 1.

In one preferred embodiment, the peptide is an 18 amino acid fragment of SEQ ID NO: 1 including amino acids 24-41 of SEQ ID NO: 1 (SEQ ID NO:4).

In another preferred embodiments, the peptide is a 26 amino acid fragment of SEQ ID NO 1 including amino acids 1-26 of SEQ ID NO: 1 (SEQ ID NO:9).

In another preferred embodiment, the peptide includes a parstatin peptide sequence. covalently linked, e.g., through a peptide bond, to a non-parstatin peptide sequence.

As used herein the term "homologue" means an entity having a certain homology with the amino acid sequences of the invention and/or the nucleotide sequences of the invention. Here, the term "homology" can be equated with "identity".

In the present context, a homologous sequence is taken to include an amino acid sequence which may be at least 60, 65, 70, 75, 80, 85 or 90% identical, preferably at least 95, 96, 97, 98 or 99% identical to the subject sequence.

"Substantial sequence homology" or "substantially homologous" means at least about 60% homology, at least about 70% homology, at least about 80% homology, at least about 90% homology, at least about 95% homology, preferably at least about 99% homology between the amino acid sequence compared to the reference sequence. "Substantial sequence identity" or "substantially identical" means at least about 60% identity, at least about 70% identity, at least about 80% identity, at least about 90% identity, at least about 95% identity, preferably at least about 99% identity to the reference sequence. The words "homology" and "identity" are used interchangeably.

Homology comparisons can be conducted by eye, or more usually, with the aid of readily available sequence comparison programs. These commercially available computer programs can calculate percentage homology (% homology) between two or more sequences.

Percentage homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (Devereux et al 1984 Nuc. Acids Research 12 p387). Examples of other software than can perform sequence comparisons include, but are not limited to, the BLAST package (see Ausubel et al., 1999 *Short Protocols in Molecular Biology*, 4$^{th}$ Ed—Chapter 18), FASTA (Altschul et al., 1990 *J. Mol. Biol.* 403-410) and the GENEWORKS suite of comparison tools. Both BLAST and FASTA are available for offline and online searching (see Ausubel et al., 1999, *Short Protocols in Molecular Biology*, pages 7-58 to 7-60).

However, for some applications, it is preferred to use the GCG Bestfit program. A new tool, called BLAST 2 Sequences is also available for comparing protein and nucleotide sequence (see *FEMS Microbiol Lett* 1999 174(2): 247-50; *FEMS Microbiol Lett* 1999 177(1): 187-8 and tatiana@ncbi.nlm.nih.gov).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). For some applications, it is preferred to use the public default values for the GCG package, or in the case of other software, the default matrix, such as BLOSUM62.

Alternatively, percentage homologies may be calculated using the multiple alignment feature in DNASIS™ (Hitachi Software), based on an algorithm, analogous to CLUSTAL (Higgins D G & Sharp P M (1988), *Gene* 73(1), 237-244).

Once the software has produced an optimal alignment, it is possible to calculate % homology, preferably % sequence identity. The software typically does this as part of the sequence comparison and generates a numerical result.

The invention further encompasses compositions in which the parstatin sequence contains a peptidomimetic. For example, the invention includes parstatin compounds in which one or more peptide bonds have been replaced with an alternative type of covalent bond, which is not susceptible to cleavage by peptidases (a "peptide mimetic" or "peptidomimetic"). Where proteolytic degradation of peptides following injection into the subject is a problem, replacement of a particularly sensitive peptide bond with a non-cleavable peptide mimetic renders the resulting peptide more stable and thus more useful as a therapeutic. Such mimetics, and methods of incorporating them into peptides, are well known in the art. Similarly, the replacement of an L-amino acid residue (e.g., with a D-amino acid) renders the peptide less sensitive to proteolysis.

Additionally, the peptides of the invention can be synthesized as retro-inverso isomers, which include peptides of reverse sequence- and chirality (Jameson et al., Nature, 368: 744-746, 1994; Brady et al., Nature, 368: 692-693, 1994). The net result of combining D-enantiomers and reverse synthesis is that the positions of carbonyl and amino groups in each amide bond are exchanged, while the position of the side-chain groups at each alpha carbon is preserved. For example, if the peptide model is a peptide formed of L-amino acids having the sequence ABC, the retro-inverso peptide analog formed of D-amino acids would have the sequence CBA. The procedures for synthesizing a chain of D-amino acids to form the retro-inverso peptides are known in the art.

Another aspect of the invention relates to conjugates comprising peptides of the invention. For example, the invention includes compositions in which the parstatin peptide or a part of it is conjugated with a "cell-penetrating moiety" or "membrane-tethering moiety". Cell-penetrating moiety is a compound which mediates transfer of a substance from an extracellular space to an intracellular compartment of a cell. Cell-penetrating moieties shuttle a linked substance (e.g., parstatin peptides, fragments, and analogs) into the cytoplasm or to the cytoplasmic space of the cell membrane. Membrane-tethering moiety is a compound which associates with or binds to a cell membrane. Thus, the membrane-tethering moiety brings the substance (e.g., parstatin peptides, fragments, and analogs) to which the membrane-tethering moiety is attached in close proximity to the membrane of a target cell. For example, a cell penetrating or membrane-tethering moiety is a hydrophobic moiety. Cell-penetrating and membrane-tethering moieties include a lipid, cholesterol, phospholipids, steroid, sphingosine, ceramide, or a fatty acid moiety. The cell-penetrating or membrane-tethering moiety is attached to the C-terminal amino acid, the N-terminal amino acid, or to an amino-acid between the N-terminal and C-terminal amino acid of the parstatin or parstatin fragment.

The invention also includes compositions in which the parstatin peptides, fragments, and analogues are conjugated with sugar molecules. Glycosylation is a universal characteristic of proteins in nature, which determines their physico-chemical and biological properties. Design and synthesis of glycopeptides is a topic of intense research in the last years, since the carbohydrate modification can improve the pharmacokinetic characteristics, or otherwise enhance or alter the biologic activity and can be used as a tool to study the biologic functions.

The parstatin peptides of the present invention can be made by automated peptide synthesis methodologies well known to one skilled in the art. Alternatively, parstatin, of the present invention may be isolated from larger proteins, such as human PAR1, rat PAR1, mouse PAR1, and primate PAR1 proteins that share a common or similar N-terminal amino acid sequence.

The parstatin peptides of the invention can be produced upon the proteolysis of PAR1 by proteases such as thrombin, plasmin, activated protein C, metalloprotease-1. Parstatin peptides can also be produced from recombinant sources, from genetically altered cells implanted into animals, and from platelets and cell cultures as well as other sources. It is anticipated that parstatin is made in cells of the nervous system and tumors. Parstatin can be isolated from body fluids including, but not limited to, serum, urine, and ascites, or synthesized by chemical or biological methods (e.g. cell culture, recombinant gene expression, peptide synthesis, and in vitro enzymatic catalysis of precursor molecules to yield active parstatin). Recombinant techniques include gene amplification from DNA sources using the polymerase chain reaction (PCR), and gene amplification from RNA sources using reverse transcriptase/PCR. The specific method of making the parstatin peptides of the invention is not a limitation of any of the compositions or methods of the invention.

It is to be understood that the parstatin peptides can be of animal, particularly mammalian, for example of human in origin. Parstatin peptides can also be produced synthetically by chemical reaction or by recombinant techniques in conjunction with expression systems. Parstatin peptides can also be produced by enzymatically cleaving different molecules, including parstatin precursors or peptides, containing sequence homology or identity with segments of parstatin to generate peptides having cell activity.

Uses, Methods and Compositions of the Invention

One aspect of the invention relates to an isolated peptide as described above for use as a medicament.

As used herein, "treating, preventing or alleviating," refers to the prophylactic or therapeutic use of the therapeutic agents described herein.

The term "prevention" refers to a reduction in the chance that a subject will suffer from a particular disease or condition. The chance of a subject suffering from a particular disease or condition can be determined by a trained individual, such as a physician. For example, a subject suffering from cardiac ischemia of sufficient duration will likely suffer from reperfusion injury. Prevention can include administration of a therapeutic agent one or more times to a subject, e.g., a long standing prophylactic regimen to prevent aberrant angiogenesis, or a single dose in response to an acute event such as ischemia. Prevention can include a reduction in the level of signs or symptoms observed of the condition and need not completely eliminate all signs or symptoms of disease. Prevention can include a delay in the first onset of signs or symptoms of a disease or condition and need not prevent signs or symptoms from ever being present.

Prevention, amelioration, and or treatment of a disease is typically practiced on a subject first identified as being prone to or suffering from a disease or condition. During and after prevention, amelioration, and treatment of a disease or condition, a subject is typically monitored for signs or symptoms of the disease or condition.

The term "amelioration" refers to a reduction of signs or symptoms of a specific disease or condition. Treatment refers to reduction of signs or symptoms of a disease or condition to reduce or eliminate signs or symptoms of the disease or condition, or to prevent progression of the disease or condition. Prevention, amelioration, and treatment need not be considered separate interventions, but instead can be considered a continuum of therapeutic interventions.

The parstatin peptides disclosed herein have a wide range of therapeutic applications, including one or more of:

treating renal disorders (preferably parstatin 1-41);

protecting from acute renal injury (for example, in ischemia, contrast-induced nephropathy, reperfusion-induced nephropathy) (preferably parstatin 1-41);

inhibiting angiogenesis and treating angiogenesis related disorders (preferably parstatin 1-41);

inhibiting microvessel formation (preferably parstatin 1-41);

inhibiting capillary tube-like formation and migration of endothelial cells (preferably parstatin 1-41);

inhibiting the growth of endothelial cells (preferably parstatin 1-41);

inhibiting DNA synthesis in endothelial cells (preferably parstatin 1-41);

inhibiting signalling through the MAP kinase pathway (preferably parstatin 1-41);

inducing cell apoptosis (preferably parstatin 1-41);

acting as cell penetrating peptides (preferably parstatin 1-41);

suppressing choroidal neovascularisation (preferably parstatin 1-41, parstatin 1-26 and parstatin 24-41, more preferably, parstatin 24-41);

suppressing retinal neovascularisation (preferably parstatin 1-41, parstatin 1-26 and parstatin 24-41, more preferably, parstatin 24-41);

suppressing corneal neovascularisation (preferably parstatin 1-41, parstatin 1-26 and parstatin 24-41, more preferably, parstatin 24-41, parstatin 1-26);

suppressing inflammation (preferably parstatin 1-41, parstatin 1-26 and parstatin 24-41);

reducing VEGF-induced retinal leukostasis (preferably parstatin 1-41, parstatin 1-26 and parstatin 24-41, more preferably, parstatin 24-41, parstatin 1-26);

providing cardioprotection (preferably parstatin 1-26);

attenuating myocardial ischemia reperfusion injury (preferably parstatin 1-41, parstatin 1-26); and causing endothelium dependent coronary vasodilation (preferably parstatin 1-41).

The invention may also include methods of identifying a subject suffering from, suspected of suffering from, or prone to suffering from any of the above-mentioned disorders, including but no limited to angiogenesis-related diseases, ocular neovascularisation and related disease states, ischemia-reperfusion injury and myocardial-related disease states, and acute renal failure and related disease states. The invention may include monitoring these subjects before, during and after treatment for these conditions.

Angiogenesis and Angiogenesis Associated Diseases

The present invention relates to peptides, methods and compositions for preventing, ameliorating, and/or treating angiogenesis related diseases, diseases having an angiogenic component, and processes mediated by undesired and uncontrolled angiogenesis by administrating to a subject with the undesired angiogenesis a composition comprising a parstatin or a substantially purified parstatin or parstatin derivatives or variants in a dosage sufficient to prevent or inhibit angiogenesis.

Thus, one aspect of the invention relates to an isolated peptide or a composition as described above for preventing, ameliorating or treating angiogenesis or an angiogenesis associated disease. For this aspect of the invention, the peptides can be administered alone or in conjunction with other agents for the prevention, amelioration, and/or treatment of angiogenesis related diseases. The other agents can be anti-angiogenic agents. Alternatively, the agents can function to prevent, ameliorate, or treat disease by distinct methods, e.g. anti-proliferative agents for the treatment of cancer or anti-inflammatory agents for the treatment of arthritis.

The peptides or compositions of the invention can be used in the prevention, amelioration and treatment of angiogenesis or angiogenesis associated diseases, and also in the preparation of a medicament for the treatment of angiogenesis or angiogenesis associated-diseases.

The term "angiogenesis" is understood as a physiological process involving the growth of new blood vessels from pre-existing vessels, including vasculogenesis. Vasculogenesis is the term used for spontaneous blood-vessel formation. Angiogenesis is a normal process in growth and development, as well as in wound healing. However, this is also a fundamental step in the transition of tumors from a dormant state to a malignant state. Angiogenesis is promoted by biological signals known as angiogenic growth factors that activate receptors present on endothelial cells present in pre-existing venular blood vessels. The activated endothelial cells begin to release enzymes called proteases that degrade the basement membrane in order to allow endothelial cells to escape from the original (parent) vessel walls. The endothelial cells then proliferate into the surrounding matrix and form solid sprouts or processes connecting neighboring vessels. As sprouts extend toward the source of the angiogenic stimulus, endothelial cells migrate in tandem, using integrin adhesion molecules. These sprouts then form loops to become a full-fledged vessel lumen as cells migrate to the site of angiogenesis. Sprouting occurs at a rate of several millimeters per day, and enables new vessels to grow across gaps in the vasculature.

The invention preferably involves administering a parstatin peptide to a subject suspected of suffering from or suffering from an angiogenesis related disease in an effective therapeutic dose, and preferably observing the subject to detect a decrease in the signs and/or symptoms of the angiogenesis-related disease.

Inhibition of angiogenesis can be defined by a prevention and inhibition of endothelial cell growth, a decrease in endothelial cell migration and/or differentiation and/or vascular tube formation.

In one preferred embodiment, the angiogenesis is aberrant angiogenesis.

As used herein, "angiogenesis associated diseases" includes diseases related to excessive and aberrant angiogenesis. These include, but are not limited to, ocular diseases associated with angiogenesis including, but not limited to retinal and ocular ischemic diseases such as macular degeneration including age-related macular degeneration (AMD), diabetic retinopathy (DR), neovascular glaucoma, ocular neovascular disease, retinopathy of prematurity (ROP) and other developmental disorders, a result of ocular infections, mechanical or chemical injury to the cornea and the eye in general.

In one highly preferred embodiment, the angiogenesis associated disease is an ocular disease. More preferably, the ocular disease is ocular neovascularisation, corneal neovascularisation or ocular inflammation.

The peptides or compositions described herein have therapeutic applications in the prevention, amelioration and treatment of neovascular ocular diseases, corneal neovascularisation and ocular inflammation, and also in the manufacture of a medicament for the treatment of neovascular ocular diseases, corneal neovascularisation and ocular inflammation.

For this embodiment, the peptides of the invention can be administered alone or in conjunction with other agents for the prevention, amelioration, and/or treatment of neovascular ocular diseases or related diseases such as corneal neovascularisation or ocular inflammation. The methods may be conducted by administrating to a human or animal a composition comprising a substantially purified parstatin peptide or parstatin derivatives or variants in a therapeutically effective dose to prevent, treat, or ameliorate one or more symptoms associated with, neovascular ocular diseases and/or to prevent or treat conditions characterized by neovascular ocular diseases.

One aspect of the invention relates to a method of preventing or treating angiogenesis or an angiogenesis associated disease in a subject, said method comprising administering to the subject an isolated peptide or a composition as described above.

The methods of treating or preventing neovascular ocular diseases preferably involve contacting the eye of a subject with the peptide or composition of the invention. The methods may further comprise identifying a subject suffering for or suspected of suffering from an angiogenesis associated disease. The methods may further comprise monitoring a subject suffering for or suspected of suffering from an angiogenesis associated disease.

Angiogenesis associated diseases can also occur outside of the eye and include, but are not limited to chronic inflammation, arthritis, rheumatoid arthritis, osteoarthritis, ulcerative colitis, Crohn's disease, psoriasis, cancer, atherosclerosis, restenosis, intimal hyperplasia, chronic inflammatory diseases such as angiogenesis-related tumor growth and/or metastasis, ischemia/reperfusion injury and pulmonary hypertension. Many ischemia related conditions are associated with insufficient angiogenesis including, but not limited to, coronary artery disease, stroke, and chronic wounds.

The peptides of the invention are also useful for treating, preventing or ameliorating one or more symptoms associated with diseases and conditions characterized by aberrant angiogenic activity and/or endothelial cell dysfunction. Such diseases and conditions include, but not limited, to angiogenesis-related tumor growth and metastasis, ocular neovascular diseases, rheumatoid arthritis, chronic inflammation, ischemia/reperfusion injury, restenosis, pulmonary hypertension, atheroscherosis, intimal hyperplasia. For example, such methods are carried out by contacting a cell or a tissue undergoing pathological angiogenesis with a peptide of the invention.

Myocardial-Related Disease

A further aspect of the invention relates to an isolated peptide or a composition as described above for preventing, ameliorating or treating myocardial-related disease or ischemia-reperfusion injury.

In one preferred embodiment, the isolated peptide or composition is for preventing, ameliorating or treating ischemia-reperfusion injury that is associated with, or arises from, surgery, e.g. ischemic injury related to surgery.

Another aspect of the invention relates to the use of an isolated peptide or a composition as described above in the preparation of a medicament for the treatment of myocardial-related-disease or ischemia-reperfusion injury.

Another aspect of the invention relates to the use of an isolated peptide or a composition as described above as a myocardial protective agent.

A further aspect relates to a method of preventing or treating myocardial-related disease or ischemia-reperfusion injury in a subject, said method comprising administering to the subject an isolated peptide or composition as described above.

The invention further includes compositions and methods of prevention, amelioration, or treatment of ischemia-reperfusion injury including myocardial ischemia-reperfusion injury, comprising using a polypeptide comprising a parstatin peptide or contacting the myocardium with a polypeptide comprising a parstatin peptide.

The methods of prevention or treatment of myocardial-related disease or ischemia-reperfusion injury may comprising administering to the subject a parstatin peptide or composition comprising a parstatin peptide. The administration of the parstatin peptide or composition may involve contacting the heart of a subject with the parstatin peptide or composition. These methods may further comprise identifying a subject suffering for or suspected of suffering from myocardial-related disease or ischemia-reperfusion injury. These methods may further comprise monitoring a subject suffering for or suspected of suffering from myocardial-related disease or ischemia-reperfusion injury.

Endothelial Cell Dysfunction

The present invention also provides methods and compositions for treating diseases and processes mediated by endothelial cell dysfunction and cardiovascular complications by administrating to a subject a composition comprising a substantially purified parstatin peptide or parstatin derivatives or variants in a therapeutically effective dose to prevent, treat, or ameliorate one or more symptoms associated with endothelium dysfunction diseases or angiogenesis, and/or to prevent or treat conditions characterized by cardiovascular complications.

Thus, another aspect of the invention relates to an isolated peptide or a composition as described above for preventing or inhibiting endothelial cell growth.

A further aspect relates to the use of an isolated peptide or a composition as described above in the preparation of a medicament for preventing or inhibiting endothelial cell growth.

Another aspect of the invention relates to a method of inducing cell death and/or apoptosis or cell cycle arrest in mammalian endothelial cells, said method comprising contacting mammalian endothelial cells with an isolated or a composition as described above.

Endothelial cell growth can be defined by any of a number of criteria including, but not limited to, inhibition endothelial cell proliferation, inhibition of DNA synthesis, and inhibition of mitogenic intracellular biochemical pathways as compared to endothelial cells not treated with a parstatin polypeptide. Prevention and inhibition of endothelial cell growth can also include inhibition of angiogenesis which can be defined by a decrease in endothelial cell migration and/or differentiation. The invention includes prevention and/or inhibition of endothelial cell growth in culture or in an animal.

Renal Disorders

The peptides or compositions of the present invention also have therapeutic applications in the prevention, amelioration and treatment of renal disorders, such as ischemia reperfusion injury.

A further aspect of the invention therefore relates to an isolated peptide or a composition as described above for preventing, ameliorating or treating a renal disorder.

In one embodiment, the renal disorder may be renal failure. The renal failure may be chronic renal failure or acute renal failure related to known ischemic events (e.g., surgery). Many types of surgery present the possibility of renal ischemia/reperfusion injury. For example, in urology and nephrology, where renal ischemia-reperfusion injury occurs following several surgical operations.

Administration of the peptides, methods and compositions of the instant invention can prevent renal ischemia-reperfusion injury by ameliorating or eliminating the damage caused by reperfusion injury, for example by administration of the compound prior to the ischemic event. Administration of the compounds of the invention during or after the event can ameliorate or treat the damage caused by ischemia-reperfusion injury.

Renal failure may be caused by a renal injuring or renal failure event including, but not limited to, ischemia-reperfusion injury, kidney transplantation, administration of radiocontrast agents, administration of chemotherapy, contrast-induced nephropathy, sepsis and/or heart failure.

In one preferred embodiment, the renal disorder is a renal ischemia-reperfusion injury or acute renal failure.

A further aspect of the invention relates to the use of an isolated peptide or a composition as described above in the preparation of a medicament for the treatment of a renal disorder.

Another aspect of the invention relates to the use of an isolated peptide according or a composition as described above as a renal protective agent.

Another aspect of the invention relates to a method of preventing or treating a renal disorder in a subject, said method comprising administering to the subject an isolated peptide or a composition as described above.

In one particularly preferred embodiment, the peptide is administered prior to an expected renal injuring event or renal failure event. More preferably, the peptide is administered 1 hour or less, 2 hours or less, 3 hours or less, 4 hours or less, 6 hours or less, 8 hours or less, 12 hours or less, 16 hours or less, 20 hours or less, 24 hours or less, 36 hours or less, or 48 hours or less before an expected renal injuring event or renal failure event.

Inflammation

The peptides or compositions of the present invention also have therapeutic applications in the prevention, amelioration and treatment of inflammatory diseases, In one preferred embodiment the inflammatory disease is ocular inflammation.

In one preferred embodiment the inflammatory disease may be angiogenesis or angiogenesis associated disease.

In another aspect of the invention the inflammatory disease may be corneal neovascularization.

Methods of treating or preventing inflammatory diseases and encompasses and such method diseases preferably involve contacting subject with the peptide or composition of the invention. The methods may further comprise identifying a subject suffering for or suspected of suffering from an inflammatory disease. The methods may further comprise monitoring a subject suffering for or suspected of suffering from an inflammatory disease.

FURTHER DEFINITIONS

The recitation of an embodiment for a variable or aspect herein includes that embodiment as any single embodiment or in combination with any other embodiments or portions thereof.

As used herein, "obtaining" refers to purchase, procure, manufacture, or otherwise come into possession of.

Unless specifically stated or obvious from context, as used herein, the terms "a", "an", and "the" are understood to be singular or plural.

"Providing," refers to obtaining, by for example, buying or making the, e.g., polypeptide, drug, polynucleotide, probe, and the like. The material provided may be made by any known or later developed biochemical or other technique. For example, peptides may be obtained from cultured cells. The cultured cells, for example, may comprise an expression construct comprising a nucleic acid segment encoding the peptide.

The term "subject" includes organisms which are capable of suffering from disease or who could otherwise benefit from the administration of a compound or composition of the invention, such as human and non-human animals. Preferably the subject is a human animal. Preferred human animals include human patients suffering from or prone to suffering from a disease or associated state, as described herein. The term "non-human animals" of the invention includes all vertebrates, e.g., mammals, e.g., rodents, e.g., mice, and non-mammals, such as non-human primates, e.g., sheep, dog, cow, chickens, amphibians, reptiles, etc. Veterinary applications are also encompassed.

Pharmaceutical Compositions

Another aspect relates to a pharmaceutical composition comprising an isolated peptide according to the invention, and a pharmaceutically acceptable diluent, excipient or carrier.

Even though the peptides of the present invention (including their pharmaceutically acceptable salts, esters and pharmaceutically acceptable solvates) can be administered alone, they will generally be administered in admixture with a pharmaceutical carrier, excipient or diluent, particularly for human therapy. The pharmaceutical compositions may be for human or animal usage in human and veterinary medicine.

Examples of such suitable excipients for the various different forms of pharmaceutical compositions described herein may be found in the "Handbook of Pharmaceutical Excipients, $2^{nd}$ Edition, (1994), Edited by A Wade and P J Weller.

Acceptable carriers or diluents for therapeutic use are well known in the pharmaceutical art, and are described, for example, in Remington's Pharmaceutical Sciences, Mack Publishing Co. (A. R. Gennaro edit. 1985).

Examples of suitable carriers include lactose, starch, glucose, methyl cellulose, magnesium stearate, mannitol, sorbitol and the like. Examples of suitable diluents include ethanol, saline, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s), wetting or emulsifying agents, pH buffering substances, and the like.

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

Administration

The pharmaceutical compositions of the present invention may be adapted for oral, rectal, vaginal, parenteral, intramuscular, intraperitoneal, intraarterial, intrathecal, intrabronchial, subcutaneous, intradermal, intravenous, nasal, buccal or sublingual routes of administration.

Formulations suitable for parenteral administration include aqueous and non-aqueous sterile injection solutions which may contain anti-oxidants, buffers, bacteriostatics and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

For oral administration, particular use is made of compressed tablets, pills, tablets, gellules, drops, and capsules.

Other forms of administration comprise solutions or emulsions which may be injected intravenously, intraarterially, intrathecally, subcutaneously, intradermally, intraperitoneally or intramuscularly, and which are prepared from sterile or sterilisable solutions. The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

Compositions may be formulated in unit dosage form, i.e. in the form of discrete portions containing a unit dose, or a multiple or sub-unit of a unit dose.

Preferred unit dosage formulations are those containing a daily dose or unit, daily sub-dose, as herein above recited, or an appropriate fraction thereof, of the administered ingredient. It should be understood that in addition to the ingredients, particularly mentioned above, the formulations of the present invention may include other agents conventional in the art having regard to the type of formulation in question.

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

For treating humans or animals, preferably between approximately 0.5 mg/kilogram to 500 mg/kilogram of the peptide can be administered. A more preferable range is 1 mg/kilogram to 100 mg/kilogram with the most preferable range being from 1 mg/kilogram to 50 mg/kilogram. Depending upon the half-life of the peptide in the particular animal or human, the peptide can be administered between several times per day to once a week. It is to be understood that the present invention has application for both human and veterinary use. The methods of the present invention contemplate single as well as multiple administrations, given either simultaneously or over an extended period of time.

Nucleotides and Nucleic Acid Sequences

The invention also includes nucleic acid sequences that correspond to and code for the bioactive peptide molecules of the invention (i.e. peptides such as SEQ ID NO:1, SEQ ID NO:2 and SEQ ID NO:3), to monoclonal and polyclonal antibodies that bind specifically to such peptides molecules and DNA or RNA oligonucleotides (aptamers) that bind specifically to such peptide molecules.

Thus, another aspect of the invention relates to a nucleic acid sequence encoding a peptide as described above, or a variant, derivative, fragment or homologue thereof.

Preferably, the nucleic acid sequence is at least at least about 70% identity, at least about 80% identity, at least about 90%-identity, at least about 95% identity, preferably at least about 99% identity to the nucleic acid sequence encoding the peptide of the invention.

The invention also encompasses nucleic acid sequences which are complementary to the nucleotide sequences as described above, as well as variants, derivatives, fragments and homologues thereof.

The biologically active peptide molecules, nucleic acid sequences corresponding to the peptides, antibodies and aptamers that bind specifically to the peptides of the present invention are useful for modulating endothelial processes in vivo, and for diagnosing and treating endothelial cell-related diseases, for example by gene therapy. Nucleic acid sequences that correspond to, and code for, parstatin and parstatin analogs can be prepared based upon the knowledge of the amino acid sequence, and the art recognized correspondence between codons, and amino acids.

Nucleic acid sequences are synthesized using automated systems well known in the art.

Either the entire sequence may be synthesized or a series of smaller oligonucleotides are made and subsequently ligated together to yield the full length sequence. Alternatively, the nuclei acid sequence may be derived from a gene bank using oligonucleotides probes based on the N-terminal amino acid sequence and well known techniques for cloning genetic material.

The terms "nucleotide sequence" and "nucleic acid sequence" are used interchangeably throughout herein.

The present invention also includes oligonucleotide aptamers, which can be DNA aptamers or RNA aptamers, specific for the parstatin. The antibodies and aptamers specific for parstatin can be used in diagnostic kits to detect the presence and quantity of parstatin as index of activated PAR1 in vivo which is diagnostic or prognostic for the occurrence or recurrence of cancer or other disease mediated by angiogenesis. Antibodies and aptamers specific for parstatin can also be administered to a human or animal against endogenous parstatin, thereby stimulating angiogenesis in situations where promotion of angiogenesis is desirable, such as in wound healing and non-healing ulcers.

Antibodies

A further aspect relates to antibodies targeted to a peptide according to the invention, or a variant, derivative, fragment or homologue thereof. The antibodies can be polyclonal antibodies or monoclonal antibodies, specific for the parstatin peptides of the invention.

Passive antibody therapy using antibodies that specifically bind to the peptides of the invention can be employed to modulate endothelial-dependent processes such as reproduction, development, and wound healing and tissue repair. Antibodies specific for parstatin, parstatin peptides, and parstatin analogs are made according to techniques and protocols well known in the art. The antibodies are utilized in well know immunoassay formats, such as competitive and non-competitive immunoassays, including ELISA, sandwich immunoassays, and radioimmunoassay (RIAs), to determine the presence or absence of the endothelial proliferation inhibitors of the present invention in body fluids.

Such antibodies can also be used to detect the presence of parstatin in a tissue or sample in vitro or in vivo.

Examples of body fluids include but are not limited to blood, serum, peritoneal fluid, pleural fluid, cerebrospinal fluid, uterine fluid, saliva and mucus.

Oligonucleotides therapy using aptamers that specifically bind parstatin can be employed to modulate endothelial-dependent processes such as reproduction, development, wound healing, and tissue repair. The term "aptamers" refers to nucleic acid molecules (DNA or RNA) having specific binding affinity to molecules through interactions other than classic Watson-Crick base pairing. Aptamers, like peptides generated by phage display or monoclonal antibodies are capable of specifically binding to selected targets and modulating the target's activity or binding interactions, e.g., through binding aptamers may block their target's ability to function. Aptamers specific for parstatin and parstatin analogs are made according to techniques and protocols well known in the art. A typical aptamer is 10-15 kDa in size (20-45 nucleotides), binds its target with nanomolar to subnanomolar affinity, and discriminates against closely related targets.

Kits and Diagnostic Assays

The present invention also includes diagnostic methods and kits for detection and measurement of parstatin peptides in samples (e.g. biological fluids and tissues), and for localization, of parstatin peptides in tissues. The diagnostic method and kit can be in any configuration well known to those of ordinary skill in the art. Kits can further include packaging material and/or instructions for use of the components of the kits. Kits can include antibodies targeted to parstatin peptides, including fragments of parstatin.

In particular, the present invention relates to diagnostic assays and kits for assessing parstatin both in vitro and in vivo, histochemical kits for localization of parstatin in cells, molecular probes to monitor parstatin biosynthesis, and antibodies that are specific for parstatin.

The present invention also includes parstatin peptides and fragments that are labeled isotopically or with other molecules for use in the detection and visualization of parstatin binding sites with state of the art techniques, including, but not limited to, positron emission tomography, autoradiography, flow cytometry, radioreceptor binding assays, and immunohistochemistry. Such peptides and fragments can be conveniently included in kits, optionally containing instructions for use.

The present invention also includes methods for the detection of parstatin peptides in body fluids and tissues for the purpose of diagnosis or prognosis of angiogenesis-mediated diseases such as cancer, cardiovascular diseases, ocular diseases, and arthritis. Antibodies and aptamers that specifically bind to the parstatin can be used in diagnostic methods and kits that are well known to those of ordinary skill in the art to detect or quantify the parstatin in a body fluid or tissue. Results from these tests can be used to diagnose or predict the occurrence or reccurrence of a cancer and other angiogenesis mediated diseases and pathophysiological processes wherein PAR-1 is involved.

The present invention further includes methods for the detection of parstatin binding-sites and receptors in cells and tissues, in vitro and in vivo. The present invention also includes methods of treating or preventing diseases and processes including, but not limited to, arthritis, diabetic retinopathy and tumors by stimulating the production of parstatin, and/or by administrating substantially purified parstatin polypeptides, parstatin agonists, or parstatin antagonists.

The peptides, nucleic acid sequences, antibodies, and aptamers of the present invention are useful for diagnosing and treating endothelial cell-related diseases and disorders. A particularly important endothelial cell process is angiogenesis, the formation of blood vessels, as discussed above. Angiogenesis-related diseases may be diagnosed and treated using the endothelial cell proliferation inhibiting proteins of the present invention, i.e., parstatin peptides and analogs. Angiogenesis-related diseases include, but are not limited to, angiogenesis-dependent cancer (solid tumors, blood born tumors such as leukemias, ands tumor metastases; benign tumors, for example hemangiomas, acoustic neuromas, neurofibromas), rheumatoid arthritis, psoriasis, ocular angiogenic diseases (diabetic retinopathy, petinopathy of prematurity, macular degeneration, corneal graft rejection, neovascular glaucoma, retrolental fibroplasias), myocardial angiogenesis, plaque neovascularization, and wound granulation.

The parstatin endothelial cell proliferation inhibiting peptides of the present invention are useful in the treatment of disease of excessive or abnormal stimulation of endothelial cells. These diseases include, but are not limited to, intestinal adhesions, atherosclerosis, scleroderma and hypertrophic scars, i.e., keloids. They are also useful in the treatment of diseases that have angiogenesis as a pathologic consequence such as cat scratch disease (*Rochele minalia quintosa*) and ulcers (*Helobacter pylori*).

Conversely, blockade of parstatin receptors with parstatin analogs which act as receptor antagonists as well as blockade of parstatin molecules with antibodies or aptamers, which specifically bind and inhibit parstatin biological activity, may promote endothelialization and vascularization. Such effects may be desirable in situations of inadequate vascularization of the uterine endometrium and associated infertility, wound repair, healing of cuts and incisions, treatment of vascular problems in diabetics, especially retinal and peripheral vessel, peripheral angiopathies, especially peripheral ischemic vascular disorders, promotion of vascularization in transplanted tissue including muscle and skin, promotion of vascularization of cardiac muscle especially following transplantation of a heart or heart tissue and after bypass surgery, promotion of vascularization of solid and relatively avascular tumors for enhanced cytotoxin delivery, and enhancement of blood flow to the nervous system, including but not limited to the cerebral cortex and spinal cord.

The amino acid sequence of the peptide is known and the parstatin can be synthesized by technique well known in the art, as exemplified by "Solid Phase Peptide Synthesis: A Practical Approach" E. Atherton and R. C. Sheppard, IRL Press, Oxford, England. Similarly, multiple fragments can be synthesized which are subsequently linked together to form larger fragments. These synthesis peptide fragments can also be made with amino acid substitutions at specific locations in order to test for agonistic and antagonistic activity in vitro and in vivo. Peptide fragments that possess high affinity binding to tissues can be used to isolate the parstatin receptor on affinity columns. Isolation and purification of the parstatin receptor is a fundamental step towards elucidating the mechanism of action of parstatin. This facilitates development of drugs to modulate the activity of the parstatin receptor, the final pathway to biological activity. Isolation of the receptor enables the construction of nucleotide probes to monitor the location and synthesis of the receptor, using in situ and solution hybridization technology.

The synthetic peptide fragments of parstatin have a variety of uses. The peptide that binds to the parstatin receptor with high specificity and avidity can be detectably labeled, e.g., radiolabeled or fluorescently labeled, and employed for visualization and quantitation of binding sites using known techniques, such as membrane binding techniques. This application provides important diagnosis and research tools. Knowledge of the binding properties of the parstatin receptor facilitates investigation of the transduction mechanisms linked to the receptor. In addition, labeling these peptides with short lived isotopes enables visualization of receptor binding sites in vivo using positron emission tomography or other modern radiographic techniques in order to locate tumors or cardiovascular complications with parstatin binding sites.

Systematic substitution of amino acids within parstatin or its fragments yields high affinity peptide agonists and antagonists to the parstatin receptor that enhance or diminish parstatin binding to its receptor. Such agonists are used to suppress the growth of micrometastases, thereby limiting the spread of cancer. Antagonists to parstatin are applied in situations of inadequate vascularization, to block the inhibitory effects of parstatin and possibly promote angiogenesis. This treatment may have therapeutic effects to promote wound healing in diabetics.

Combinations

Therapeutic agents of the instant invention, e.g., parstatin peptides, can be co-administered with other drugs or therapeutic agents. "Co-administering," as used herein refers to the administration with another agent, either at the same time, in the same composition, at alternating times, in separate compositions, or combinations thereof.

Thus, the peptides and compositions of the present invention can be used alone or in combination with other compositions and procedures for the treatment of diseases. For example, a tumor may be treated conventionally with surgery, radiation, and/or chemotherapy combined with parstatin and then parstatin may be subsequently administered to the patient to extend the dormancy of micrometastases and/or to stabilize any residual primary tumor.

Devices

Cytotoxic and antiangiogenic compounds may also be used in medical devices, e.g. as drug eluting stents to prevent restenosis and intimal hyperplasia. For example, a vascular endoprosthetic device, e.g., a stent, may include the peptides of the invention. The composition is impregnated in the device or the device is coated with the peptide of the invention.

The peptides and peptides fragments with the parstatin activity described above can be provided as isolated and substantially purified peptides and peptides fragments in pharmaceutically acceptable formulations using formulation methods known to those of ordinary skill in the art. These formulations can be administered by standard routes. In general, the combinations may be administered by the topical, transdermal, intraperitoneal, intracranial, intracerebroventricular, intracerebral; intravaginal, intrauterine, oral, rectal, or parenteral (e.g., intravenous, intraspinal, subcutaneous, or intramuscular) route. In addition, the parstatin may be incorporated into biodegradable polymers allowing for sustained release of compound, the polymers being implanted in the vicinity of where drug delivery is desired, for example, at the site of a tumor or implanted so that the parstatin is slowly released systemically. Osmotic minipumps may also be used to provide controlled delivery of high concentrations of peptides through cannulae to the site of interest, e.g., directly into a metastatic growth or into the vascular supply to that tumor.

The invention is further illustrated by the following non-limiting examples.

EXAMPLES

Example 1

Parstatin Peptides Synthesis and Compositions

Parstatin peptides used in our assays were synthesized in the core peptide facility of Peptide Specialty Laboratories GmbH (Heidelberg, Germany) or Bio-Synthesis Inc., (Lewisville, Tex.) or at the Protein and Nucleic Acid Shared Facility at the Medical College of Wisconsin. Synthesized peptides were purified by HPLC technology, characterized by mass spectrometry technology and sequenced. The synthesized peptides were as follows:

1. Human parstatin, parstatin (1-41), which corresponds to 1-41-amino acids cleaved N-terminal fragment of human PAR1.

```
Sequence:
                                  SEQ ID NO: 1
MGPRRLLLVAACFSLCGPLLSARTRARRPESKATNATLDPR.
(molecular weight of 4468 Da).
```

2. Mouse parstatin, which corresponds to 1-41-amino acids cleaved N-terminal fragment of mouse PAR-1.

```
Sequence:
                                  SEQ ID NO: 2
MGPRRLLIVALGLSLCGPLLSSRVPMSQPESERTDATVNPR.
(molecular weight of 4420 Da).
```

3. Scrambled human parstatin, which contains to randomly rearranging the amino acid sequence to human parstatin.

```
Sequence:
                                  SEQ ID NO: 3
LRTNASLLVPFLTARAKSSGTREAADPPRLMCLRPLARRCG.
(molecular weight of 4468 Da).
```

4. Human parstatin 24-41 fragment, parstatin (24-41), which corresponds to 24-41 (18 amino acids) of amino acid sequence of human parstatin.

```
Sequence:
                                  SEQ ID NO: 4
TRARRPESKATNATLDPR.
(molecular weight of 2041 Da).
```

5. Human parstatin 1-26 fragment, parstatin (1-26), which corresponds to 1-26 amino acid sequence of human parstatin.

```
Sequence:
                                  SEQ ID NO: 9
MGPRRLLLVAACFSLCGPLLSARTRA.
(molecular weight of 2772 Da).
```

6. Modulated human parstatin, mod-parstatin, which contains scrambled the 24 to 41 amino acids of human parstatin.

```
Sequence:
                                  SEQ ID NO: 10
MGPRRLLLVAACFSLCGPLL-SARALTRSAPTPRDRANKETR.
(molecular weight of 4468 Da).
```

7. Human parstatin (1-41)-FITC, parstatin (1-41)-FITC, which fluorescein isothiocyanate (FITC) is conjugated to human parstatin.

```
Sequence:
                                  (SEQ ID NO: 11)
FITC-Ahx-MGPRRLLLVAACFSLCGPLLSARTRARRPESKATNATLDPR.
```

8. Human parstatin (24-41)-FITC, parstatin (24-41)-FITC, which fluorescein isothiocyanate (FITC) is conjugated to human parstatin (24-41) fragment.

```
Sequence:
                                  (SEQ ID NO: 12)
TRARRPESKATNATLDPRK-FITC.
```

9. Modulated human parstatin-FITC, which fluorescein isothiocyanate (FITC) is conjugated to modulated human parstatin.

```
Sequence:
                                  (SEQ ID NO: 13)
FITC-Ahx-MGPRRLLLVAACFSLCGPLLSARALTRSAPTPRDRANKETR.
```

Example 2

Parstatin (1-41) Inhibits Angiogenesis In Vivo

The in vivo chick chorioallontoic membrane (CAM) angiogenesis model was used to evaluate the effect of parstatin (1-41) in angiogenesis. On incubation day 9 of fertilized chicken eggs, an O-ring (1 cm$^2$) was placed on the surface of the CAM and the vehicle or the indicated substances were placed inside this restricted area. After 48 h, CAMs were fixed in saline-buffered formalin, photographed, and analyzed using the Scion Image software (Scion Image Release Beta 4.0.2 software; Scion Corporation, Frederick, Md.). Image analysis was performed on at least 18 eggs for each group. Vessel number and length were evaluated by pixel counting, and the results expressed as mean percentage of control ±SE. Statistical analyses were performed using a Student's t test.

Figure 1:
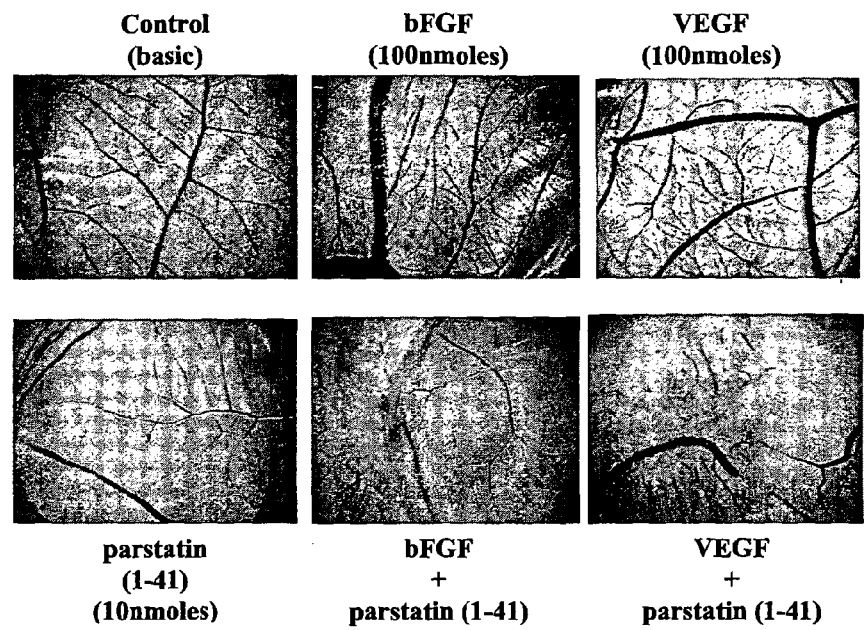
FIG. 1. Parstatin (1-41) inhibits angiogenesis in vivo in chick embryo CAM model. A, CAMs were exposed to either vehicle (PBS) or human parstatin (1-41) (1-10 nmoles, parst 1, parst 10) or bFGF (100 nmoles) or VEGF (100 nmoles) or the indicated combinations for 48 h. Representative photomicrographs are shown. B, The total length of vessel network was evaluated in pixels, using image analysis software. Data are expressed as mean percentage change of control (0%) ±SE. At least 18 eggs were used for each group (n=18-24). Statistical analysis was performed versus control or between indicated groups. $*p<0.05$, $**p<0.01$.
Figure 1:
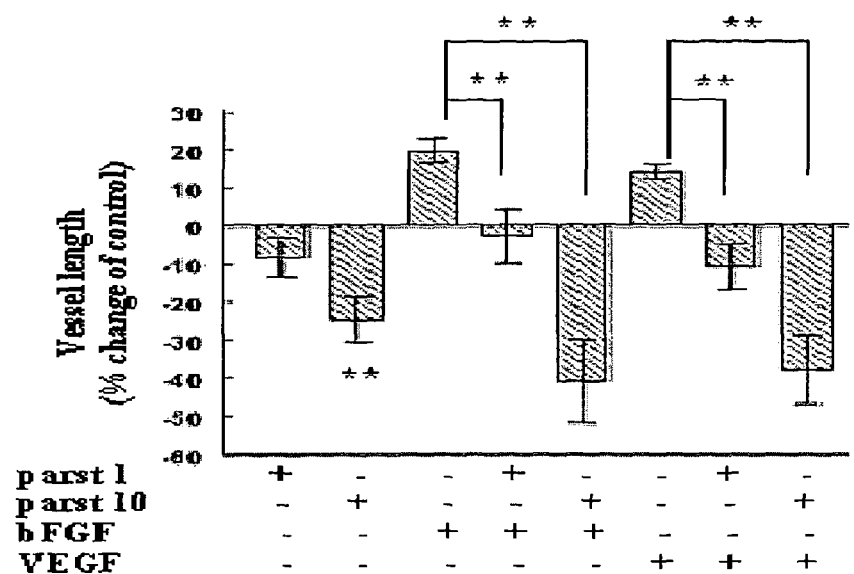

Parstatin (1-41) was very potent anti-angiogenic substance (FIG. 1A). The application of human parstatin on CAM of chick embryo, at concentration of 10 nmoles, resulted in a significant inhibition of the basal level of angiogenesis that occurs in CAMs. This inhibitory effect was dose-dependent (FIG. 1B) and not toxic for the chick embryo, at concentrations up to 300 nmoles. Interestingly, the anti-angiogenic effect of parstatin was more pronounced when angiogenesis was stimulated by growth factors such as bFGF or VEGF. The application of scrambled parstatin, at concentration similar to that of human (10 nmoles), did not cause any significant effect. These results demonstrate the sequence specific, dose specific effect of human parstatin peptides on vascular growth in an accepted in vivo angiogenesis model.

Example 3

Parstatin (1-41) Inhibits Angiogenesis in Rat Aortic Ring Assay

The recognition that angiogenesis in vivo involves not only endothelial cells but also their surrounding cells, has led to development of angiogenic assays using organ culture methods. Of these, the rat aortic ring assay has become the most widely used.

Freshly cut aortic rings obtained from 5- to 10-week-old Fischer 344 male rats were embedded in collagen gels and transferred to 16-mm wells (4-well NUNC dishes) each containing 115 ml serum-free endothelial basal medium (EBM, Clonetics Corporation) alone or supplemented with VEGF or bFGF. The angiogenic response of aortic cultures was measured in the live cultures by counting the number of neovessels over time using art accepted methods. Mean number of microvessels ±SE was determined. Statistical analysis was performed using unpaired two-tailed t-test.

Figure 2:
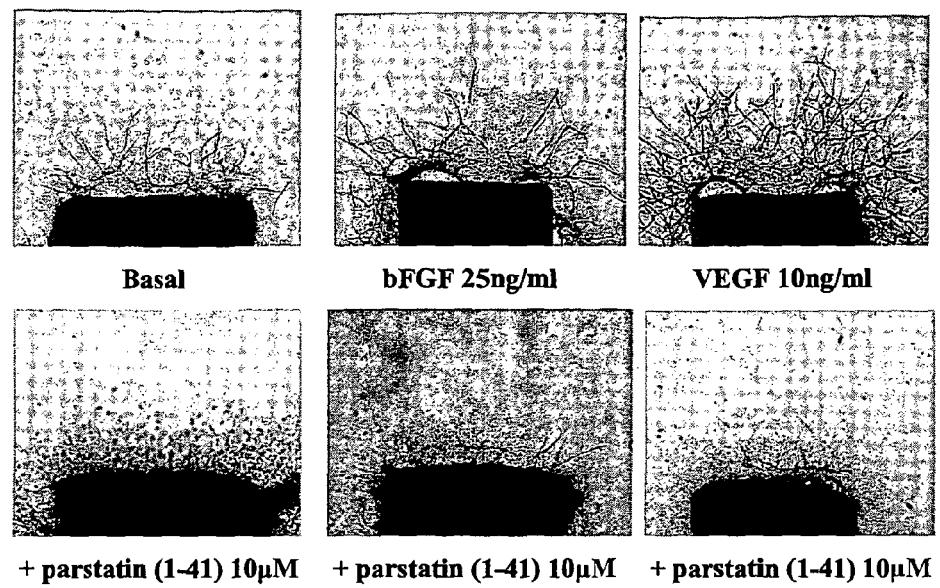
FIG. 2. Parstatin (1-41) inhibits angiogenesis in ex-vivo rat aortic ring model. A, Collagen embedded freshly cut rat aortic rings were incubated in either basal medium or in medium supplemented with VEGF (10 ng/ml) or bFGF (25 ng/ml) for 7 days. Cultures were treated with vehicle alone or with human parstatin (1-41) at concentrations ranging from 1 to 10 µM (parst 1, parst 3, parst 10). Representative photomicrographs are shown. B, Angiogenesis was estimated by counting the number of microvessels at the end of experiments. Results are expressed as mean number of microvessels±SE (n=6 rings/group). Statistical analysis was performed versus controls. $**p<0.01$.
Figure 2:
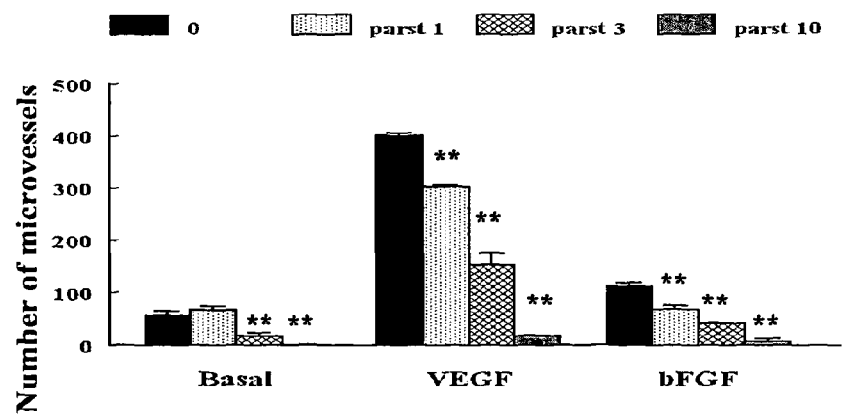

Parstatin (1-41) inhibited microvessel formation (FIG. 2A). This inhibitory effect was in a dose dependent manner, with complete inhibition at a 10 µM, and was also evident either in basal conditions or in VEGF- or bFGF-induced angiogenesis (FIG. 2B). Again, the ability of parstatin to function across species is noted. Human parstatin (1-41) effectively inhibits angiogenesis in rat tissue in a non-species specific, dose dependent manner.

Example 4

Parstatin (1-41) Inhibits Capillary Tube-Like Formation and Migration of Primary Human Endothelial Cells Primary human umbilical vein endothelial cells (HUVEC cells) were obtained from freshly delivered umbilical cords from caesarean births and were grown in M199 medium with 20% fetal bovine serum (FBS) supplemented with endothelial cell growth supplement and heparin. One of the most specific tests for angiogenesis is the measurement of the ability of endothelial cells to form capillary-like structures (i.e., tube formation). Tube formation is a multi-step process involving cell adhesion, migration and differentiation. Tube formation can be enhanced by use of Matrigel or fibrin clots to coat plastic culture dishes and it is an accepted model of angiogenesis.

Matrigel™ (Becton Dickinson Labware, N.J., USA) is a mixture of basement membrane components extracted from the Englebreth-Holm-Swarm tumor. It has been demonstrated that endothelial cells attach, migrate, and assemble to form tube-like structure resembling capillaries within 18 hours of plating. Matrigel™ (250 µl) was added to each well of a 24-well plate and allowed to polymerize. A suspension of 40,000 HUVEC cells in M199 medium containing 5% FBS was added into each well coated with Matrigel™.

Cells were treated with increasing concentrations of human parstatin (1-41), scrambled parstatin, or parstatin (24-41) fragment. After 18 hours of incubation, the medium was removed, and the cells were fixed and stained, and tube-like structures were quantitated.

Figure 3:
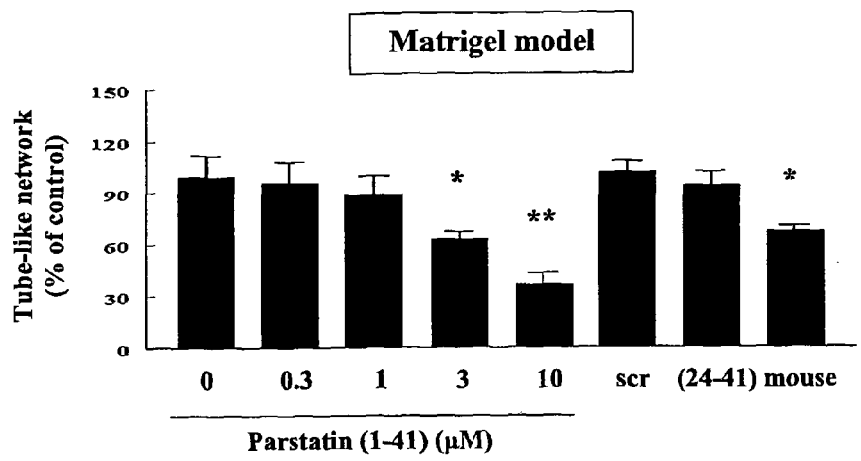
FIG. 3. Parstatin (1-41) inhibits angiogenesis-related in vitro models. A, HUVECs were plated onto Matrigel layers with medium containing 5% FBS in the absence or in the presence of indicated concentrations of parstatin (1-41) or mouse parstatin (mouse, 10 µM) or parstatin (24-41) (24-41, 10 µM) or scrambled parstatin (scr, 10 µM). Capillary-like networks were quantitated after 18 h. B, HUVECs were cultured between two fibrin layers in medium containing VEGF/bFGF, (25 ng/ml each) in the absence or in the presence of indicated concentrations of parstatin (1-41) or mouse parstatin (mouse, 10 µM) or parstatin (24-41) (24-41, 10 µM) or scrambled parstatin (scr, 10 µM). The formed capillary-like network was quantitated after 24 h. C, HUVECs were allowed to migrate for 6 h toward 5% 'FBS' in the absence (control) or in the presence of indicated concentrations of parstatin (1-41) or mouse parstatin (mouse, 10 µM) or parstatin (24-41) (24-41, 10 µM) or scrambled parstatin (scr, 10 µM). Tube formation (A, B) was quantitated in triplicates using a computerized digital image analyzer. Each experiment was repeated at least three times. Results are given as mean percentage change of control (100%)±SE. Statistical analysis was performed versus controls. Cell migration experiments (C) were run in triplicate and repeated at least three times. The results are expressed as mean number of migrated cells per six high-magnification microscopic fields±SE. Statistical analysis was performed versus controls. $*p<0.05$, $**p<0.01$.
Figure 3:
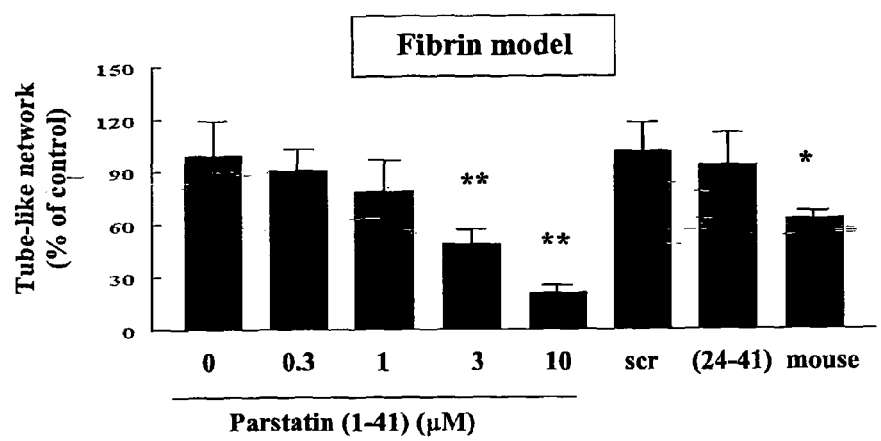
Figure 3:
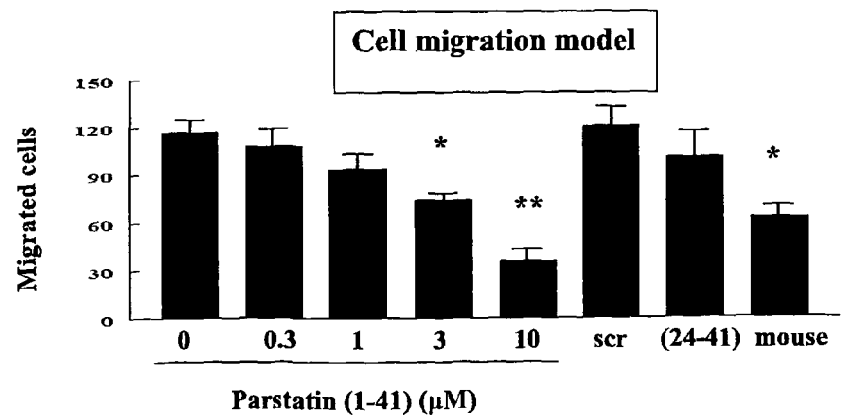

When parstatin (1-41) was tested in Matrigel™ model, it exhibited a significant inhibitory effect on the rate and extent of tube formation (FIG. 3A). At concentrations ranging from 0.3 to 10 µM, parstatin (1-41) caused a dose-dependent inhibition of tube formation by endothelial cells plated on medium containing 5% serum. Mouse parstatin was effective in inhibiting tube formation by human cells.

The ability of endothelial cells to form three-dimensional structures was analyzed using a Fibrin gel in vitro angiogenesis assay kit (Chemicon International Inc. Temecula, Calif.). Fibrin gels were formed in 48-well plates by mixing fibrinogen and thrombin solutions, according to manufacturer instructions. Cells (40,000 cells/well) were then added and cultured in medium containing 2% FBS for 18 h. After the addition of a second layer of fibrin gel, endothelial cells sandwiched within fibrin gels were cultured in serum-free medium containing 0.5% bovine serum albumin (BSA) and the combination of VEGF/bFGF for 24 h. Where indicated, parstatin (1-41) or other indicated peptides were added. Capillary-like network was photographed and measured.

Similar results were evident in fibrin in vitro angiogenesis model as in the tube formation model, where endothelial cells were cultured in a sandwich mode between two fibrin gels, and formed capillary-like tubes in 3 dimensions. The total capillary tube length induced by VEGF and bFGF was significantly reduced by parstatin (1-41) (FIG. 3B).

Control scrambled parstatin and parstatin (24-41) did not affect the ability of endothelial cells to form capillary-like networks in either model (FIGS. 3A and B). Exposure of endothelial cells to mouse parstatin (1-41) resulted in a less pronounced, but still significant, inhibitory effect (FIGS. 3A and B). These data further demonstrate the effectiveness of parstatin (1-41) as anti-angiogenic agents both within and across species.

HUVEC cell migration was assessed using a modified Boyden's chamber assay, i.e., in Transwell cell culture chambers (Corning Life Sciences, Acton, Mass.). Briefly, polycarbonate filters with 8 µm pores were used to separate the upper and the lower chambers. Cells were added to the upper compartment at a density of 10,000 cells/100 µl in serum-free medium containing 0.5% BSA and incubated for 6 h. Directional migration (chemotaxis) in the lower chamber was induced by addition of medium containing 5% FBS to the lower chamber. Where indicated parstatin or other peptides were added to lower chamber.

Cells on the filters were fixed and stained. The non-migrated cells (cells in upper surface) were removed by wiping with cotton swabs. The cells on the lower surface were counted manually under microscope in six predetermined fields. Parstatin (1-41) attenuated chemotactic cell migration through microporous membrane in response to serum (FIG. 3C). When human parstatin was combined with 5% FBS, the number of migrated cells was reduced in concentration-dependent manner. Again, scrambled parstatin and parstatin (24-41) were without effect. Mouse parstatin (1-41) caused a significant inhibitory effect, but to a lower extent as compared to human parstatin (1-41). These data demonstrate that parstatin (1-41) can have an anti-angiogenic effect by decreasing cell migration, a required step in angiogenesis.

Example 5

Parstatin (1-41) Inhibits Growth of Endothelial Cells

Cell proliferation was evaluated using a 3-(4,5-dimethyl-2-yl)-2,5-diphenyltetrazolium bromide (MTT, Sigma-Aldrich, St. Louis, Mo.) assay. Endothelial cells (10,000/well) were seeded in 24-well tissue culture plates and incubated with growth medium for 24 h. Cells were then treated with the vehicle or the indicated peptides in medium containing 5% FBS for 1 to 3 days. After 24, 48, or 72 hours, MTT solution (5 mg/ml) was added to each well and incubated for 3 h at 37° C. The blue formazan crystals were solubilized by addition of DMSO and absorbance at 450 nm was recorded using a 96-well plate reader.

Figure 4:
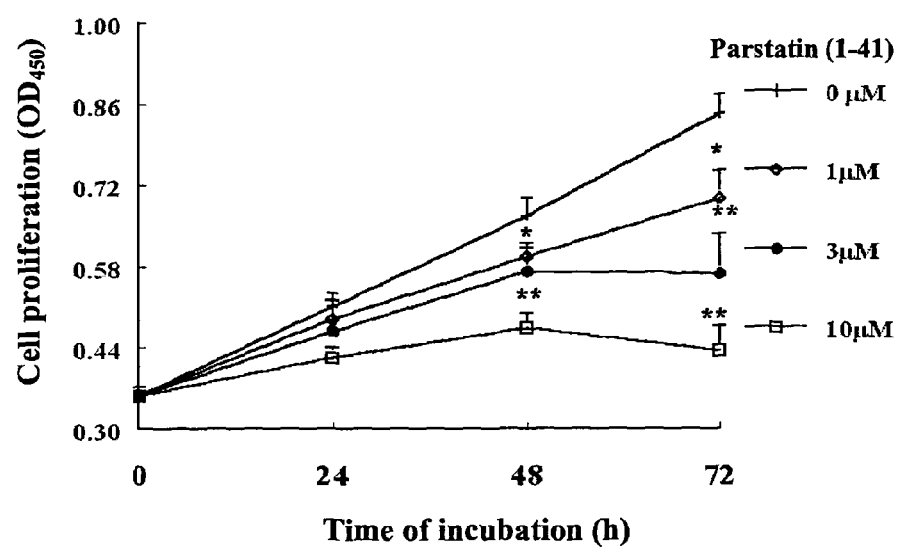
FIG. 4. Parstatin (1-41) inhibits growth of endothelial cells. HUVECs were incubated in medium containing 5% FBS in the absence (control) or in the presence of human parstatin (1-41) at concentrations ranging from 1 to 10 µM. Estimation of cell growth (proliferation) was performed after 24, 48, or 72 h. Experiments were run in triplicate and repeated at least three times. Results are expressed as mean of optical densities at 450 nm ($OD_{450}$)±SE. Statistical analysis was performed versus controls. $*p<0.05$, $**p<0.01$.

Endothelial cell number doubled every 18 to 26 h over the 72-h period. In the presence of parstatin (1-41), the rate of endothelial cell growth was significantly decreased (FIG. 4). HUVEC cell proliferation was essentially blocked by parstatin (1-41) at 10 µM. This inhibitory effect of parstatin was dose-dependent with half-maximal inhibitory concentration at approximately 3 µM.

Similar results were also obtained when cell growth was stimulated by VEGF or bFGF with half-maximal inhibitory concentration of 1 µM for parstatin. Mouse parstatin was less effective inhibiting cell proliferation with half-maximal concentration at 20 µM, whereas scrambled parstatin and parstatin (24-41) were without effect at concentration of 10 µM. These data demonstrate that parstatin (1-41) decreases the rate of endothelial cell proliferation both within and across species.

Example 6

Parstatin (1-41) Inhibits DNA Synthesis in Endothelial Cells

The ability of parstatin (1-41) to inhibit DNA synthesis of endothelial cells was assessed in thymidine incorporation assays. HUVEC cells were grown until 60-80% confluent in 24-well plates. Cells were treated with indicated peptides in serum-free medium containing either 0.5% BSA, or VEGF, or bFGF, or medium containing 5% FBS, or epidermal growth factor (EGF), or heparin-binging EGF (HB-EGF) for 18 hours. All cells were pulsed with 0.5 µCi/ml [3H]-thymidine (ICN Biomedicals Inc., Irvine Calif.) for additional 6 h. Radioactivity incorporated into DNA was determined in liquid scintillation counter.

Figure 5:
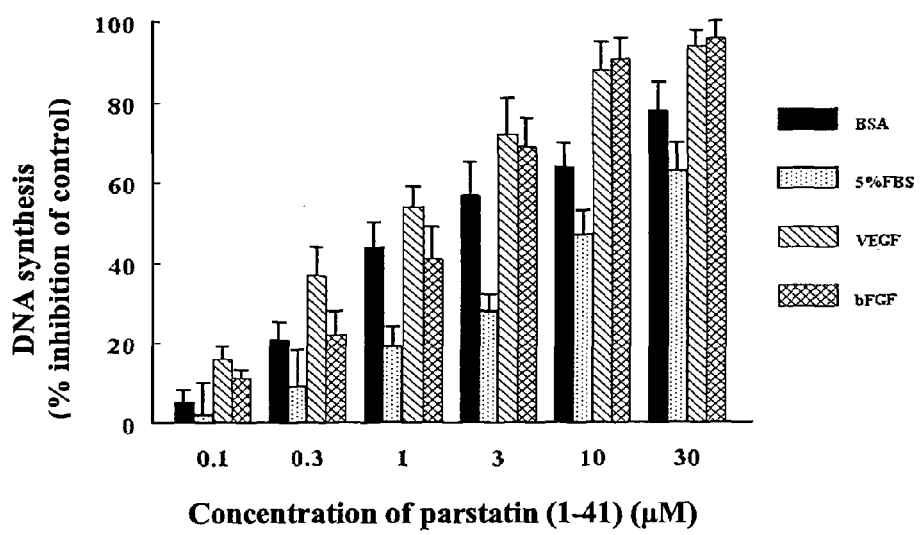
FIG. 5. Parstatin (1-41) inhibits DNA synthesis in endothelial cells. A, HUVECs were incubated in medium containing either 0.5% BSA or 5% FBS or VEGF (10 ng/ml) or bFGF (5 ng/ml) in the absence (control) or in the presence of increasing concentrations of human parstatin (1-41) for 18 h. B, HUVECs were incubated in medium containing either 0.5% BSA (C, control) or bFGF (5 ng/ml) or EGF (10 ng/ml) or HB-EGF (HB, 50 ng/ml) in the absence or in the presence of human parstatin (1-41) (10 µM) for 18 h. All cells were pulsed with [$^3$H]thymidine for an additional 6 h. All experiments were run in triplicate and were repeated at least three times Results are expressed as mean±S.E. of DPM per well and presented (A) as percentage inhibition of control (0%) or (B) as percentage change of control (100%). Statistical analysis was performed between indicated groups. ns, non significant; $**p<0.01$.
Figure 5:
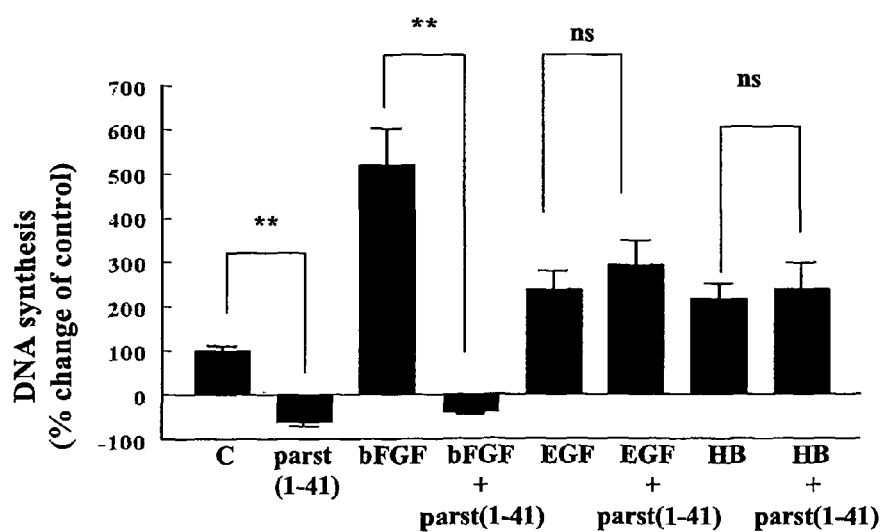

Parstatin (1-41) reduced DNA synthesis in HUVEC cells in a dose-dependent manner, with the inhibitory effect on bFGF- or VEGF-stimulated DNA synthesis being more substantial than that of serum (FIG. 5A). These data demonstrate more potent activity of parstatin (1-41) on dividing cells rather than quiescent cells.

When DNA synthesis experiments were repeated with cells that were in quiescent state (100% confluent), the inhibitory effect of parstatin (1-41) was less pronounced (21.6%±7.4 inhibition by 10 µM parstatin (1-41) in 5% FBS versus 47.3±6.1 on fast-growing cells), indicating a more substantial inhibitory effect for parstatin (1-41) on stimulated endothelial cells.

The continuous presence of parstatin (1-41) in cell culture was not necessary, since DNA synthesis inhibition was also evident after short exposure of cells to parstatin (1-41). Even at the earlier time studied of 30 min exposure, the inhibition of VEGF-induced DNA synthesis was 70% of the maximum (exposure for 24 h) and did not increase further after 1 h exposure to parstatin (1-41). These data demonstrate that a single dose of parstatin (1-41) can have a sustained effect.

It is interesting that the DNA synthesis-inhibitory effect of parstatin (1-41) was specific for bFGF and VEGF because parstatin (1-41) did not have any effect on EGF or HB-EGF-induced DNA synthesis (FIG. 5B).

As in cell proliferation experiments, mouse parstatin exhibited a significant, but less effective inhibitory effect. Scrambled parstatin and parstatin (24-41) did not cause any significant effect at concentration of 10 µM, demonstrating specificity of the parstatin (1-41) as anti-angiogenic agents.

Example 7

Parstatin (141) Inhibits Signaling Through the MAP Kinase Pathway

The MAPK (Erk1/2, p42/44) cascade mediates mitogenesis. Cell cycle progression has been shown to depend on sustained activation of the Erk signal transduction pathway. HUVEC cells were cultured in 35 mm tissue culture dishes. After reaching 80% confluency, cells were growth factor-starved and subsequently stimulated for 10 min with vehicle or indicated agents. In combination experiments, cells were pretreated with parstatin or other peptides for 10 to 60 min.

Attached cells were lysed with Laenmli sample buffer, resolved in 10% SDS-PAGE, and transferred to nitrocellulose membranes. Membranes were incubated with primary antibodies against phospho p42/44 mitogen-activated protein kinases (p-Erk1/2, New England Biolabs, UK) and p42/44 Erk1/2 (t-Erk1/2, New England Biolabs, UK). Membranes were then probed with secondary antibodies horseradish peroxidase-conjugated, and proteins were visualized by chemiluminescent detection.

Figure 6:
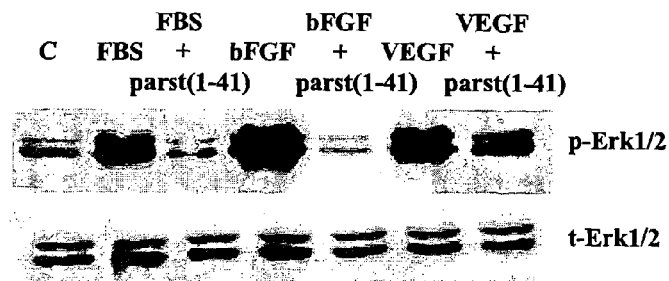
FIG. 6. Parstatin (1-41) inhibits signaling through the MAP kinase pathway. A, Serum-starved HUVECs were pretreated with parstatin (1-41) (10 µM) for 1 h and then stimulated with 5% FBS or bFGF (5 ng/ml) or VEGF (10 ng/ml) for 10 min. B, HUVECs were pretreated with indicated concentrations of parstatin (1-41) for 1 h and then stimulated with bFGF (5 ng/ml) for 10 min. C, HUVECs were pretreated with parstatin (1-41) (10 µM) for indicated time periods or with scramble parstatin (Scr, 10 µM) or mouse parstatin (mouse, 10 µM) for 1 h and then stimulated with bFGF (5 ng/ml) for 10 min. D, HUVECs were pretreated with parstatin (1-41) (10 µM) for 1 h and then stimulated with bFGF (5 ng/ml) or washed (removal of parstatin (1-41)) and incubated in fresh medium for addition indicated times and stimulated with bFGF. E, Serum-starved HUVECs were pretreated with parstatin (1-41) (10 µM) for 1 h and then stimulated with bFGF (5 ng/ml) or EGF (10 ng/ml) or HB-EGF (50 ng/ml) for 10 min. Cell lysates were probed with antiphospho Erk1/2-specific antibody. To determine total protein level, membranes were probed with Erk1/2 antibody. Experiments were repeated at least three times. Representative membrane blots are shown.
Figure 6:
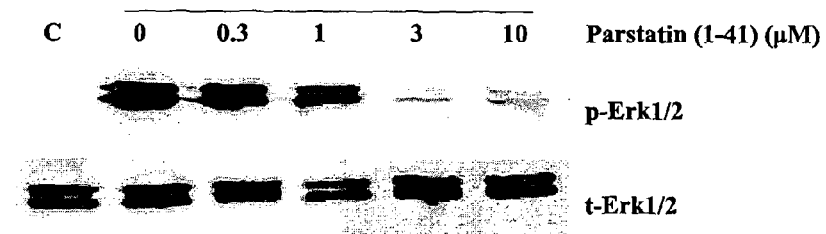
Figure 6:
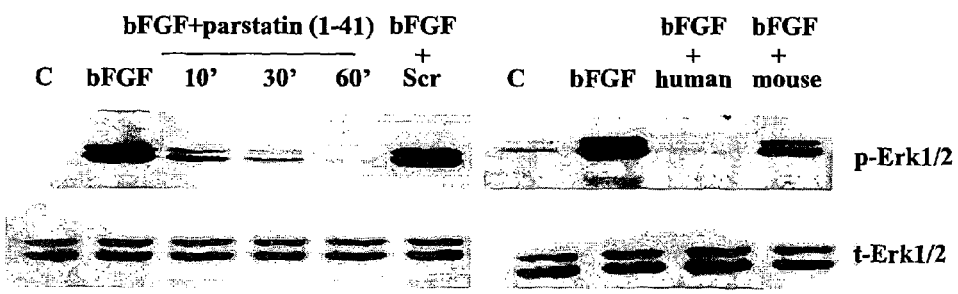
Figure 6:
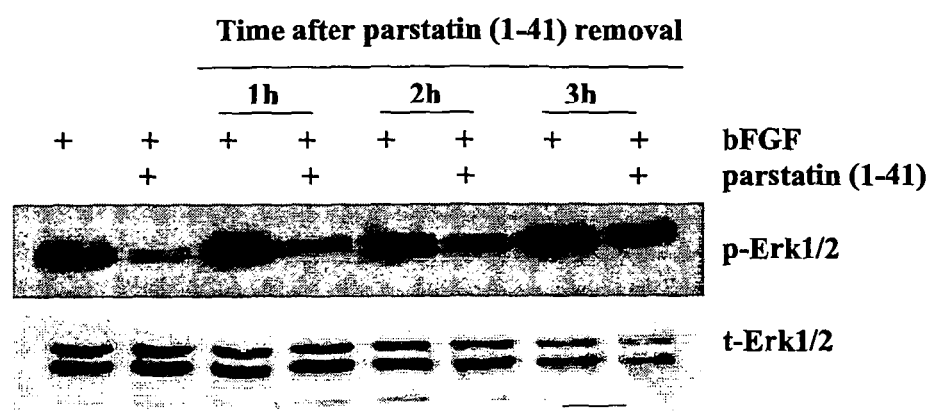
Figure 6:
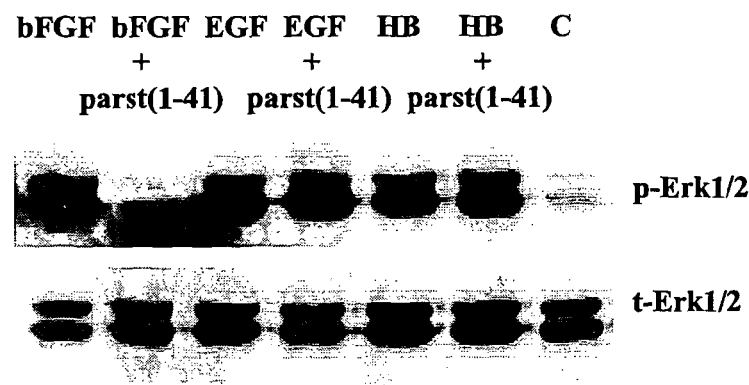

Pretreatment of endothelial cells with parstatin (1-41) for 1 h inhibited the activation of Erk1/2 stimulated either by FBS, bFGF, or VEGF (FIG. 6A). The inhibitory effect was concentration-dependent (FIG. 6B). Parstatin (1-41) essentially blocked the bFGF-induced Erk1/2 phosphorylation levels from a concentration of 3 µM parstatin (1-41). This inhibitory effect was observed at the shortest exposure times (FIG. 6C).

For example, at 10 min, the inhibition of Erk1/2 activation was about 50% of the maximum, indicating a time-dependent effect of parstatin (1-41).

The blockage of Erk1/2 phosphorylation by parstatin (1-41) was found to be almost completely reversible (FIG. 6D). HUVEC cells exposed to human parstatin (1-41) for 1 h, then washed free of parstatin (1-41), and subsequently incubated for further 1 to 3 hours in fresh medium, regained the ability to respond in bFGF and to stimulate the phosphorylation of Erk1/2. As expected scrambled parstatin did not alter the Erk1/2 activation and mouse parstatin had a less pronounced effect as compared to parstatin (1-41) at similar concentrations (FIG. 6C).

Interestingly, the growth inhibitory effect of parstatin (1-41) was specific for bFGF or VEGF, since parstatin did not have any effect on EGF- or HB-EGF-induced Erk1/2 activation (FIG. 6E). These results may provide insight to the mechanism of action of parstatin (1-41) in the inhibition of cell proliferation and migration.

Example 8

Parstatin (1-41)-Mediated Inhibition of Endothelial Cell Growth is Associated with Induction of Cell Apoptosis as Demonstrated by Flow Cytometry and Cell Staining Flow-cytometric cell cycle analysis was performed to determine whether the inhibitory effect of parstatin on cell growth was a reflection of cytostatic or cytotoxic effects due to cell cycle arrest and apoptosis. HUVEC cells grown in 100 mm tissue culture plates to approximately 80% confluence, were: treated in absence or in presence of parstatin for 24 h in serum-free medium containing either 0.5% BSA or bFGF.

Attached cells were collected by trypsinization, pooled with suspended cells, washed, and fixed. Fixed cells were then stained with propidium iodide (50 µg/ml, Sigma-Aldrich, St. Louis, Mo.) for 20 min at 4° C. in the dark. Flow cytometry was performed on a FACS flow cytometer (EPICS XL-MCL; Coulter). The propidium iodide-stained cell population in sub-G0/G1, G1, S, and G2 µM phases were represented by distinct and quantified peaks in the fluorescence histograms obtained using the WinMDI logiciel program.

Figure 7:
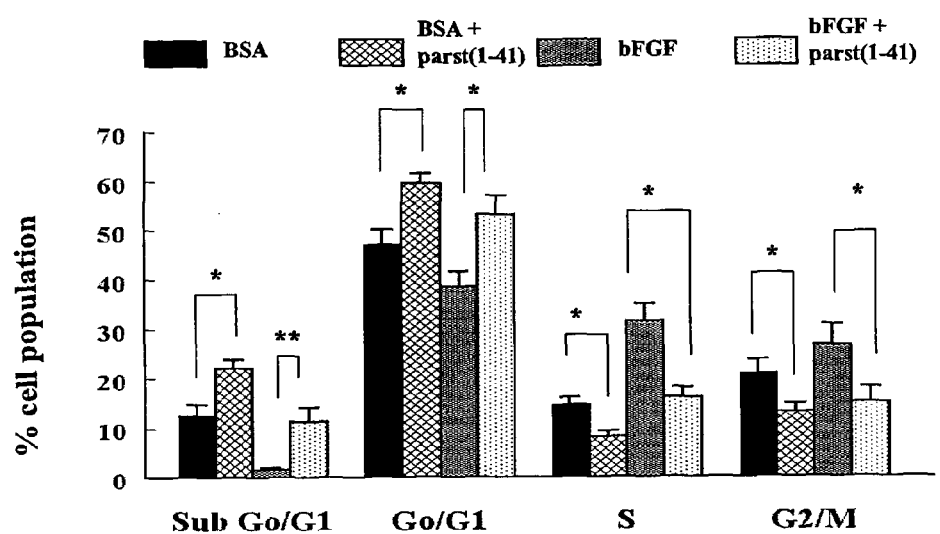
FIG. 7. Parstatin (1-41) promotes endothelial cell apoptosis. A, HUVECs were incubated in medium containing either 0.5% BSA or bFGF (5 ng/ml) in the absence or in the presence of human parstatin (1-41) (10 µM) for 24 h. Harvested cells were stained with propidium iodide and analyzed with a flow cytometer. Results are expressed as the mean percentage of cell population in sub-Go/G1, G1, S, and G2/M phases of the cell cycle ±SE. Experiments were run in duplicate and repeated three times. Statistical analysis was performed between indicated groups. $*p<0.05$, $**p<0.01$. B, HUVECs were incubated in medium containing either 0.5% BSA or VEGF (10 ng/ml) or bFGF (5 ng/ml) in the presence of vehicle or human parstatin (1-41) (10 µM) for 24 h. C, HUVECs were incubated in medium containing 0.5% BSA in the presence of vehicle (C) or indicated concentrations of human parstatin (1-41) or caspase inhibitor Z-VAD-FMK (100 µM) or the indicated combination for 24 h. Cells were fixed, stained with annexin V-FITC and PI and analyzed for healthy cells (annexin V- and PI-negative), early apoptotic cells (annexin V-positive and PI-negative) and late apoptotic or dead cells (annexin V- and PI-positive) by flow cytometry. The corresponding percentages of stained cells are shown in representative dot plots (B) or expressed as mean percentage of cell population ±SE (C). Statistical analysis was performed in early apoptotic cell population versus control. $*p<0.05$, $**p<0.01$.
Figure 7:
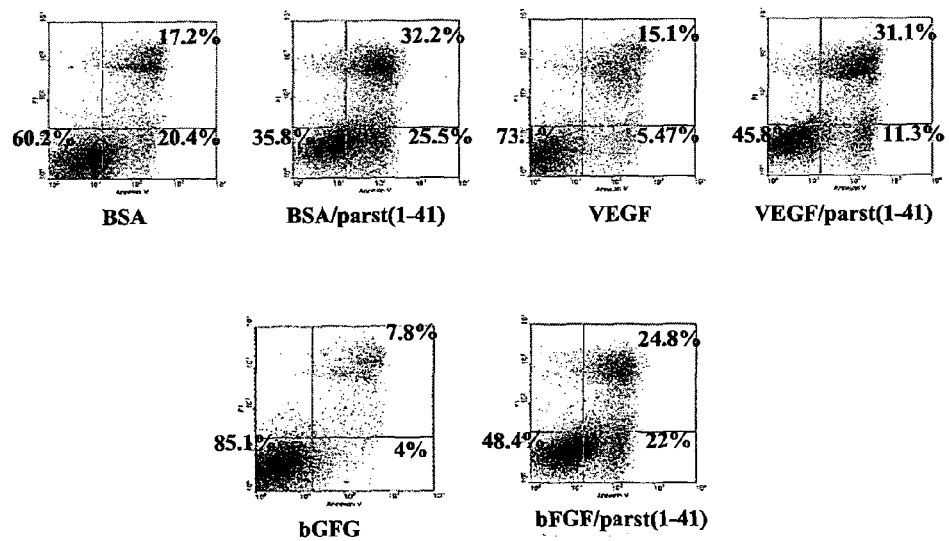
Figure 7:
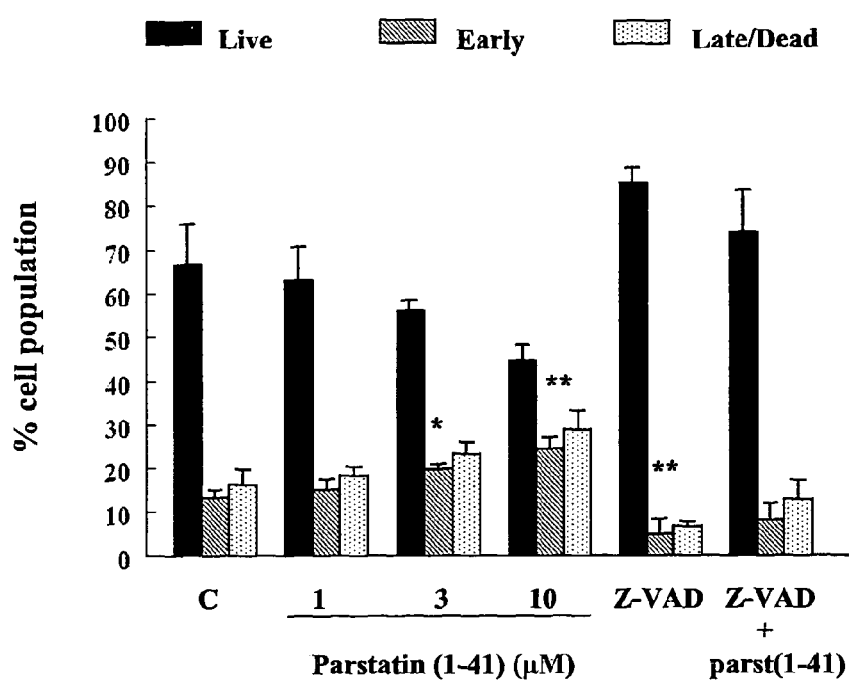

Human parstatin (1-41) increased the subG0/G1 cell fraction, which represents the percentage of apoptotic cells (FIG. 7A). In addition, parstatin (1-41) increased the cell fraction in G0/G1 phase, indicating that it induced endothelial cell cycle arrest (FIG. 7A). In agreement with results obtained in growth experiments, parstatin (1-41) reduced the percentages of cells in S and G2/M phases (FIG. 7A). Similar results were obtained when endothelial cells stimulated by growth factors, such as bFGF (FIG. 7A). These data demonstrate an inhibition of cell cycle progression by key angiogenic agonists.

The role of parstatin (1-41) in endothelial cell apoptosis was further explored using the Annexin V/propidium iodide based assay (Annexin V-FITC assay kit, BD Biosciences® PharMingen, Belgium), which is a valuable and very sensitive technique to detect apoptosis. Endothelial cells were grown until approximately 80% confluence. Cells were then treated in the absence or in the presence of human parstatin (1-41) for 24 h in serum-free medium containing either 0.5% BSA, VEGF, or bFGF. The broad spectrum caspase inhibitor Z-VAD-FMK (Z-Val-Ala-Asp(OCH$_3$)-Fluoromethylketone) was used alone or in combination with parstatin (1-41) at a fixed 100 µM concentration. Attached cells were pooled with suspended cells and resuspended in 100 µL of the kit reaction buffer containing propidium iodide and Annexin V-FITC, according to the manufacturer's instructions. Cells were analyzed on FACS flow cytometer within 1 h after staining. Cells were analyzed for healthy cells (annexin V- and PI-negative), early apoptotic cells (annexin V-positive, PI-negative) and late apoptotic or dead cells (annexin V- and PI-positive).

The results demonstrated that parstatin (1-41) increased the percentages of endothelial cells in early and late apoptotic stages (FIG. 7B). In parallel, the percentage of healthy/viable cells was equally decreased (FIG. 7B). Parstatin (1-41) promoted cell apoptosis in all culture conditions used with the effect to be more pronounced in endothelial cells stimulated by bFGF or VEGF (FIG. 7B). The apoptotic effect of parstatin (1-41) was concentration-dependent and was reversed by caspase inhibitor Z-VAD-FMK, indicating that caspase activation was involved in parstatin-mediated the apoptotic cell death (FIG. 7C).

Example 9

Parstatin (1-41) Inhibits Growth of Endothelial Cells is Associated and Induction of Apoptosis as Demonstrated by Caspase Activation and PARP Cleavage To further support the involvement of caspases in parstatin (1-41) pro-apoptotic effect, its effect on caspase-3 activation was examined using a commercially available kit (Promega, Madison, Wis.). The colorimetric substrate, Ac-DEVD-p-nitroanilide, is cleaved by caspase-3 to release yellow p-nitroanilide, was measured by absorbance at 405 nm to detect caspase activation.

HUVEC cells were grown in 60 mm tissue culture plates until approximately 80% confluency. Cells were treated in absence or in presence of 0.5% BSA or bFGF for 24 h in serum-free medium. Suspended and adherent cells were collected and lysed. Caspase-3 activity was measured by absorbance at 405 nm.

Figure 8:
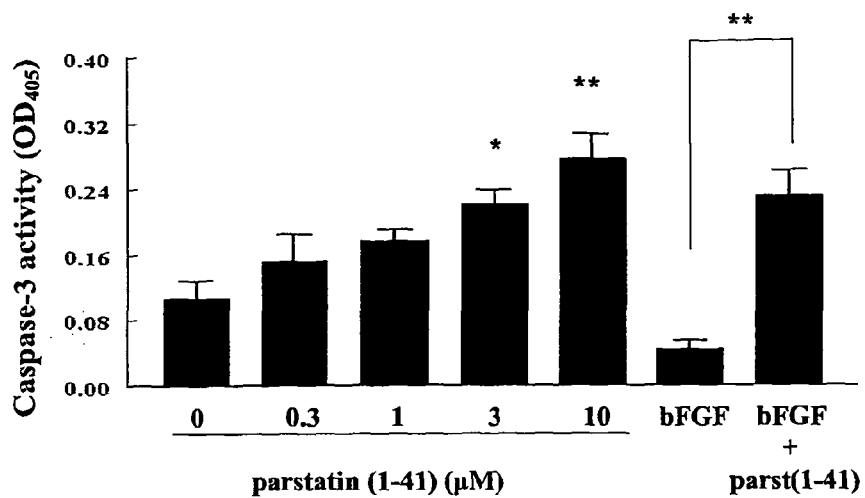
FIG. 8. Parstatin activates caspase-3 activity in endothelial cells. A, B, Caspase-3 activity was determined in cell extracts of HUVECs cultured in medium containing either 0.5% BSA in the presence of vehicle or indicated concentrations of human parstatin (1'-41) or bFGF (5 ng/ml) or Z-VAD-FMK (Z-VAD, 100 μM) or mouse parstatin (mouse, 10 μM) or scrambled parstatin (scr, 10 μM) or the indicated combination for 24 h. Results are expressed as mean of optical density at 405 nm ($OD_{405}$)±SE. Experiments were run in triplicate and repeated three times. Statistical analysis was performed versus controls or between indicated groups. *p<0.05, **p<0.01. C, HUVECs were cultured in medium containing either 0.5% BSA or bFGF (5 ng/ml) in the presence of vehicle or indicated concentrations of human parstatin (1-41) for 24 h. Protein lysates were immunoblotted with anti-PARP monoclonal antibody. Total protein levels were determined by probing membranes with α-tubulin antibody. Representative membrane blot is presented.
Figure 8:
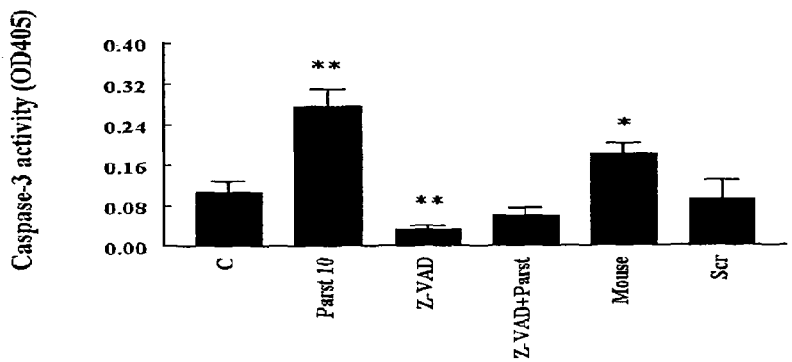
Figure 8:
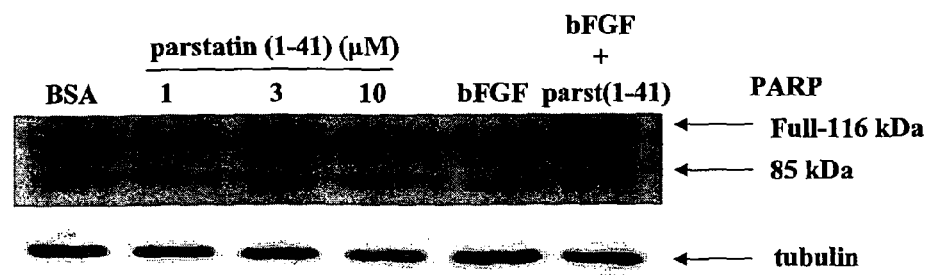

Human parstatin (1-41) increased the level of caspase-3 activity in concentration dependent manner (FIG. 8A). As expected, bFGF alone reduced significantly the activity of caspase-3, while when it was combined with parstatin (1-41) the caspase-3 activity increased dramatically (FIG. 8A). The combination of parstatin (1-41) with Z-VAD-FMK resulted in blockage of the action of parstatin, suggesting its specificity for caspase-3 (FIG. 8B). In addition, the promoting activity of parstatin (1-41) was observed as early as 3 hours after the exposure of cell to parstatin. Mouse parstatin caused a moderate increase in caspase-3 activity and scrambled parstatin was without effect (FIG. 8B). These results again demonstrate cross-species, sequence specific activity of parstatin (1-41).

Poly(ADP-ribose) polymerase (PARP) is activated in response to DNA damage and is implicated in the repair of DNA strand breaks. PARP cleavage by caspases produces 85- and 24-kDa fragments from the full-length 116-kDa protein. This leads to its inactivation and constitute early events in apoptosis.

Western blotting for PARP cleavage was performed on cell lysates from HUVEC cells cultured in serum free medium containing BSA for 24 h. The presence of parstatin (1-41) induced PARP cleavage to its signature 85-kDa fragment in concentration dependent manner (FIG. 8C). Parstatin (1-41) also increased PARP cleavage in bFGF-stimulated endothelial cells (FIG. 8C). Together these results suggest that parstatin (1-41) promoted apoptosis in growing endothelial cells and provide strong evidence that the cytotoxicity observed is due to caspase activation.

Example 10

Parstatin (1-41) is a Cell-Penetrating Peptide

Parstatin (1-41), because of highly hydrophobic properties of its first 23 amino acids, may possess the ability to interact with cell membrane lipid bilayers and to penetrate inside the cells. To investigate if parstatin exerts its cellular effects as a cell-permeable peptide, human parstatin (1-41) was conjugated with FITC. To measure the parstatin uptake into the endothelial cells, two methodological approaches were used: flow cytometry and fluorescence microscopy.

HUVEC cells in the exponential growth phase were exposed to various concentrations of parstatin (1-41)-FITC in serum-free medium containing 0.5% BSA. After incubation times ranging from 1 min to 60 min, cells were washed extensively. Washed cells were incubated for 10 min with trypsin at 37° C. to remove the cell surface-bound parstatin. Suspended cells were subsequently centrifuged, washed, and analyzed on FACS flow cytometer (EPICS XL-MCL; Coulter).

Figure 9:
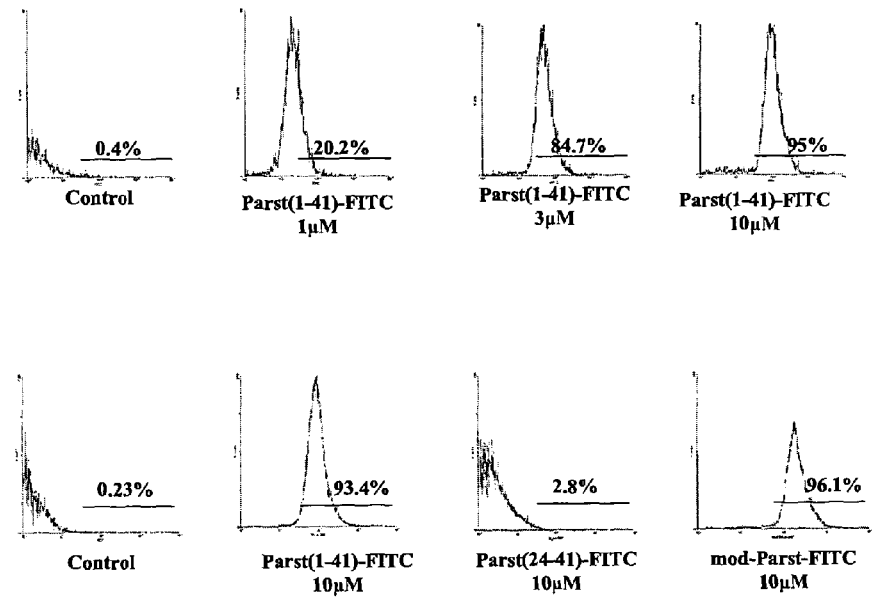
FIG. 9. Parstatin is a cell-penetrating peptide. A, Representative histograms showing the effect of parstatin peptides on cellular uptake. HUVECs were incubated with indicated concentrations of FITC-labeled parstatin (1-41) or FITC-labeled parstatin (24-41) or FITC-labeled modulated parstatin for 30 min. Trypsinized cells were analyzed by flow cytometry. The uptake of FITC-labeled parstatin peptides into cells was assessed by the change of the FITC-positive cell population compared with untreated control cell samples. Experiments were run in duplicate and repeated three times. B, Representative histograms showing the cellular uptake of parstatin (1-41) by the time. HUVECs were incubated with FITC-labeled parstatin (1-41) (10 μM) for the indicated time intervals. Cells were analyzed by flow cytometry. Experiments were run in duplicate and repeated three times. C, Fluorescence microscopy images. HUVECs were incubated with 10 mM of FITC-labeled (green) parstatin (1-41) or modulated parstatin or parstatin (24-41) for the indicated time intervals. All cells were also stained with the nuclear dye DAPI (blue). Arrows show the FITC-signal localization on cell membrane or in cytosol. Experiments were run in triplicate and repeated three times. D, Modulated parstatin mimics parstatin (1-41) in inhibition of MAPK activation and DNA synthesis in endothelial cells. For MAPK activation (left panel), HUVECs were pretreated with parstatin (1-41) (10 μM) or parstatin (24-41) (10 μM) or modulated parstatin (10 μM) for 1 h and then stimulated with bFGF (5 ng/ml) for 10 min. Cells were then processed as described in FIG. 6. Representative blots are shown. For DNA synthesis (right panel), HUVECs were incubated in serum-free medium supplemented with bFGF (5 ng/ml) in the absence or in the presence of parstatin (1-41) (10 μM) or parstatin (24-41) (10 μM) or modulated parstatin (10 μM) for 18 h. All cells were pulsed with [$^3$H]thymidine for an additional 6 h. All experiments were run in triplicate and were repeated at least three times. Results are expressed as mean±SE of DPM per well and presented as percentage change of control (0%). Statistical analysis was performed between indicated groups. **p<0.01.
Figure 9:
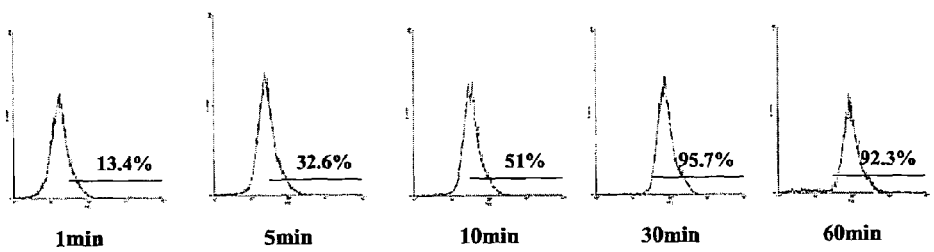
Figure 9:
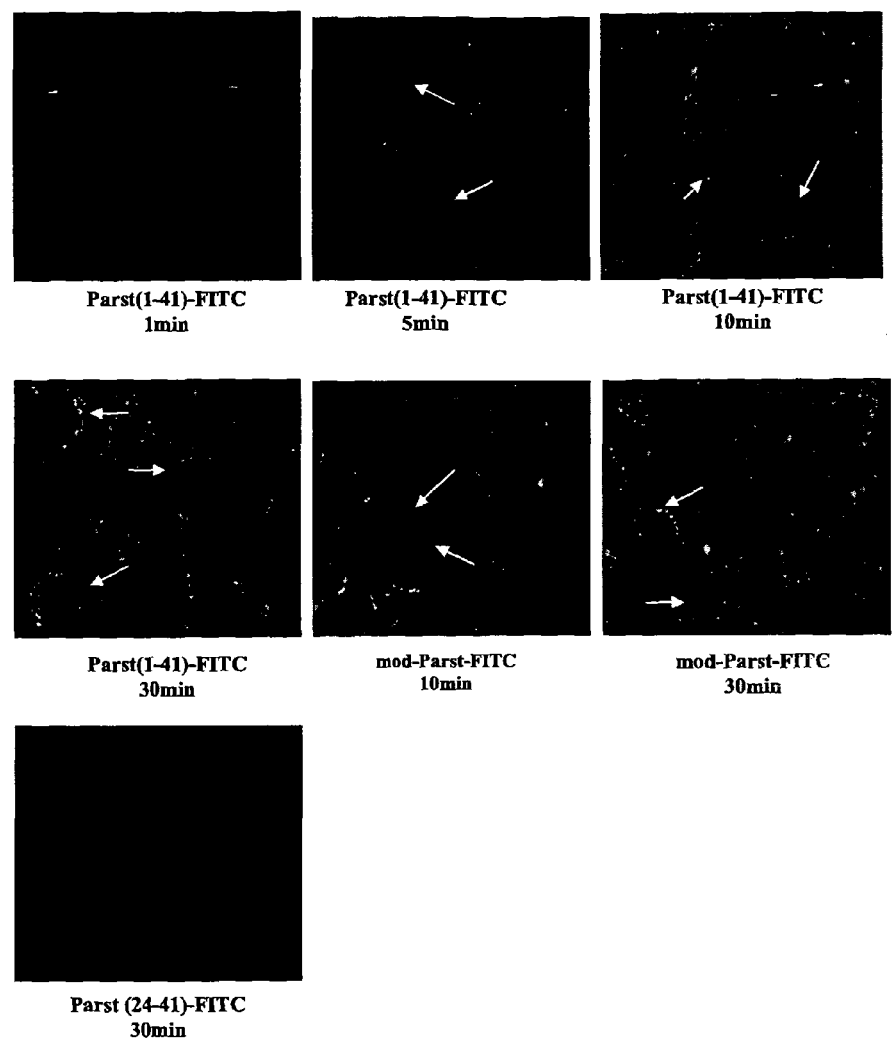
Figure 9:
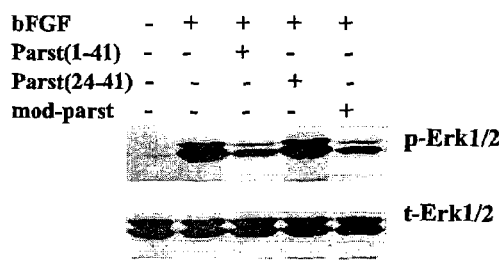
Figure 9:
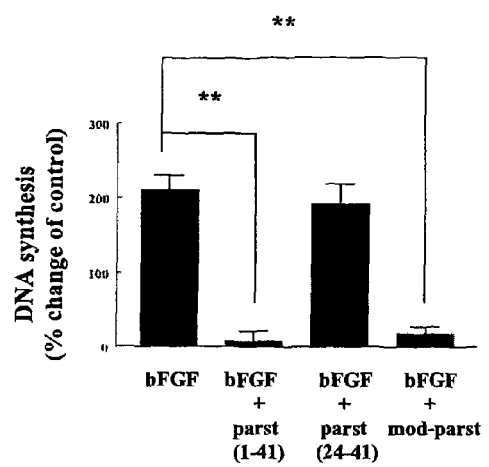

The uptake of a given parstatin (1-41)-FITC into cells was assessed by the change of the FITC-positive cell population compared with untreated control cell samples. The fraction of FITC-positive cell population exposed to parstatin-FITC for 30 min was increased in a dose-dependent manner (FIG. 9A). Even at the shortest time of exposure to parstatin studied of 1 min the FITC-positive cell population was 13.4% and reached to maximal level after 30 min of treatment (FIG. 9B).

For imaging, endothelial cells were incubated with a FITC-labelled parstatin (1-41) as described above and the distribution of the parstatin was observed with fluorescent microscopy. 4',6-Diamidino-2-phenylindole (DAPI) was used to stain nuclei of all cells. Cell fluorescence was imaged on a Nikon Eclipse TE2000-U microscope. FITC and DAPI were excited using 490-nm and 360-nm filters, respectively. The emission signals were sorted out using 514 and 460 filters for the FITC and DAPI, respectively. HUVEC cells were treated with 10 μM of parstatin (1-41)-FITC for different time intervals. In control sample, for which no fluorescence was observed, cells were not exposed to parstatin (1-41)-FITC (FIG. 9C). FITC signal was detected as early as 5 min of cell exposure to parstatin (1-41)-FITC (FIG. 9C). At this time point, parstatin (1-41) signal was exclusively localized in cell membranes. When endothelial cells were exposed to parstatin (1-41)-FITC for 10 min the FITC signal was detected in cell membranes and in the cytosol (FIG. 9C). The exposure of cells for 30 min resulted in signal localization only in the cytosol, preferentially around the nucleus (FIG. 9C).

These data suggest that parstatin (1-41) possess the ability to interact with cell membranes and enter cells at a rate dependent on the exposure time and the concentration applied. They also suggest that parstatin peptides including the N-terminal sequence may be exceptionally useful and readily taken up in topical or local applications (e.g., intraocular injections for the treatment of retinal angiogenesis). This kinetic profile was in agreement with the initiation of parstatin-mediated biological effects (e.g. the inhibition of bFGF-induced MAPK activation). Taken together, these results provide evidence that parstatin (1-41) is a cell-penetrating peptide which exerts its biological effects intracellularly.

We also used the parstatin (24-41) fragment conjugated with FITC. When endothelial cells exposed to parstatin (24-41)-FITC no fluorescence was observed (FIG. 9C), and the FITC-positive cell population was minimal and comparable with that of control cells (FIG. 9A). The inability of parstatin (24-41) to interact with and penetrate cell membranes provides a plausible explanation for the absence of cellular effects. However, the exposure of endothelial cells to FITC-labelled modulated parstatin, which is scrambled at residues 24-41, resulted in marked increase of the fraction of FITC-positive like that observed with FITC-parstatin (FIG. 9A). Accordingly, the microscope images presented similar time distribution of FITC-signal with that observed in parstatin (1-41)-treated cells (FIG. 9C). These results are in perfect agreement and associated with the ability of modulated parstatin to inhibit bFGF-induced Erk1/2 activation and DNA synthesis (FIG. 9D). These results provide evidence that the inhibitory sequence of parstatin is likely localized within its hydrophobic domain and this moiety needs to be framed with additional amino acids to facilitate its solubility and activity.

Example 11

Parstatin (1-41) and Parstatin (1-26) and (24-41) Fragments Suppress Choroidal Neovascularization in Mice Parstatin (1-41), hydrophobic parstatin (1-26) fragment and hydrophilic parstatin (24-41) fragment were used in an in vivo mouse model of choroidal neovascularization. In particular, laser photocoagulation-induced rupture of Bruch's membrane was used to generate choroidal neovascularization as a preclinical disease model for age-related macular degeneration. Pathogen-free C57BL/6J (4-5 week-old) mice were treated in accordance with the Association for Research in Vision and Ophthalmology Statement for the Use of Animals in Ophthalmic and Vision Research and the guidelines of the Animal Care and Use Committee at local University Medical School.

C57BL/6J (4-5 week-old) mice were anesthetized with ketamine hydrochloride (100 mg/kg body weight) and xylazine-(4 mg/Kg body weight) and the pupils were dilated with 1% tropicamide. Laser photocoagulation (75 μm spot size, 0.1 sec duration, 120 mW) was performed in the 9, 12, and 3 o'clock positions of the posterior pole of the retina with the slit lamp delivery system of an Oculight GL diode laser (Index, Mountain View, Calif.) and a handheld cover slip as a contact lens to view the retina. Production of a bubble at the time of laser, which indicates rupture of Bruch's membrane, is an important factor in obtaining CNV. Therefore, only burns in which a bubble was produced were included in the study. Two weeks after rupture of Bruch's membrane, anesthetized mice were perfused with 50 mg/ml fluorescein-labelled-dextran ($2\times10^6$ average molecular weight, Sigma-Aldrich, St. Louis, Mo.). The eyes were then dissected and fixed in 10% Formalin for 3 hours and choroidal flat mounts were examined by fluorescence microscopy. Image-Pro Plus software (Media Cybernetics, Silver Spring, Md.) was used to measure the total area of CNV at each rupture site by personnel blinded as to study treatments and groups.

Intraocular injections of parstatin peptides were performed with a Harvard pump microinjection apparatus and pulled glass micropipets. Under a dissecting microscope, the sharpened tip of a micropipette was passed through the sclera just behind the limbus into the vitreous cavity. Intravitreal injections of 1 μl solutions of parstatin (1-41) or parstatin (24-41) in phosphate buffered saline (PBS) or PBS alone were administered. Also, intravitreal injections of 1 μl solutions of parstatin (1-26) in dimethyl sulphoxide (DMSO) or DMSO alone were administered. Intravitreal injections of parstatin peptides were administered immediately after laser treatment and 7 days after laser treatment. Choroidal neovascularization was assessed 14 days after laser treatment.

Figure 10:
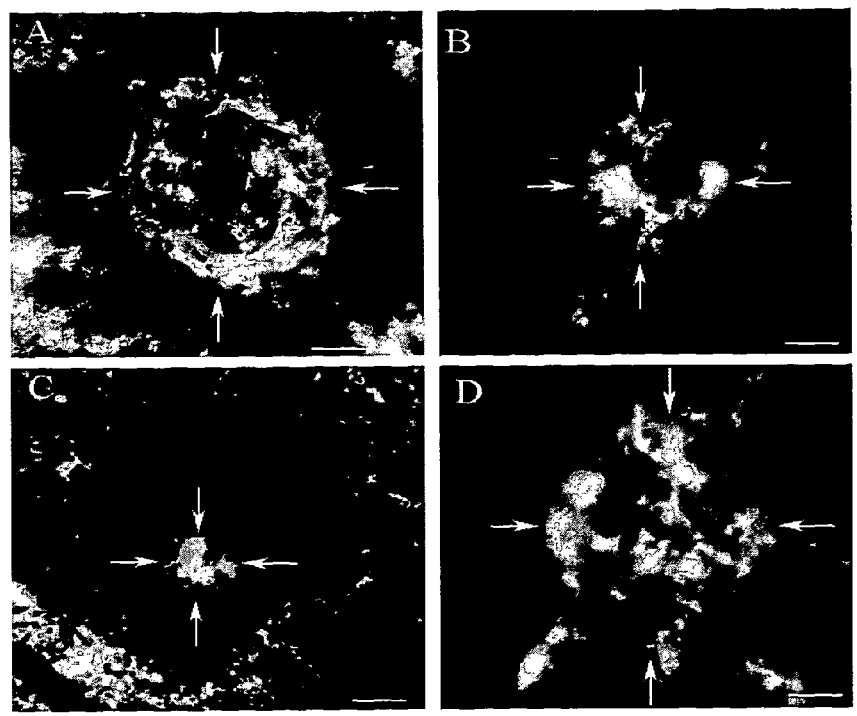
FIG. 10. Parstatin (1-41) suppresses choroidal neovascularization (CNV) in mice. Laser-induced ruptures of Bruch's membrane were performed in mice. Intravitreal injections of indicated doses of parstatin (1-41) or vehicle (control) or scrambled parstatin (10 μg) were administered immediately after laser treatment and 7 days after laser treatment. CNV was assessed 14 days after laser treatment. Mice were perfused with FITC-labeled dextran and choroidal flat mounts were prepared and examined by fluorescence microscopy. Compared to control eyes (A), those injected with 1 μg (B) or 10 μg (C) of parstatin (1-41) showed proportionally smaller areas of CNV. CNV in eyes injected with scrambled parstatin (D) was similar to that obtained in control mice. E, The area of CNV at each rupture site was measured by image analysis. Results are expressed as mean areas ($mm^2$) of Choroidal NV±SE for each group calculated from indicated number (n) of eyes. Statistical analysis was performed versus control group. *p<0.05.
Figure 10:
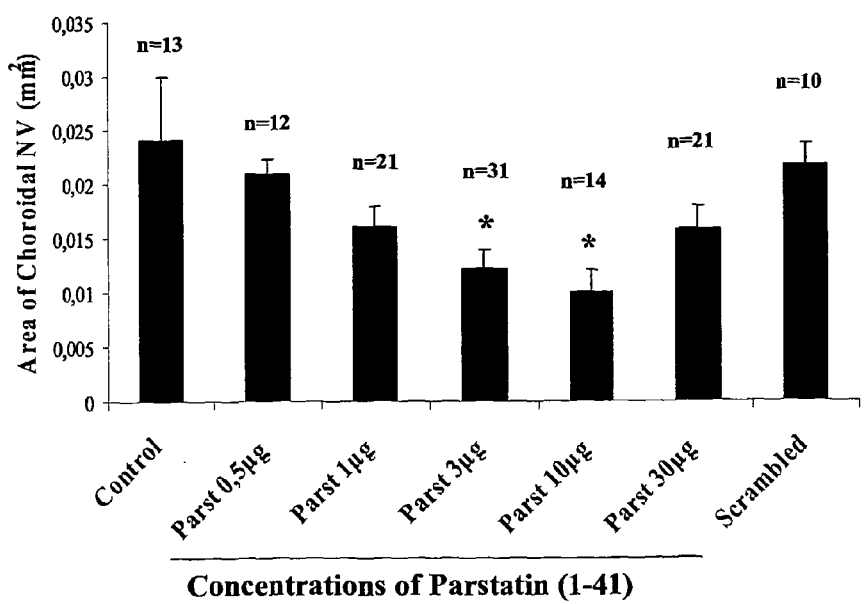

Retinal whole mounts from fluorescein dextran-perfused mice treated with parstatin (1-41) had areas of choroidal neovascularization that were much smaller than those seen in control mice treated with vehicle (PBS) (FIGS. 10A, B, and C). Measurements of the area of choroidal neovascularization by image analysis confirmed that there was significantly less neovascularization in eyes treated with parstatin (1-41) compared to control mice (FIG. 10E). The inhibitory effect of parstatin (1-41) was dose-dependent and the maximum inhibition of choroidal neovascularization was demonstrated with the 10 μg dose, which showed a 58% inhibition (p=0.015). This is comparable to the best known treatments for suppressing choroidal neovascularization, such as anti-VEGF, anti-VEGFR2 or anti-PlGF treatment. The dose of 30 μg did not provide additional benefit (FIG. 10E). Mice treated with scrambled parstatin (10 μg) had choroidal neovascularization similar to that obtained in control mice (FIGS. 10D and E; p=0.6). Slit lamp examinations showed that all parstatin (1-41) doses were well tolerated with no signs of irritation, inflammation, or other ocular toxicity and no signs of systemic toxicity were seen.

Figure 11:
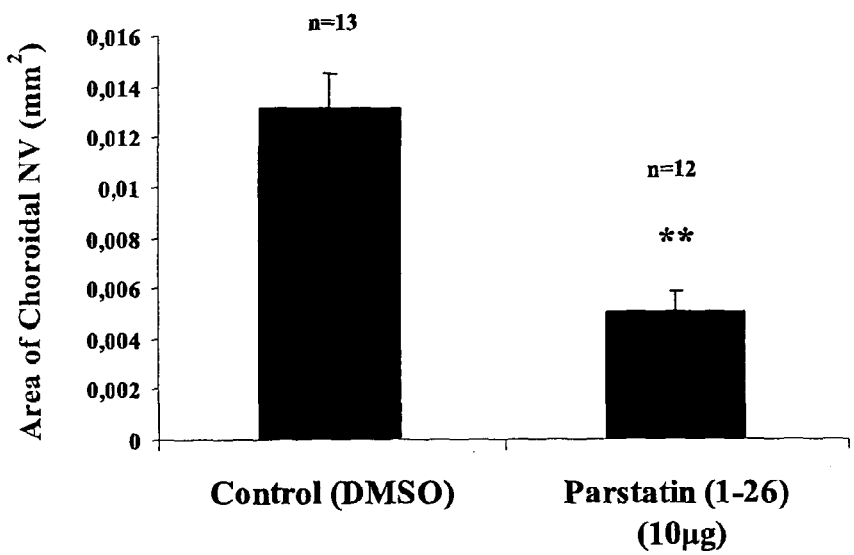
FIG. 11. Parstatin (1-26) and (24-41) fragments suppress choroidal neovascularization (CNV) in mice. Laser-induced ruptures of Bruch's membrane were performed in mice. A, Intravitreal injections of vehicle (control, DMSO) or parstatin (1-26) (10 μg) were administered immediately after laser treatment and 7 days after laser treatment. B, Intravitreal injections of vehicle (control, PBS) or 10 μg of parstatin (1-41) or parstatin (24-41) (10 μg) were administered immediately after laser treatment and 7 days after laser treatment. CNV was assessed 14 days after laser treatment. Mice were perfused with FITC-labeled dextran and choroidal flat mounts were prepared and examined by fluorescence microscopy. Compared to control eyes, those injected with parstatin (1-41) or parstatin (1-26) or (24-41) fragments showed significant smaller areas of CNV. The area of CNV at each rupture site was measured by image analysis. Results are expressed as mean areas ($mm^2$) of Choroidal NV±SE for each group calculated from indicated number (n) of eyes. Statistical analysis was performed versus control group. *p<0.05, **p<0.01.
Figure 11:
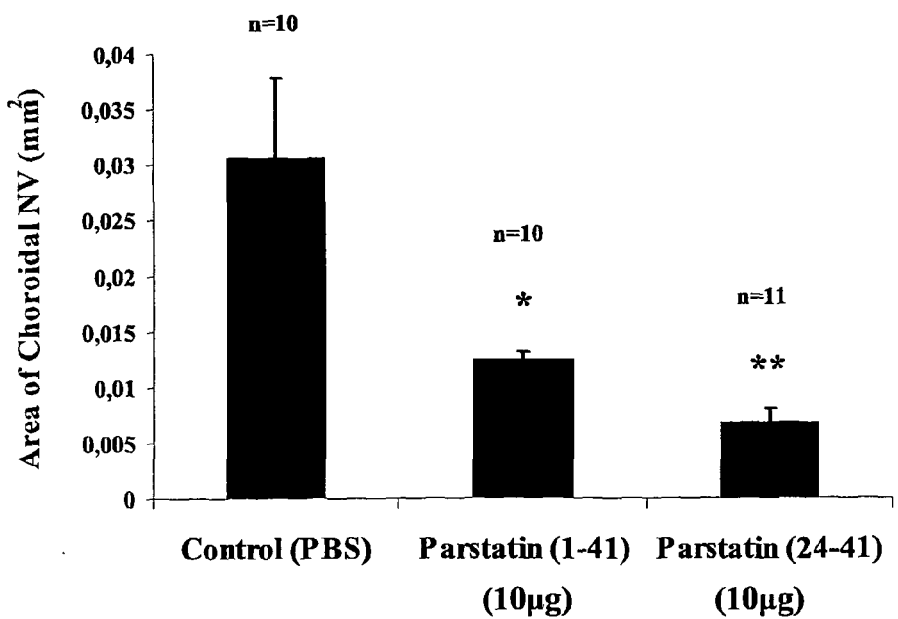

Mice treated with parstatin (1-26) fragment had choriodal neovascularization significantly inhibited by 62%, at concentration of 10 μg, compared to control mice treated with DMSO (FIG. 11A). Similarly, measurements of the area of choroidal neovascularization by image analysis confirmed that there was remarkably less neovascularization in eyes treated with parstatin (24-41) fragment, at concentration of 10 μg, compared to control mice treated with PBS (FIG. 11B). Interestingly, this inhibitory effect (77%) was superior to that obtained with parstatin (1-41) (59%) to the same experiments and concentration (10 μg) (FIG. 11B).

Overall, these results suggest that parstatin (1-41) inhibited choroidal neovascularization in a dose-dependent manner, with most effective concentration at 10 μg. This inhibitory effect was more evident and potent either after the administration of parstatin (1-26) fragment or parstatin (24-41) fragment. Again, the ability of parstatin peptides to function across species is noted. Human parstatin peptides potently inhibited choroidal neovascularization in mice tissue in a non-species specific manner.

Example 12

Parstatin (1-41) and Parstatin (1-26) and (24-41) Fragments Suppress Retinal Neovascularization in Mice Parstatin (1-41), hydrophobic parstatin (1-26) fragment and hydrophilic parstatin (24-41) fragment were used in an in vivo mouse model of retinal neovascularization. In particular, oxygen-induced retinopathy was used to generate retinal neovascularization as a preclinical disease model for retinopathy of prematurity and other retinal neovascular diseases such as diabetic retinopathy. In this model, exposing newborn mice to hyperoxia prompts regression or delay of retinal vascular development, followed by abnormal angiogenesis after their return to normal oxygen levels. Mainly, this model mirrors the events that occur during retinopathy of prematurity, when infants are removed from oxygen-rich incubators, a condition involving pathological neovascularization that can affect premature infants and result in permanent visual loss. In recent years, the use of this model has been extended to the general study of ischemic vasculopathies, such us diabetic retinopathy, and related antiangiogenic interventions, and it is now used extensively in both basic and applied research environments.

Pathogen-free C57BL/6 mice were treated in accordance with the Association for Research in Vision and Ophthalmology Statement for the Use of Animals in Ophthalmic and Vision Research and the guidelines of the Animal Care and Use Committee at local University Medical School. Litters of 7-day old (P7) mice were exposed to an atmosphere of 75% oxygen in an airtight incubator for 5 days (P12), after which they were returned to room air for 5 days (P17). For quantification of oxygen-induced retinal neovascularization, mice on P17 were given an intraocular injection of 1 µl of rat anti-mouse platelet endothelial cell adhesion molecule-1 (PECAM-1) antibody (Pharmingen, San Jose, Calif.) under a dissecting microscope with Harvard pump microinjection apparatus. Mice were euthanized 12 hours after injection and eyes were fixed in PBS-buffered formalin for 5 hours. Retinas were dissected, washed and incubated with goat anti-rat polyclonal antibody conjugated with Alexa 488 or were labeled with *griffonia simplicifolia*-594 (Invitrogen, Carlsbad, Calif.) for 45 min. Both methods gave similar results. Retinal flat mounts were prepared and assessed with fluorescence microscope using imaging software. Intravitreal injections of 1 µl solutions of parstatin (1-41) or parstatin (24-41) in phosphate buffered saline (PBS) or PBS alone were administered. Also, intravitreal injections of 1 µl solutions of parstatin (1-26) in dimethyl sulphoxide (DMSO) or DMSO alone were administered on P12 (immediately after the mice are removed from hyperoxic conditions) and on P15.

Figure 12:
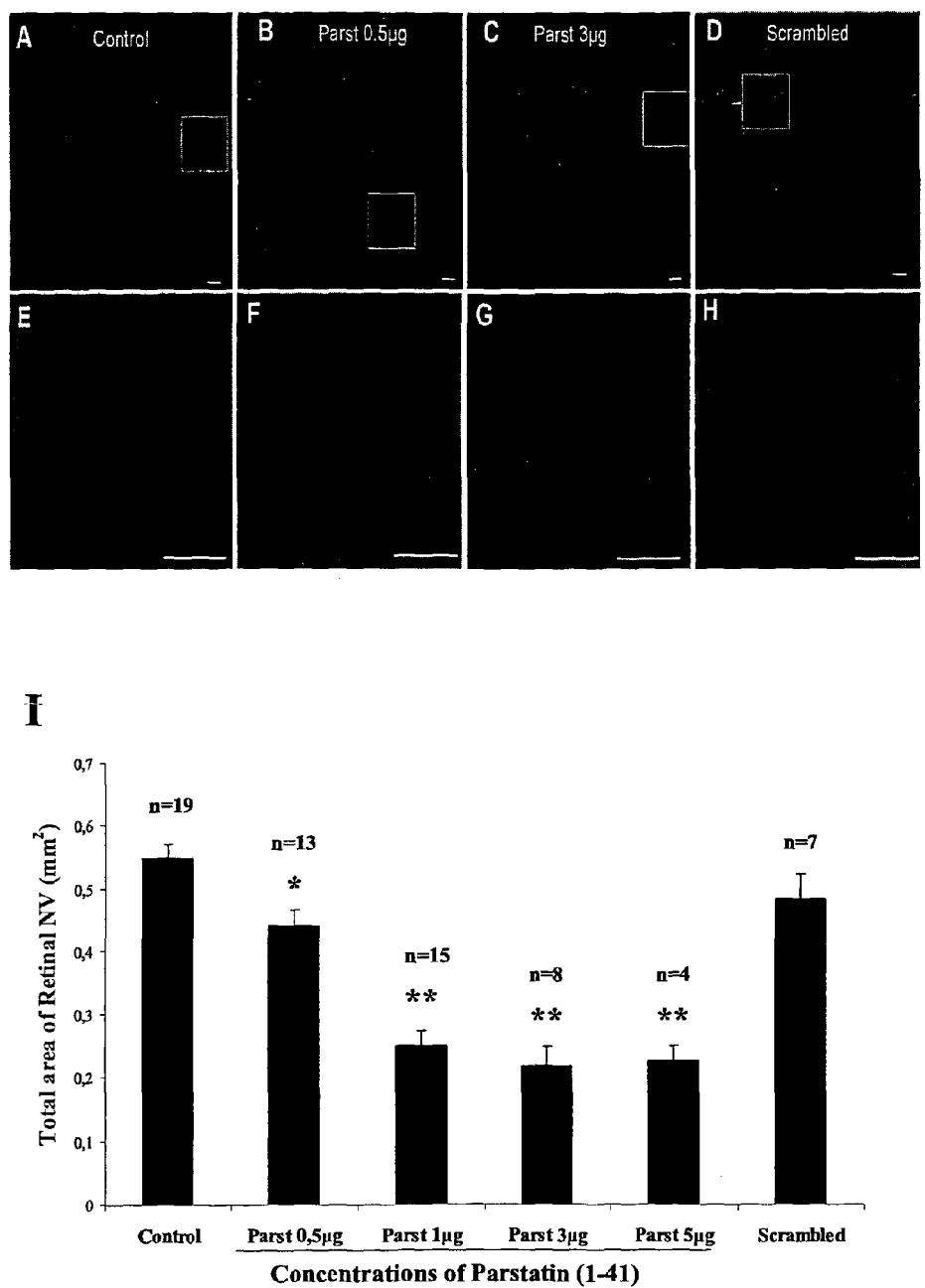
FIG. 12. Parstatin (1-41) suppresses retinal neovascularization in mice. Newborn mice were placed in 75% oxygen at postnatal day 7. At P12 they were returned to room air. Intravitreal injections of indicated doses of parstatin (1-41), vehicle (control) or scrambled parstatin (10 μg) were administrated on P12 and P15. At P17, mice were treated with *griffonia simplificolia* isolectin B4-589. Compared to control retinas (A, E), those treated with 0.5 μg (B, F) or 3 μg (C, G) of parstatin (1-41) showed proportionally less areas of retinal neovascularization. Retinal neovascularization in retinas treated with scrambled parstatin (D, H) was similar to that observed in control mice. E, F, G and H are higher magnification images of the boxes in A, B, C and D, respectively. Scale bar: 200 μm. I, Total area of neovascularization (NV) at each retina site was measured by image analysis. Results are expressed as mean areas ($mm^2$) of retinal neovascularization ±SE for each group calculated from indicated number (n) of eyes. Statistical analysis was performed versus control group. *p<0.05, **p<0.01.

When mice with ischemic retinopathy were given intravitreal injections of PBS at P12 and P15, stained retinal flat mounts showed extensive areas of neovascularization (FIG. 12A, E). However, treatment of mice with increasing doses of parstatin (1-41) at P12 and P15 caused a dose-dependent inhibition of neovascularization on the surface of the retina (FIGS. 12B, F and C, G). Measurements of neovascularization by image analysis showed significant reduction in the area of retinal neovascularization in parstatin (1-41)-treated mice, at doses ranging from 0.5 to 5 µg (FIG. 12I). Maximum inhibition was demonstrated with the 3 µg dose, which showed a 60% inhibition (p=0.0005). The dose of 5 µg did not provide additional benefit (FIG. 12I). Doses of 10 and 30 µg were not well tolerated when administered to newborn mice. Retinal adherence made the retinas virtually impossible to retrieve. There was also adherence of the eyelids and occasional cataract formation with these doses. Mice treated with scrambled parstatin had retinal neovascularization similar to that obtained in control mice treated with PBS (FIGS. 12D, H and I).

Figure 13:
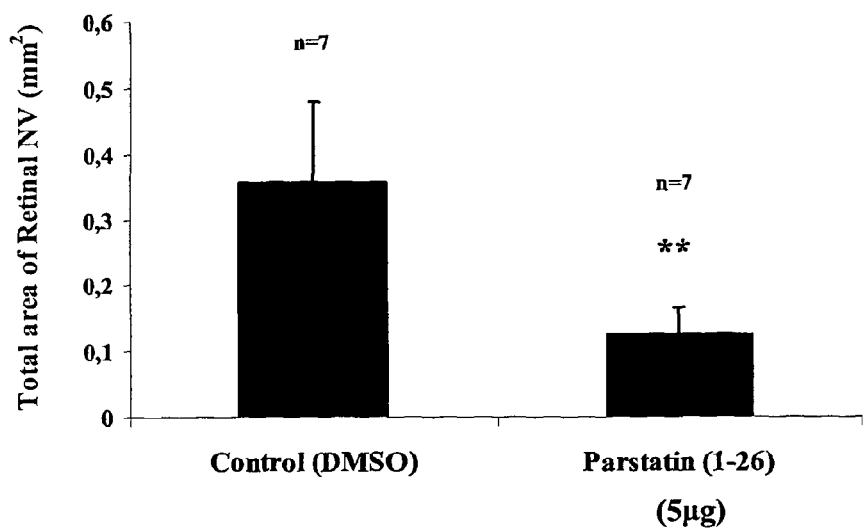
FIG. 13. Parstatin (1-26) and (24-41) fragments suppress retinal neovascularization in mice. Newborn mice were placed in 75% oxygen at postnatal day 7. At P12 they were returned to room air. A, Intravitreal injections of vehicle (control, DMSO) or parstatin (1-26) (5 μg) were administrated on P12 and P15. B, Intravitreal injections of vehicle (control, PBS) or parstatin (1-41) (5 μg) or parstatin (24-41) (5 μg) were administrated on P12 and P15. At P17, mice were treated with *griffonia simplificolia* isolectin B4-589. Compared to control retinas those treated with parstatin (1-26) or (24-41) fragments showed significant less areas of retinal neovascularization. Total area of neovascularization (NV) at each retina site was measured by image analysis. Results are expressed as mean areas ($mm^2$) of retinal neovascularization ±SE for each group calculated from indicated number (n) of eyes. Statistical analysis was performed versus control group. **p<0.01.
Figure 13:
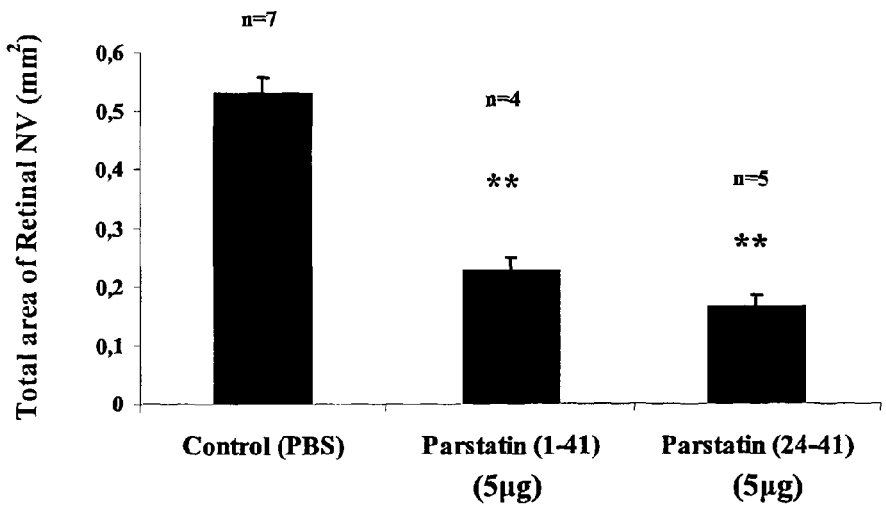

Mice treated with parstatin (1-26) fragment had retinal neovascularization significantly inhibited by 65%, at concentration of 5 µg, compared to control mice treated with DMSO (FIG. 13A). Similarly, measurements of the area of retinal neovascularization by image analysis confirmed that there was remarkably less neovascularization in retinas treated with parstatin (24-41) fragment, at concentration of 5 µg, compared to control mice treated with PBS (FIG. 13B). Interestingly, the inhibitory effect (69%) of parstatin (24-41) was superior to that obtained with parstatin (1-41) (57%) to the same experiments and concentration (5 µg) (FIG. 13B).

These results suggest that parstatin (1-41) inhibited retinal neovascularization in a dose-dependent manner, with most effective concentration at 3-5 µg. This inhibitory effect was also evident and likely more potent either after the administration of parstatin (1-26) fragment or parstatin (24-41) fragment. Again, the ability of parstatin peptides to function across species is noted. Human parstatin peptides potently inhibited retinal neovascularization in mice tissue in a non-species specific manner.

Example 13

Parstatin (1-41) and Parstatin (1-26) and (24-41) Fragments Suppress Corneal Neovascularization and Inflammation in Rats Parstatin (1-41), hydrophobic parstatin (1-26) fragment and hydrophilic parstatin (24-41) fragment were used in an in vivo rat model of corneal neovascularization. In particular, chemical burn-induced corneal trauma was used to generate corneal neovascularization as a preclinical disease model simulating a plethora of corneal diseases associated with abnormal formation of new blood vessels. The cornea is normally an avascular tissue that can be stimulated to undergo pathological neoangiogenesis in response to mechanical or chemical injuries, pterygium, herpetic keratitis, etc. In this model, an inflammatory response is considered an important prerequisite for neovascularization. This model is widely accepted and is one of the most extensively studied models, which provides an in vivo environment to study this complex process with convenient access to the corneal tissue and the highly visible developing vasculature.

Pathogen-free male Sprague-Dawley rats (250-300 gr) were treated in accordance with the Association for Research in Vision and Ophthalmology Statement for the Use of Animals in Ophthalmic and Vision Research and the guidelines of the Animal Care and Use Committee at local University Medical School. Rats were anesthetized with intramuscular injection of ketamine (25 mg/Kg) and xylazine hydrochloride (10 mg/Kg). All eyes were examined to exclude any eyes with corneal scars or preexisting neovascularization. Corneas were cauterized by pressing an applicator stick coated with 75% silver nitrate and 25% potassium nitrate to the center of the corneas for 4 seconds, under a microscope. Excess silver nitrate was removed by rinsing the eyes with 5 mL of 0.9% saline. To increase the reproducibility of the injuries, all burns were made by one investigator. The injured eyes then received topical tobramycin 0.3% to avoid infection. Immediately after the burns, rats were randomly divided into groups and each injured eye was twice subconjunctivally injected with 20 µl of parstatin (1-41) or parstatin (24-41) in phosphate buffered saline (PBS) or PBS alone. Also, subconjunctivally injections with 20 µl solutions of parstatin (1-26) in dimethyl sulphoxide (DMSO) or DMSO alone were administered. Injections were performed in the 12, and 6 o'clock positions 1 mm posterior to the limbus with a 30-gauge needle attached to a 1-mL tuberculin syringe under a microscope. Seven days later, each eye underwent slit-lamp examination and photographs of the cornea were taken with a digital camera (Nikon D2X) attached to a microscope. The corneal neovascularization was assessed using a semiautomatic program, which was developed in MATLAB 7.5. The program included conversion of the color image into a black-and-white image, selection of a threshold level that made possible the visualization of the corneal vessels and calculation of the corneal neovascularization (as a percentage of the number of pixels of the new vessels to the pixels of the total corneal area). The total corneal area was outlined with the innermost vessel of the limbal arcade used as the border. All calculations were made by a blinded observer.

After the above-described processes were performed, the rats were sacrificed (7 days) and the eyes were excised. All eyes were sectioned (4 μm) and stained with hematoxylin-eosin. Two independent pathologists, in a blinded manner, evaluated the microvessel density and the inflammatory cell infiltration in each slide. Total corneal vascular vessels and neutrophils were counted at 200× in seven representative stained tissue sections for each eye, covering all cornea area and having a similar distance from the central burn.

Figure 14:
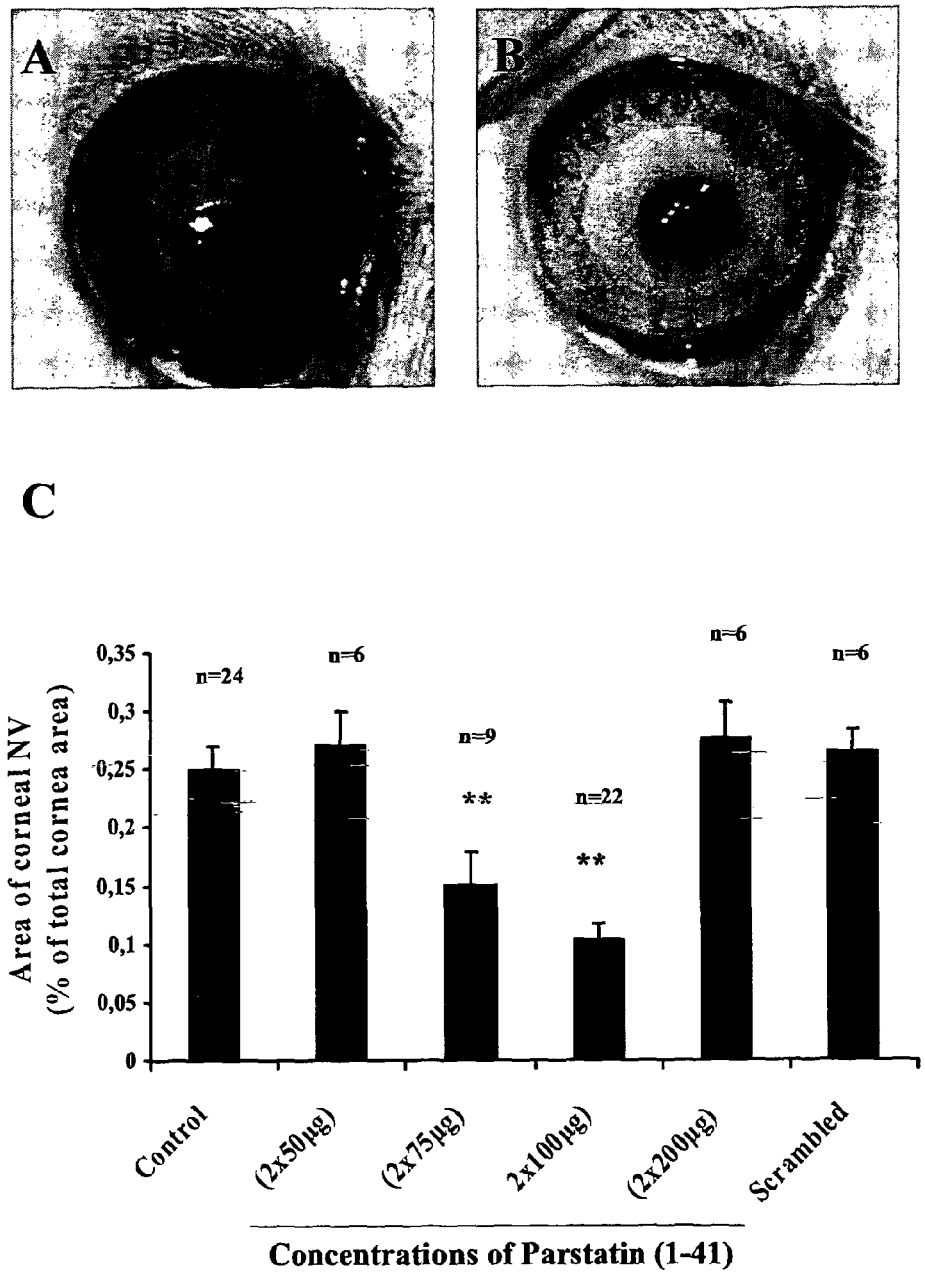
FIG. 14. Parstatin (1-41) suppresses corneal neovascularization in rats. Chemical burn-induced corneal trauma was performed by the application of 75% silver nitrate and 25% potassium nitrate to the centre of rat corneas. Two subconjunctival injections per eye of indicated doses of parstatin (1-41) or vehicle (control) or scrambled parstatin (scrambled, 2×100 μg) were administrated immediately after cauterization. Corneal neovascularization was assessed 7 days after cauterization. Compared to control corneas (A), those treated with 2×100 µg (B) of parstatin (1-41) showed proportionally reduced areas of corneal neovascularization. C, Total area of neovascularization (NV) in each cornea was measured by image analysis. Corneal neovascularization in eyes treated with scrambled parstatin (C) was similar to that observed in control mice. Results are expressed as the mean percentage of area covered by vessels to the total corneal area ±SE for each group calculated from the indicated number (n) of eyes. Statistical analysis was performed versus control group. $**p<0.01$.

The time course of corneal neovascularization following cauterization is highly reproducible and well characterized. In the first 24 h after the injury, the limbal vessels that surround the cornea appear slightly engorged. Within 48 h the limbal arcades are extended further into the cornea with many vascular sprouts directing centrally toward the site of injury. By three and four days post cautery, this dense brushwork of vessels elongates evenly into the cornea from all sides. New blood vessels cover almost 30% of the total cornea area by day seven (FIG. 14A). The effect of parstatin (1-41) on corneal neovascularization was evaluated by comparing the total neovascularization area between the parstatin-treated and control (PBS) groups seven days after corneal cauterization. The results showed that the onset and progression of corneal neovascularization were markedly delayed in the group treated with 2×100 μg of parstatin (1-41) (FIG. 14B). Measurements of total corneal neovascularization area by image analysis showed a 59% decreased neovascularization area in the parstatin (1-41) group (2×100 μg; p<0.001) compared to control group (FIG. 14C). No significant differences were found between the control group and the groups treated with 2×50 and 2×200 μg parstatin (1-41) (FIG. 14C). Again, rats treated with scrambled parstatin had corneal neovascularization areas similar to those obtained in control rats (FIG. 14C).

Figure 15:
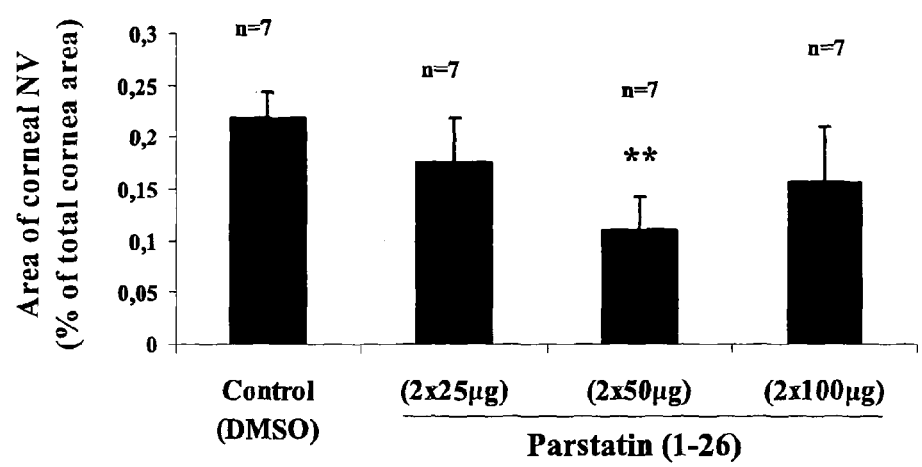
FIG. 15. Parstatin (1-26) and (24-41) fragments suppress corneal neovascularization in rats. Chemical burn-induced corneal trauma was performed by the application of 75% silver nitrate and 25% potassium nitrate to the centre of rat corneas. A, Two subconjunctival injections per eye of indicated doses of parstatin (1-26) or vehicle (control, DMSO) were administrated immediately after cauterization. B, Two subconjunctival injections per eye of indicated doses of parstatin (24-41) or vehicle (control, PBS) or parstatin (1-41) (2×100 µg) were administrated immediately after cauterization. Corneal neovascularization was assessed 7 days after cauterization. Compared to control corneas those treated with 2×50 µg of parstatin (1-26) or (24-41) fragments showed proportionally reduced areas of corneal neovascularization. Total area of neovascularization (NV) in each cornea was measured by image analysis. Results are expressed as the mean percentage of area covered by vessels to the total corneal area ±SE for each group calculated from the indicated number (n) of eyes. Statistical analysis was performed versus control group. $**p<0.01$.
Figure 15:
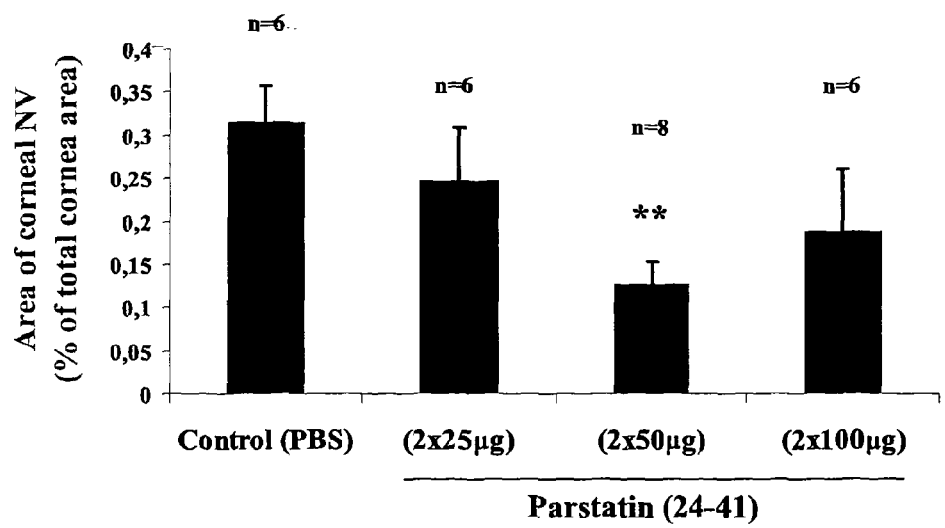

Rats treated with parstatin (1-26) fragment had corneal neovascularization significantly inhibited by 50%, at concentration of 2×50 μg, compared to control mice treated with DMSO (FIG. 15A). Similarly, measurements of the area of cornea neovascularization by image analysis confirmed that there was remarkably less neovascularization in corneas treated with parstatin (24-41) fragment (60%), at concentration of 2×50 μg, compared to control mice treated with PBS (FIG. 15B). Interestingly, the inhibitory effects of parstatin (1-26) and (24-41) fragments were comparable to that obtained with parstatin (1-41), but were evident at lower concentrations.

Figure 16:
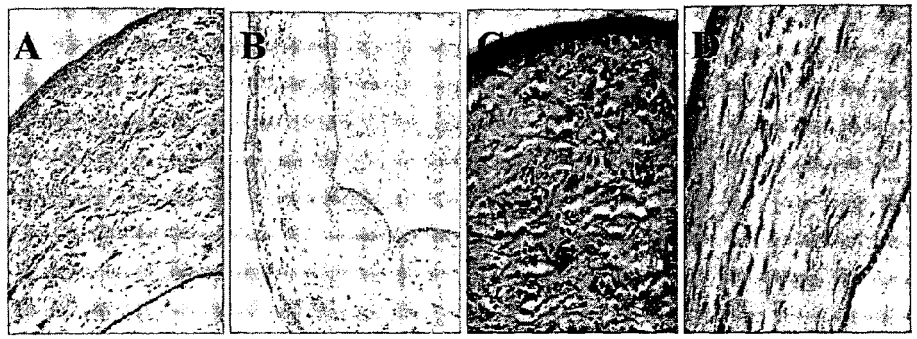
FIG. 16. Corneal histopathology. Rats were treated as described in FIGS. 14 and 15. Seven days after cauterization, eyes were excised, embedded in paraffin and sectioned. Sections were stained with hematoxylin-eosin and vascular vessels (A, B, and E) or neutrophils (C, D, and F) in the corneas were counted at magnification ×200 or ×400, respectively. Compared to control corneas (A, C), those treated with 2×100 µg (B, D) of parstatin (1-41) showed much fewer blood vessels or infiltrating neutrophils. The blood vessels or neutrophils' density in corneas treated with scrambled parstatin were similar to those observed in control rats. Compared to control corneas those treated with 2×50 µg of parstatin (1-26) or (24-41) fragments showed significant reduced blood vessels or infiltrating neutrophils. The total number of blood vessels (E) was measured in seven sections from each eye and results are expressed as mean number of vascular vessels per section ±SE for each group calculated from indicated number (n) of eyes. The total number of neutrophils (F) was measured in seven sections from each eye and results are expressed as mean number of inflammatory cells per section±SE for each group calculated from indicated number (n) of analysis was performed versus control group. $**p<0.01$.
Figure 16:
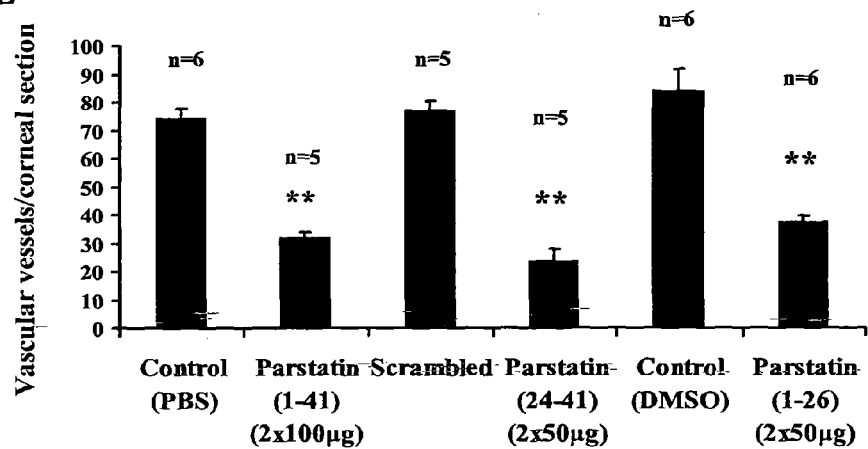
Figure 16:
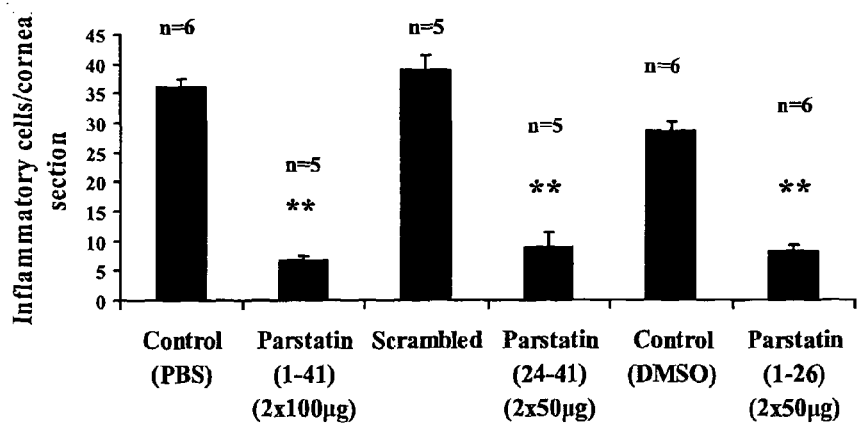

In line with the image analysis data, hematoxylin and eosin staining of corneas revealed that there was more cellularity and thickening in control animals (FIGS. 16A and C) than in parstatin (1-41)-treated rats (FIGS. 16B and D). All corneas in the control group showed large numbers of intrastromal blood vessels (FIG. 16A), while comparatively less corneal neovascularization infiltration was apparent in the corneal stroma following all parstatin (1-41) treatment regimens (FIG. 16B). Mean density of vascular vessels (32.14±1.73) was reduced by 57% (p<0.001) with parstatin (1-41) administration (2×100 μg) compared with the mean number of vascular vessels (74.3±3.52) in the control sections (FIG. 16E). In scrambled parstatin treatment (2×100 μg), 77.17±3.11 was counted as the mean vascular vessel number within the sections, which was not significantly different from that of the control animals (FIG. 16E). In addition, corneas treated with parstatin (1-26) fragment had corneal mean number of vascular vessels significantly inhibited by 55%, at concentration of 2×50 μg, compared to control mice treated with DMSO (FIG. 16E). Similarly, measurements of vascular vessels confirmed that there was remarkably less neovascularization in corneas treated with parstatin (24-41) fragment (68%), at concentration of 2×50 μg, compared to control mice treated with PBS (FIG. 16E). The inhibitory effects of parstatin (1-26) and (24-41) fragments were comparable to that obtained with parstatin (1-41), but were evident at lower concentrations. There was no sign of cytotoxicity in any of the treatment groups. Endothelial cells and epithelial layers exhibited no histological alteration other than some preparation artifacts.

In addition, one interesting observation in our experiments concerned the superior corneal transparency in the parstatin (1-41) group compared to the control group. This might suggest an additional inhibitory effect of parstatin on concomitant corneal scarring, possibly related to inhibition of inflammatory migration and invasion. The beneficial effect of parstatin (1-41) in this model might relate not only to direct anti-angiogenic effects of the peptide but to a potential anti-inflammatory effect. Indeed, the parstatin (1-41) group (FIG. 16D) had markedly fewer infiltrated inflammatory cell (neutrophils) than did the control (FIG. 16C). The numbers of neutrophils were 6.9±0.57 cells/corneal section in the parstatin (1-41)-injected corneas (2×100 μg) and 36.25±1.32 cells/corneal section in the PBS-injected controls corneas (FIG. 16F; p<0.001). In the scrambled parstatin group the inflammatory cells were 39±2.54 cells/corneal section (FIG. 16F). In addition, corneas treated with parstatin (1-26) fragment had corneal mean number of infiltrated neutrophils significantly inhibited by 71%, at concentration of 2×50 μg, compared to control mice treated with DMSO (FIG. 16F). Similarly, measurements of corneal infiltrated neutrophils confirmed that there was remarkably less inflammatory cells in corneas treated with parstatin (24-41) fragment (75%), at concentration of 2×50 μg, compared to control mice treated with PBS (FIG. 16F). Again, the anti-inflammatory effects of parstatin (1-26) and (24-41) fragments were comparable to that obtained with parstatin (1-41), but were evident at lower concentrations.

Example 14

Parstatin (1-41) and Parstatin (1-26) and (24-41) Fragments Reduce VEGF-Induced Retinal Leukostasis in Mice Inflammatory leukocyte accumulation is a common feature of major ocular diseases. For instance, leukocytes have been shown to play a role in the pathogenesis of ischemic retinopathies. VEGF, which is a potent chemoattractant for leukocytes, is increased in ischemic retina and is necessary for retinal neovascularization to occur. Parstatin (1-41), hydrophobic parstatin (1-26) fragment and hydrophilic parstatin (24-41) fragment were used in an in vivo mice model of VEGF-induced retinal leukostasis.

C57BL/6J (4-5 week-old) mice were anesthetized with ketamine hydrochloride (100 mg/kg body weight) and xylazine (4 mg/Kg body weight) and the pupils were dilated with 1% tropicamide. Intravitreal injections of 1 μl solutions of 10 μM VEGF, which is the optimal concentration for promoting leukostasis, or parstatin (1-41) or parstatin (24-41) in phosphate buffered saline (PBS) or PBS alone or the combinations were administered. Also, intravitreal injections of 1 μl solutions of parstatin (1-26) in dimethyl sulphoxide (DMSO) or DMSO alone were administered to assess leukostasis. Six hours after intravitreal injections, which was the optimal time determined for VEGF-induced leukostasis, animals were perfused with PBS to remove intravascular content, including nonadherent leukocytes. Perfusion with FITC-conjugated Concanavalin A (40 μg/ml in PBS, Vector Labs, Burlingame, Calif.) was then performed to label adherent leukocytes and vascular endothelial cells, followed by removal of residual unbound lectin with PBS perfusion. Retinal flat mounts were prepared and examined with the Axioskop microscope and images were digitized. The total numbers of leukocytes adhering to the retinal vessels were counted at 200× by the same investigator, with the investigator being masked as to the nature of the specimen.

Figure 17:
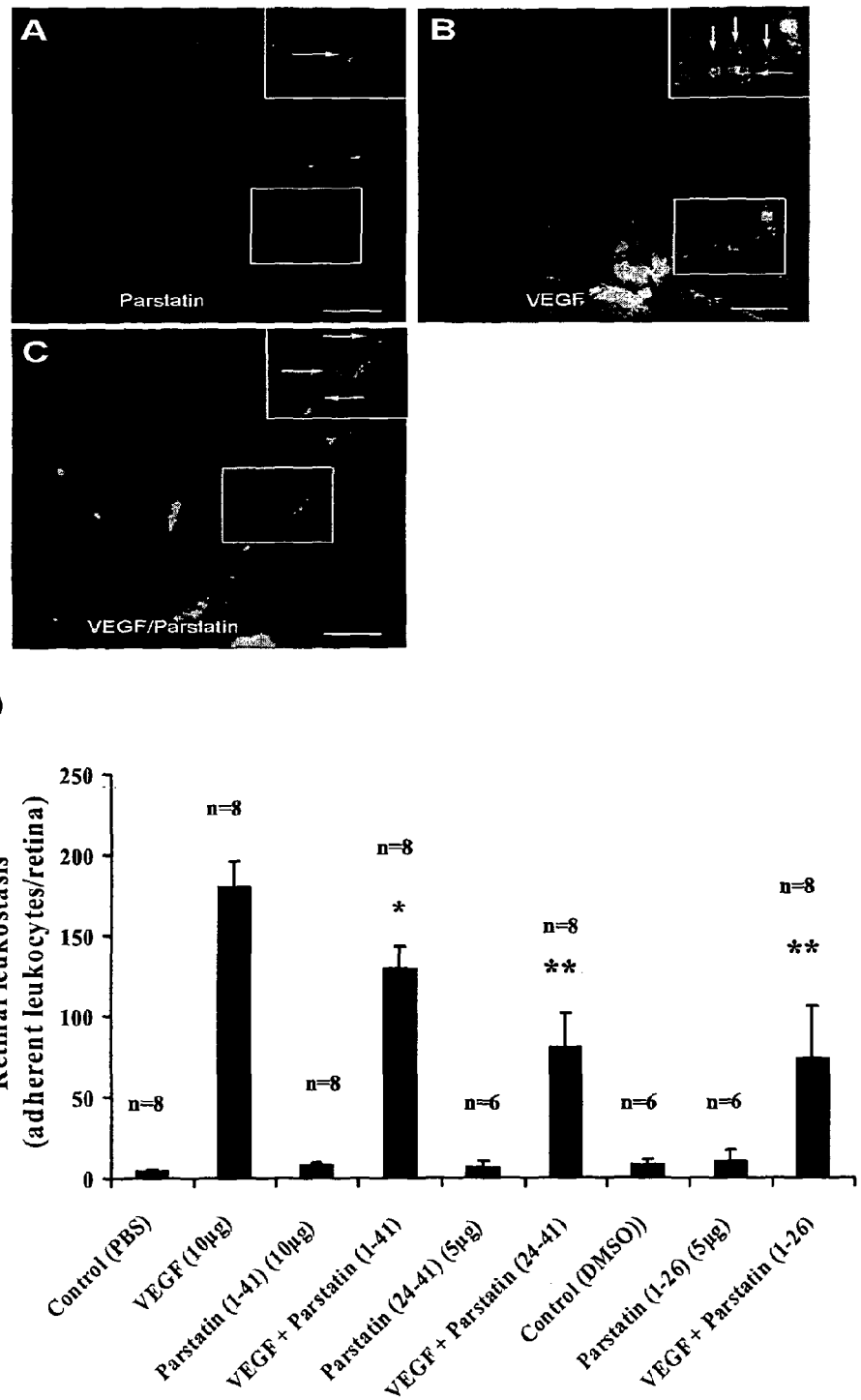
FIG. 17. Parstatin (1-41) and parstatin (1-26) and (24-41) fragments reduce VEGF-induced retinal leukostasis in mice. Intravitreal injections of vehicle (control), or VEGF (10 µM), or parstatin (1-41), or parstatin (1-26) or parstatin (24-41) or the indicated combination of VEGF with parstatin peptides were administrated to assess their effect on retinal leukostasis. After 6 h, mice were perfused with FITC-conjugated concavalin A. Retinal flat mounts were prepared and the total numbers of leukocytes adhering to the retinal vessels (arrows) were counted at magnification ×200. Very few leukocytes adhered to the retinal vessels following injections of vehicle or parstatin (1-41) (A) (×200; insert: ×400), while pronounced leukostasis was observed following injections of VEGF (B) (×200; insert: ×400). The combination of parstatin (1-41) (10 µg) with VEGF resulted in a significant reduction in VEGF-induced leukostasis (C) (×200). The VEGF-induced adhered leukocytes in retinas treated with 5 µg of parstatin (1-26) or (24-41) fragments were significantly reduced. D, Total numbers of adherent leukocytes were measured in each retina and results are expressed as mean number of leukocytes per section ±SE for each group calculated from indicated number (n) of eyes. Statistical analysis was performed versus control group. Scale bar: 200 µm. $**p<0.01$.

Six hours after VEGF injection (10 µM), a large number of leukocytes firmly adhered to the retinal vessels (181±16 cells/retina) compared to vehicle (PBS)-treated controls (5±1 cells/retina) and parstatin (1-41) alone (8.5±1.6) (FIGS. 17A, B and D). However, when VEGF-treated animals were co-injected with 10 µg of parstatin (1-41), the number of firmly adhering leukocytes was significantly reduced by 28.7% (129±14 cells/retina; p=0.014) in comparison with the VEGF-treated controls (FIGS. 17C and D). In addition, when VEGF-treated animals were co-injected with 5 µg of parstatin (24-41) or (1-26) fragments the number of firmly adhering leukocytes was poptently reduced by 55% (81±21 cells/retina) and 59% (74±32 cells/retina), respectively, in comparison with the VEGF-treated controls (FIG. 17D). Interestingly, this inhibitory effects of parstatin (24-41) and (1-26) fragments were superior to that obtained with parstatin (1-41) and at lower concentrations.

Example 15

Parstatin (1-41) Attenuates Myocardial Ischemia-Reperfusion Injury in Rats

Parstatin (1-41) was used in an in vivo rat model of cardiac ischemia and reperfusion, and in an in vitro isolated rat heart model of ischemia-reperfusion injury. Male Sprague Dawley rats at 8 weeks of age were used and treated in compliance with the "Guide for the Care and Use of Laboratory Animals" formulated by the National Research Council (USA), 1996.

For in vivo infarct size studies, rats were anesthetized with pentobarbital sodium (50 mg/Kg) and heparin (1000 IU/Kg) and underwent 30 min of regional ischemia followed by 120 min of reperfusion. Parstatin (1-41) was administered-intravenously over 1 min starting 15 min prior to ischemia, or 15 min after the onset of ischemia, or 10 seconds after the onset of reperfusion in separate series of experiments (n=6/group).

To induce ischemia, ligature was positioned around the left main coronary artery and threaded through a plastic snare to permit reversible occlusion of the coronary artery. Coronary occlusion was induced by clamping the snare onto the heart and reperfusion was achieved by releasing the snare. At the end of reperfusion, the coronary artery was re-occluded and the risk zone was delineated by perfusion of 0.5% Evans' blue into the aortic cannula. Hearts were sectioned and incubated in 1% triphenyltetrazolium chloride in phosphate buffer for 15 min to define white necrotic tissue when fixed in 10% formalin for 24 h. Area at risk (AAR) and infarct-to-risk rations were determined by computerized planimetry using J-Image v.i.6 software (NIH, Bethesda, Mass.).

Figure 18:
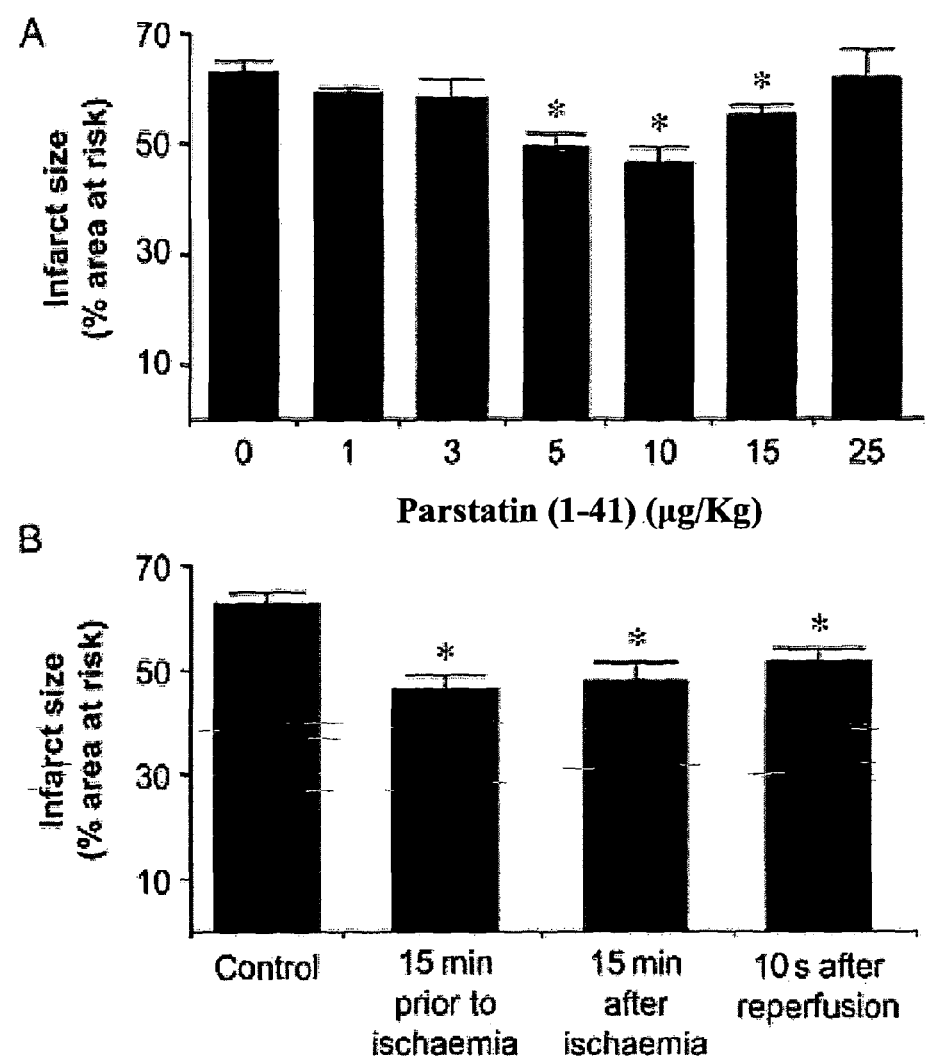
FIG. 18. Parstatin (1-41) attenuates myocardial ischemia-reperfusion injury in rats. Analysis of the cardioprotective effects of parstatin. A, Dose-response curve of parstatin (1-41). Rats were treated with either saline or increasing concentrations of human parstatin (1-41) administered as an intravascular bolus 15 min prior to ischemia. Infarct size was determined after 30 min regional ischemia and 120 min reperfusion. B, Phase of action of parstatin (1-41). Rats were treated with parstatin (1-41) (10 µg/Kg, IV) 15 min prior to ischemia, 15 min after the onset of ischemia, or 10 seconds after the onset of reperfusion. Results are expressed as mean±SD, n=6 rats/group. Statistical analysis was performed versus control group. $*p<0.05$.

Infarct size was 63±2% of the AAR in the control group (FIG. 18A). However, when parstatin (1-41) was injected 15 min prior to ligating the left coronary artery, a concentration-dependant reduction in infarct size was evident (FIG. 18A). A significant change in infarct size was detected with the 5-15 µg/Kg doses with 10 µg/Kg as the optimal dose. These hearts had an infarct size of 46±3% of the area at risk, which is a 26% reduction in infarct size compared with control (FIG. 18A). No significant change in infarct size was detected with the 1, 3, or 25 µg/Kg doses of parstatin (1-41). Treatment with parstatin (1-41) 15 min after ischemia and 10 second after the onset of reperfusion still resulted in a 23% and 18% reduction in infarct size, respectively (FIG. 18B). Heart rate and blood pressures were monitored throughout the procedure and there were no significant differences between baseline hemodynamics of the groups. Mean arterial pressure decreased during ischemia and reperfusion in all groups but there was no significant difference between groups. These data demonstrate that parstatin (1-41) is useful for both prophylaxis and treatment of myocardial ischemia/reperfusion injury.

Example 16

Parstatin (1-41) Attenuates Myocardial Ischemia-Reperfusion Injury in Excised Hearts by Recruiting the G1-Protein Activation Pathway Including p38MAPK, Erk1/2, Nitric Oxide (NOS), and $K_{ATP}$ Channels For in vitro studies, excised hearts were retrogradely perfused through the aorta with a modified Krebs buffer. Coronary flow rate was determined by timed collection of the coronary effluent. A saline-filled latex balloon connected to a pressure transducer was inserted into the left vertical (LV), and baseline end-diastolic pressure was set at 5-10 mmHg. Heart rate, LV end-diastolic pressure and LV developed pressures (LVDP) were recorded continuously. The measurements for post-ischemic recovery of LVDP used for comparison were taken at 180 min of reperfusion. After stabilization for 15-20 min, the hearts (n=6/group) were subjected to 30 min of regional ischemia, followed by 180 min of reperfusion.

Figure 19:
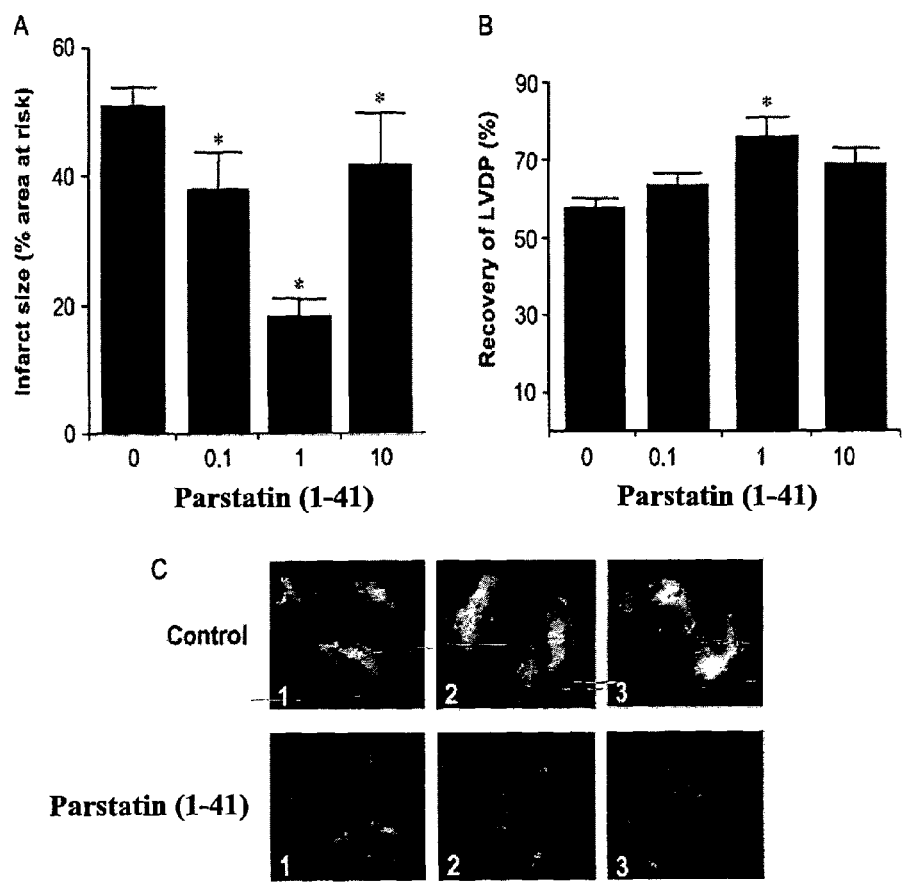
FIG. 19. Parstatin (1-41) attenuates myocardial ischemia-reperfusion injury in rat excised hearts. Cardioprotective effects of parstatin (1-41) in vitro. Isolated rat hearts were perfused with either indicating concentrations of parstatin (1-41) for 15 min prior to ischemia. Infarct size and left ventricular developed pressure (LVDP) were determined after 30 min regional ischemia and 180 min reperfusion. A, infarct size. B, Recovery of LVDP. C, Typical photographs of myocardial slices from three control and three parstatin (1-41)-treated hearts. Infarcted areas are pale grey, whereas viable myocardium is dark red. Results are expressed as mean±SD, n=6/group. Statistical analysis was performed versus control group. $*p<0.05$.

Different concentrations of parstatin (1-41) were perfused 15 min prior to coronary occlusion until occlusion. Control hearts produced an infarct size of 51±3% of the area at risk (FIG. 19A). Continuous administration of parstatin (1-41) for 15 min immediately before ischemia resulted in a concentration-dependent reduction of infarct size (FIG. 19A). Parstatin (1-41) at 1 µM led to the largest reduction in infarct size (18±3%), a 65% decrease. A picture representation of infarct in control versus parstatin (1-41) (1 µM)-treated hearts is shown in FIG. 19C. Parstatin (1-41) lost its efficacy when used at 10-fold higher or lower concentrations. Similarly, parstatin (1-41) increased recovery of LVDP in a concentration-dependent manner (FIG. 19B). Again, the optimal concentration was 1 µM which produced a 23% recovery of LVDP (FIG. 19B).

Rats were treated with pertussis toxin (PTX) 48 h before ischemia. In the presence of PTX, parstatin (1-41) no longer was able to reduce 4 infarct size or increase the recovery of LVDP after ischemia-reperfusion injury (FIGS. 20A and B).

Figure 20:
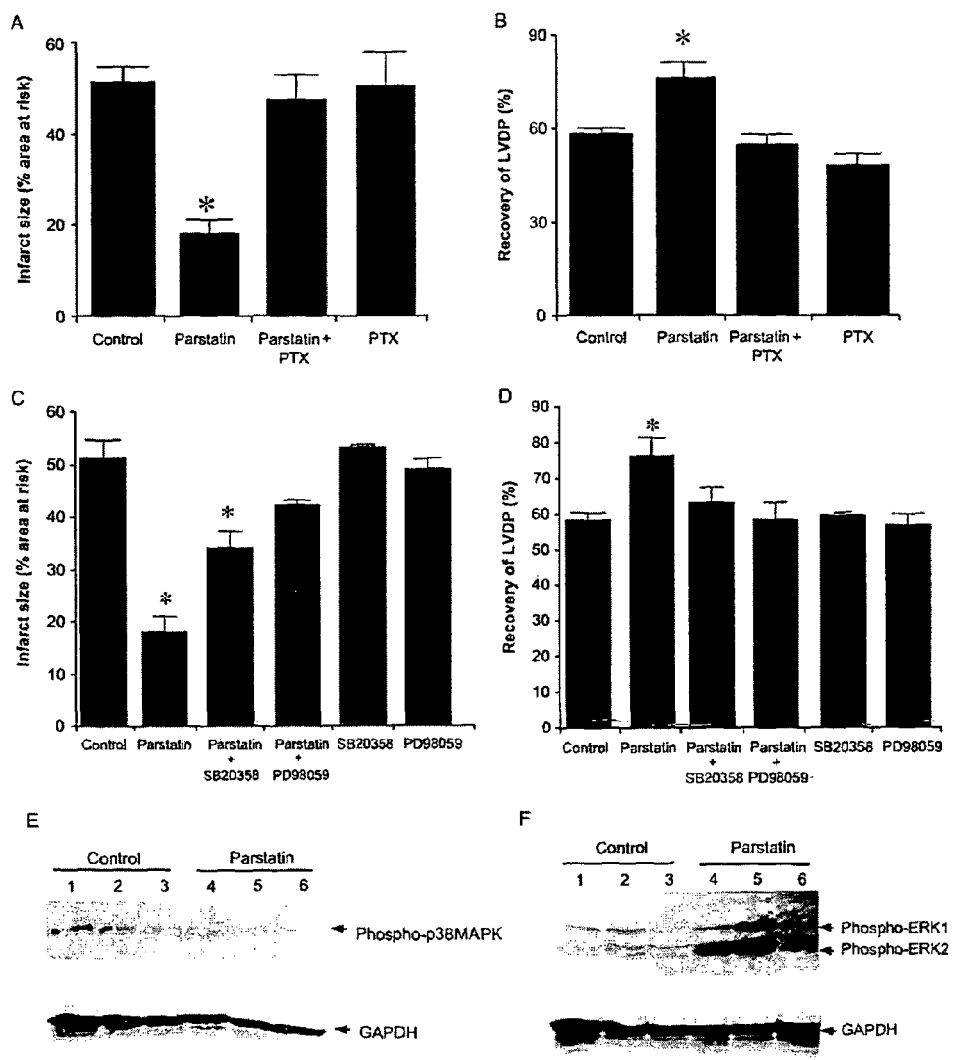
FIG. 20. The cardioprotective effects of parstatin (1-41) are dependent on Gi-protein signaling pathways. Inhibition of Gi-protein activation by pertussis toxin (PTX) completely abolished the cardioprotective effects of parstatin (1-41). PTX was injected 48 hours prior to ischemia. Isolated hearts were perfused with or without parstatin (1-41) (1 µM) and subject to 30 min ischemia and 180 min reperfusion. A, Infarct size. B, Recovery of left ventricular developed pressure (LVDP). Inhibition of p38 MAPK or Erk1/2 negates the cardioprotective effects of parstatin (1-41). Isolated hearts were perfused with SB204580 (1 µM) or PD98059 (10 µM) with or without parstatin (1-41) (1 µM). C, Infarct size. D, Recovery of LVDP. Results are expressed as mean±SD, n=6/group. Statistical analysis was performed versus control group. $*p<0.05$. Parstatin (1-41) does not increase activation of p38 MAPK but does increases activation of Erk1/2 after 5 min reperfusion as measured by phosphorylation of p38 MAPK and Erk1/2. Rat hearts were perfused with or without parstatin (1-41) (1 µM) for 15 min before regional ischemia. The free wall of the left ventricular was harvested for protein extraction after 5 min reperfusion. Immunoblot for phosphorylated p38 MAPK (E) and phosphorylation Erk1/2 (F). GAPDH is the loading control. n=3/group.

Isolated hearts were pre-treating with SB203580 or PD98059, inhibitors of p38 MAPK and extracellular signal-regulated kinases 1/2 (Erk1/2), respectively, with or without parstatin (1-41) treatment. p38 MAPK inhibition only partially blocked the infarct sparing effects of parstatin (1-41) but yet completely abolished the recovery of LVDP associated with parstatin (1-41) treatment (FIGS. 20C and D). However, the protective effects of parstatin (1-41) on both infarct size and recovery of LVDP were abolished by the pre-treatment of isolated hearts with PD98059, an Erk1/2 inhibitor (FIGS. 20C and D). No difference in phosphorylated levels of p38 MAPK (FIG. 20E) was detected, but found that the phosphorylation of Erk1/2 was greatly enhanced in parstatin (1-41)-treated hearts at reperfusion when compared with control hearts (FIG. 20F).

Figure 21:
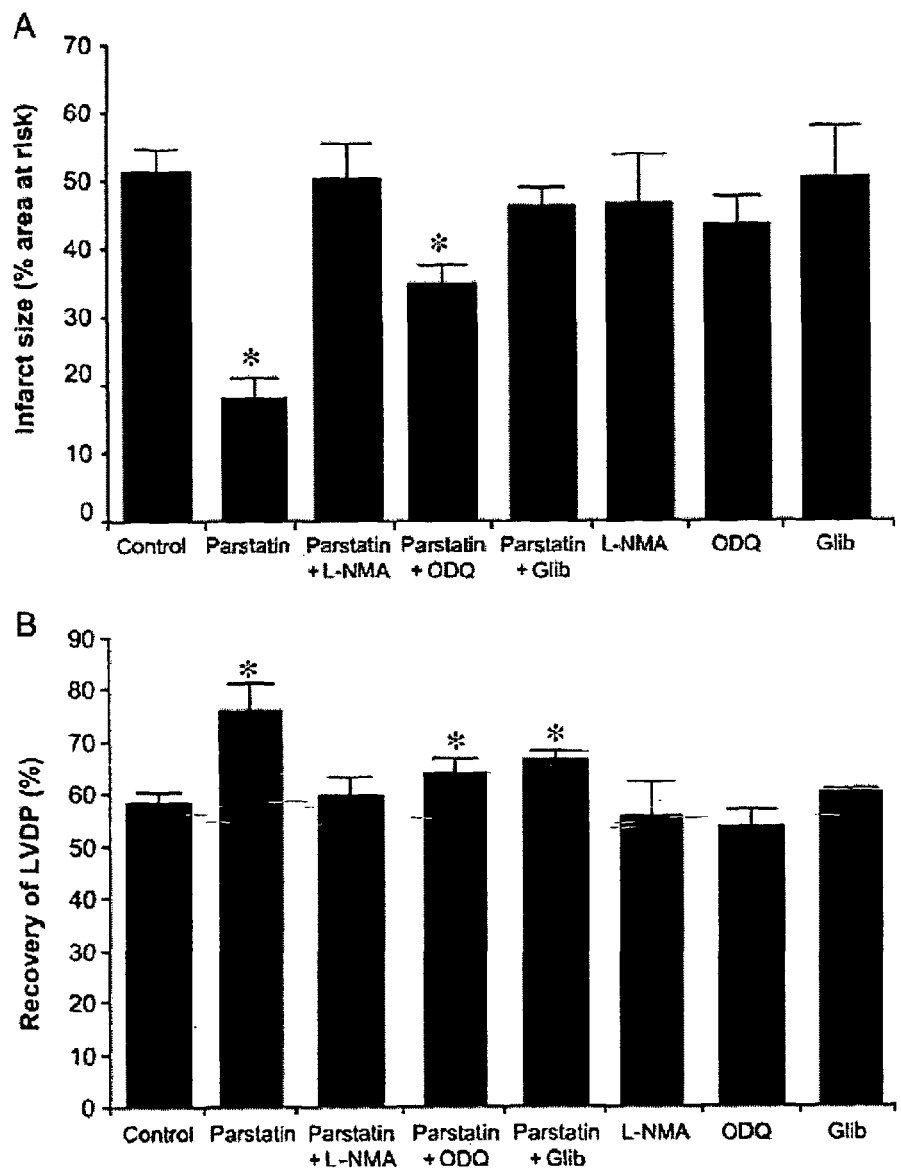
FIG. 21. The cardioprotective effects of parstatin (1-41) are dependent on nitric oxide synthase (NOS), soluble guadynyl cyclase (sGC) and $K_{ATP}$ channels. Inhibition of NOS (L-NMA, 100 µM), sGS (ODQ, 10 µM), or $K_{ATP}$ channels (Glib, 1 µM). Isolated hearts were perfused with the inhibitors with or without parstatin (1-41) (1 µM) before 30 min regional ischemia and 180 min reperfusion. A, Infarct size. B, Recovery of left ventricular developed pressure (LVDP).

Isolated hearts were perfused with nitric oxide synthase (NOS) inhibitor Nω-nitro-L-arginine methyl ester (L-NMA, 100 μM) with or without parstatin (1-41) (1 μM) prior to ischemia. L-NMA abolished the cardioprotective effect of parstatin (1-41) but had no effect alone (FIGS. 21A and B).

Isolated hearts were perfused with 1H-[1, 2, 4]oxadiazolo-[4,3-a]quinoxalin-1-one (ODQ, 10 μM), a potent and specific soluble guanylyl cyclase (sGS) inhibitor, with or without parstatin (1-41) (1 μM) prior to ischemia. ODQ partially abolished reduction in infarct size caused by parstatin (1-41) but had no effect alone (FIG. 21A). ODQ completely reversed the recovery of LVDP resulting from parstatin (1-41) treatment (FIG. 21B).

Isolated hearts were perfused with the non-selective $K_{ATP}$ channel blocker, glibenclamide, alone or with parstatin (1-41) (1 μM) prior to ischemia. Glibenclamide (3 μM) diminished the cardioprotective effect of parstatin (1-41) (FIGS. 21A and B).

Example 17

Parstatin (1-41) Causes Endothelium-Dependent Coronary Vasodilation

To separate the effects of parstatin (1-41) on coronary flow from those on contractile function, experiments were performed under conditions of constant flow. Coronary flow was adjusted to obtain a typical coronary perfusion pressure of 80-85 mmHg during the initial part of stabilization. Thereafter, this flow level (10±1 mL/min/gr) was maintained throughout the experiments. Heart (n=6/group) were treated with or without parstatin (1-41) followed by 30 min regional ischemia and 180 min reperfusion. Perfusion pressure was monitored throughout the experiments. Post-ischemic coronary perfusion pressure and LVDP were measured at 60 min and infarct size was measured at 180 min reperfusion.

At an optimal concentration of 1 μM, it was found that parstatin (1-41) did not have inotropic or chronotropic effects before ischemia. However, in addition to preserving contractility during ischemia-reperfusion, it also increased coronary flow during and after ischemia (FIG. 22A). To investigate whether the increase in coronary flow was due to parstatin (1-41)-specific vasoactivity, isolated rat hearts were perfused under constant-flow conditions with or without parstatin (1-41) (1 μM) and subjected to ischemia-reperfusion. The ischemia-reperfusion insult in control hearts increased the coronary perfusion pressure by 142±3% during regional ischemia-reperfusion when compared with pre-ischemic values (FIG. 22B). Parstatin (1-41) limited this increase to 114±4% pre-ischemic values. In addition, under constant-flow conditions, parstatin (1-41) limited the infarct size to 26±2% area at risk (vs. 43±2% control) and increased the recovery of post ischemic function to 75±6% (vs. 56±5% control) of preischemic LVDP In addition, microvessel studies were performed by in vitro organ bath videomicroscopy. Coronary arterioles (50-180 μm internal diameters were dissected from the PV free wall tissue of the isolated rat hearts after excision. The vessels were pre-constricted to ~50% of its maximal diameter with endothelin-1 (10-100 nM) Endothelium-independent/-dependent relaxation to parstatin (1-41) (1-1000 nM) was examined in the presence or absence of inhibitors: L-NMA, ODQ and glibenclamide. At the end of each treatment, a single dose of papaverine (200 μM) was added to determine the maximal internal diameter for normalization of dilator responses. Denuded vessels were obtained by passing a hair through the vessels several times followed by injection of 0.3 mL of air. All values are expressed as a percentage of the maximum dilation to papaverine from the initially constricted diameter. Increased doses of parstatin (1-41) resulted in a modest and incremental but potent dilation with an $ED_{50}$ in the nanomolar range (FIG. 22C). Parstatin (1-41)-induced vasodilation was abolished by pre-treatment of the vessels with L-NMA and reduced significantly with glibenclamide (FIG. 22C). ODQ did not significantly reduce vasodilation but the combination of ODQ and glibenclamide resulted in an additive effect to prevent parstatin (1-41)-mediated vasodilation. Furthermore, parstatin (1-41) did not vasodilate endothelium denuded vessels (FIG. 22C).

Overall, these data demonstrate that parstatin (1-41) is an effective agent for cardioprotection during ischemia-reperfusion of the rat myocardium. It was also demonstrated that parstatin causes vasodilation in isolated rat coronary arterioles. Both cardioprotection and vasodilation properties of parstatin (1-41) is largely dependent on NOS and to a lesser extent on sGC and $K_{ATP}$ channels. Since the cardioprotective effects of the parstatin (1-26) occurred in the absence of heamodynamic changes, there is an exciting opportunity to develop parstatin (1-26) to protect against myocardial and microvascular injury in the clinical setting.

Example 18

Hydrophobic Parstatin (1-26) Fragment Attenuates Myocardial Ischemia-Reperfusion Injury in Rats The protective activity of an N-terminal hydrophobic parstatin (1-26) fragment was assayed in an in vivo rat model of myocardial ischemia-reperfusion injury. Male Sprague Dawley rats at 8 weeks of age were used and treated in compliance with the "Guide for the Care and Use of Laboratory Animals" published by the US National Institutes of Health (NIH Publication NO. 85-23, revised 1996).

For in vivo infarct size/ischemia-reperfusion studies, rats were anesthetized with pentobarbital sodium (50 mg/Kg) and heparin (1000 IU/Kg) and underwent 30 min of regional ischemia followed by 120 min of reperfusion. Human hydrophobic parstatin (1-26) fragment was administered intravenously over 1 min at one of three time points: 1) starting 15 min prior to ischemia, 2) 15 min after the onset of ischemia, or 3) 10 seconds after the onset of reperfusion in a separate series of experiments (n=6/group).

Ischemia was induced by placement of a ligature around the left main coronary artery which was threaded through a plastic snare to permit reversible occlusion of the coronary artery. Coronary occlusion was induced by clamping the snare onto the heart and reperfusion was achieved by releasing the snare. At the end of reperfusion, the coronary artery was re-occluded and the risk zone was delineated by perfusion 0.5% Evans' blue into the aortic cannula.

Hearts were sectioned and incubated in 1% triphenyltetrazolium chloride in phosphate buffer for 15 min to define white necrotic tissue when fixed in 10% formalin for 24 h. Area at risk (AAR) and infarct-to-risk rations were determined by computerized planimetry using J-Image v.i.6 software (NIH, Bethesda, Mass.). The principal endpoint of these studies was infarct size expressed as a percentage of the area at risk.

As shown in FIG. 23A, significant and dose-dependent changes in infarct size were detected with the 0.01, 0.1 and 1 μg/Kg doses of parstatin (1-26). Infarct size was 58±1% of the area at risk in the control group. The cardioprotective effects of the parstatin (1-26) reached a plateau at 10 μg/Kg (FIG. 23A). At this dose of parstatin (1-26), infarct size was 13±1% of the area at risk, a 78% reduction in infarct size. Preischemic treatment with parstatin (1-41) reduced infarct size to 39±2% area at risk; a 31% reduction (FIG. 23A).

Heart rate and blood pressures were monitored throughout the procedure and there were no significant differences between baseline hemodynamics between groups. Mean arterial pressure decreased during ischemia and reperfusion in all groups but there was no significant difference between groups. In addition, rats were treated with an IV bolus of 1 µg/Kg of the parstatin (1-26) 15 min after the onset of ischemia or 10 seconds after initiation of reperfusion. Parstatin (1-26) was able to reduce infarct size when administered during ischemia by 73% and at reperfusion by 62% when compared to control (FIG. 23B).

These data demonstrate that parstatin (1-26) fragment is more potent than parstatin (1-41) and is useful for both prophylaxis and treatment of myocardial ischemia/reperfusion injury.

Example 19

The Cardioprotective Properties of the Hydrophobic Parstatin (1-26) Fragment are Largely Dependant Upon a $G_i$ Protein Mediated Pathway and Involve the Activation of Akt, Nitric Oxide Synthase (NOS), Soluble Guanylyl Cyclase (sGC) and $K^+$ATP Channels Preconditioning refers to the phenomenon by which the heart is put into a state of self-preservation. This is of therapeutic importance considering the high mortality and morbidity of ischemic heart diseases. Preconditioning is triggered by either brief cycles of ischemia or by exogenous agents, which typically activate $G_i$ protein coupled surface receptors to set off a complex pathway which ultimately results in cell survival (Schultz et al., 1998, Am J. Physiol., 275: H495-H500). $G_i$ proteins are able to activate components of the reperfusion injury salvage kinase pathway including PI3K/Akt and ERK1/2 (Hausenloy and Yellon, 2006, Cardiovasc Res., 70: 240-253). Akt is pivotal in the reperfusion injury salvage kinase pathway either by inactivation of the apoptotic pathway, for instance preventing the activation and translocation of BAX to the mitochondrial membrane or by activating endothelial NOS to increase production of NO (Cantley, 2002, Science, 296: 1655-1657). Nitric oxide subsequently targets sGC which results in the conversion of guanosine-5'-triphosphate to the intracellular second messenger cyclic guanosine monophosphate (cGMP). $K^+$ATP channels are opened in a cGMP-dependent manner (Oldenburg et al., 2004, Am J Physiol Heart Circ Physiol., 286: H468-H476; Qin et al., 2004, Am J Physiol Heart Circ Physiol., 287: H712-H718).

Therefore, PI3K/Akt signaling may recruit multiple cardioprotective pathways to reduce myocardial damage after ischemia and reperfusion.

To determine a possible mechanism for the observed cardioprotective effects of parstatin (1-26), rats were treated with pertussis toxin (25 µg/Kg, a potent inhibitor of $G_i$ proteins) 48 hours prior to ischemia. The rats were then treated with or without parstatin (1-26) (1 µg/Kg) 15 min prior the ischemia. Rats were then subject to 30 min ischemia and 120 min reperfusion. In the presence of pertussis toxin parstatin (1-26) was unable to reduce infarct size after ischemia-reperfusion injury (FIG. 24A).

To determine whether the cardioprotective effect of parstatin (1-26) is mediated through the PI3K/Akt pathway, rats were treated with wortmannin (15 µg/Kg, a potent and specific PI3K inhibitor) alone or in combination with parstatin fragment 1-26 (1 µg/Kg). Wortmannin abrogated the cardioprotective effects of parstatin (1-26) (FIG. 24B). In addition, the left ventricular free wall tissue was homogenized and immunoblot analysis was performed using an anti-phospho-Akt (Ser473) primary antibody (Cell Signaling Technology, Danvers, Mass.). Pre-ischemic treatment of parstatin (1-26) increased phosphorylation of Akt/Ser473 after 5 min reperfusion when compared to hearts from control rats (FIGS. 24C and D). Co-treatment with wortmannin blocked parstastin (1-26)-mediated Akt phorsphorylation (FIG. 24C).

To determine whether parstatin (1-26) protects the heart by a mechanism involving nitric oxide synthase (NOS), rats were treated with L-NMA (15 µg/Kg, a general NOS inhibitor), with or without parstatin (1-26) (1 µg/Kg) prior to ischemia. L-NMA abolished the infarct sparing effect of parstatin (1-26), while L-NMA alone was without effect (FIG. 25A). The role of parstatin (1-26) in endothelial NOS activation was further evaluated by measuring the phosphorylation of Ser1177. In these experiments, the left ventricular free wall tissue was homogenized and immunoblot analysis was performed using an anti-phospho-endothelial NOS (Ser1177) primary antibody (Cell Signaling Technology, Danvers, Mass.). Parstatin (1-26) treatment increased endothelial NOS phosphorylation after 5 min reperfusion (FIG. 25B). Wortmannin blocked parstatin (1-26)—stimulated Ser1177 phosphorylation, suggesting that Akt participates in Ser1177-stimulated endolthelial NOS activation (FIGS. 25B and C). In addition, nitrite and nitrate content, a marker of endothelial NOS activity, was measured from both ischemic and non-ischemic tissues. Ischemia and 120 min reperfusion caused an increase in the production of NO in the ischemic tissue from the control group when compared to the sham group (FIG. 25D). However, no difference in NO content was observed in non-ischemic tissue in the control group when compared to sham rats. Pre-ischemic treatment with parstatin (1-26) further increased NO content in the ischemic tissue by an additional 1.4-fold over control values and 2.0-fold over sham treated values. No differences in NO levels were detected in non-ischemic tissue receiving the treatment compared to control and sham rats (FIG. 24D).

To determine whether parstatin (1-26) protects the heart by a mechanism involving soluble guanylyl cyclase (sGC), rats were treated with ODQ (1 mg/kg, a sGC inhibitor) with or without parstatin (1-26) (1 µg/kg) prior to ischemia. ODQ abolished the reduction in infarct size caused by parstatin (1-26), but had no effect alone (FIG. 26A). Tissue accumulation of cGMP was measured after 120 min reperfusion from ischemic and non-ischemic myocardium. In these experiments, the cGMP was measured in the rat hearts by specific ELISA kits according to the manufacturer's instructions (Cayman Chemical, Ann Arbor, Mich.). The hearts (n=6/group) were excised after 120 min reperfusion and immediately frozen in liquid nitrogen, then stored at −80° C. until assayed. Frozen myocardial tissue samples in liquid nitrogen were ground to a fine powder in a stainless-steel mortar. Frozen tissue was dropped into 5-10 volumes (ml of solution/gram of tissue) of 5% trichloroacetic acid (TCA) in water. The samples were homogenized on ice (0-40° C.) using a polytron-type homogenizer. Centrifugation was at 30,000 r.p.m. at room temperature and the supernatant was collected for quantitative immunoassay of cGMP. As shown in FIG. 26B, an increase of 2.4 and 2.7-fold in cGMP content was observed in the ischemic and non-ischemic myocardium from control rats when compared to sham. Moreover, a 4.6 and 10.9-fold tissue accumulation of cGMP was observed after 120 min reperfusion in the ischemic tissue from parstatin (1-26) treatment group when compared to the control and sham treated groups respectively (FIG. 26B). No difference in cGMP tissue content was observed between the ischemic and non-ischemic zones within the control groups, however, parstatin (1-26) treatment increased cGMP production in the ischemic zone 2.2-fold (FIG. 26B).

To investigate a role for $K^+ATP$ channels in mediating parstatin (1-26)-induced cardioprotection, groups were treated with the nonselective $K_{ATP}$ channel blocker, glibenclamide, alone or with the parstatin (1-26) prior to ischemia. Glibenclamide (3 mg/kg) completely diminished the cardioprotective effect of hydrophobic parstatin fragment 1-26 (FIG. 27A). Glibenclamide alone had no effect on infarct size. Similarly, HMR 1098 (6 mg/kg, a sarcolemmal $K_{ATP}$ channel inhibitor) and 5-HD (10 mg/Kg, a mitochondrial $K_{ATP}$ channel antagonist) blocked the cardioprotective effects of hydrophobic parstatin fragment 1-26 (FIG. 27A).

To investigate a role for mitochondrial permeability transition pore (mPTP) channels, the rats were treated with the cmPTP channel opener atractyloside (3 mg/Kg) with or without parstatin (1-26). Atractyloside pre-ischemic treatment led to the partial blockage of cardioprotection mediated by parstatin (1-26) (FIG. 27B) and had no effect alone.

Overall, these data have demonstrated that parstatin (1-26) is a very potent agent (more effective than parstatin (1-41)) for cardioprotection during ischemia and reperfusion of the rat myocardium. The cardioprotective properties of parstatin (1=26) largely depend on Akt, NOS, sGC, $K_{ATP}$ channels and mPTP.

Example 20

Parstatin (1-41) Protects from Acute Renal Injury in a Rat Model of Ischemia and Reperfusion-Induced Nephropathy An in vivo rat model was used to study the effects of parstatin (1-41) in a model of renal ischemia-reperfusion injury. Pathogen-free male Wistar rats weighting 250-300 g were used and treated in compliance with the "Guide for the Care and Use of Laboratory Animals" published by the US National Institutes of Health (NIH Publication NO. 85-23, revised 1996).

Rats were anesthetized with intramuscular injection of ketamine (25 mg/Kg) and xylazine hydrochloride (10 mg/Kg). After a midline laparotomy, the renal pedicles were identified and bilaterally occluded for a period of 45 min using nontraumatic microaneurysm clamps. The presence of ischemia was visually confirmed by observing blanching of the kidneys. Sham-operated rats were subjected to identical surgical procedures without causing renal ischemia by application of microaneurysm clamps. At the end of ischemia period the clamps were removed and renal reperfusion was established. All rats were killed 4 hours after the initiation of reperfusion. Parstatin (1-41) was administered intravenously over 1 min starting 15 min prior to ischemia (renal I/R), and 10 seconds after the onset of reperfusion (renal I/R after) in a separate series of experiments.

Urine was collected during reperfusion, and at the end of the experiments blood samples were taken and analyzed for biochemical markers of renal impairment. Serum creatinine levels were measured as an indicator of glomerular function. Urine concentrations of $Na^+$ were determined and used in conjunction with serum $Na^+$ concentrations to estimate FENa which was used as a sensitive indicator of tubular function.

For histological assessment of renal ischemia-reperfusion injury, the rat kidneys were removed 4 hours after reperfusion, fixed in 10% formalin, embedded in paraffin, sectioned (5-μm thicknesses), and stained with haematoxylin and eosin. Tubular injury was identified by the presence of any of flattened tubular cells, loss of brush border, and cast formation. Ten high-powered fields (hpf's; ×400 magnification) from the outer medulla and corticomedullary junction were examined from each animal to determine the percentage of tubules showing evidence of injury and scored according to the following scale: 0, no injury; 1, less than 10%; 2, 10% to 25%; 3, 26% to 75%; 4, greater than 75%. The 10 scores were averaged to give the tubular injury score for each specimen.

Compared to sham-operated animals, rats which were subjected to renal ischemia and reperfusion exhibited a significant increase in both serum creatinine concentrations and FENa (FIGS. 28A and B), suggesting a significant degree of glomerular and tubular dysfunction, respectively. Pre-treatment of rats (15 min prior to ischemia) with parstatin (1-41), produced significant reductions in both serum levels of creatinine (FIG. 28A) and FENa (FIG. 28B). The renal protective effects of parstatin (1-41) were dose-dependant with an optimal dose at 30 μg/Kg. At this dose, parstatin (1-41) reduced ischemia and reperfusion-induced levels of serum of creatinine and FENa by 22.5% and 63%, respectively. Administration of parstatin (1-41) (30 μg/Kg) to sham-operated rats did not result in any alteration in biochemical markers as compared with sham-treated animals administered saline only (FIGS. 28A and B). In addition, the administration of parstatin (1-41) 10 seconds after initiation of reperfusion resulted in 23.3% and 58% reduction of serum of creatinine and FENa, respectively (FIGS. 28A and B). Rats treated with scrambled parstatin (30 μg/Kg) had serum of creatinine and FENa levels similar to that obtained in control rats treated with PBS (FIGS. 28A and B).

When compared to the histological score measured from kidneys obtain from sham-operated animals, renal ischemia/reperfusion produced a significant increase in histological score, suggesting marked renal injury caused by ischemia/reperfusion (FIG. 28C). Rats which were subjected to renal ischemia/reperfusion demonstrated the characteristic histological features of renal injury such as tubular degeneration and dilation, luminal congestion and eosinophilia. In contrast, histological scoring of renal injury was significantly reduced by administration of parstatin (1-41) (30 μg/Kg) (FIG. 28C). Specifically, although some tubular dilation and luminal congestion were still apparent in kidney sections from rat pre-treated with parstatin (1-41) prior to renal ischemia-reperfusion, tubular degeneration was significantly reduced. Rats treated with scrambled parstatin (30 μg/Kg) had histological score similar to that obtained in control rats treated with PBS (FIG. 28C).

Collectively, these data demonstrate that acute treatment with a single intravenous dose of parstatin (1-41) offers significant protection by reducing the renal dysfunction and injury caused by ischemia/reperfusion of the kidney and may be useful in enhancing the tolerance of the kidney against renal injury associated many surgical procedures such as aortovascular surgery.

Example 21

Parstatin (1-26) Protects from Acute Renal Injury in a Rat Model of Ischemia and Reperfusion-Induced Nephropathy A dose response analysis (1-100 μg/Kg) using the hydrophobic parstatin (1-26) fragment was performed to determine its optimal renal protective dose and compared it to the optimal protective dose of parstatin (1-41) (30 μg/Kg). As shown in FIGS. 29A and B, significant and dose-dependent reductions in biochemical markers were detected with the 1 and 10 µg/Kg doses of parstatin (1-26). At 10 µg/Kg dose, serum of creatinine and FENa were reduced by 27% and 66%, respectively. Pre-ischemic treatment with parstatin (1-41) reduced serum creatinine and FENa by 20% and 61%, respectively (FIGS. 29A and B). Furthermore, the administration of parstatin (1-26) 10 seconds after initiation of reperfusion resulted in 30% and 72% reduction of serum of creatinine and FENa, respectively (FIGS. 29A and B). Accordingly, histological scoring of renal injury was marked reduced by administration of parstatin (1-26) fragment (FIG. 29C). Rats which were subjected to renal ischemia/reperfusion demonstrated the characteristic histological features of renal injury such as tubular degeneration and dilation, luminal congestion and eosinophilia. In contrast, histological scoring of renal injury was significantly reduced by administration of parstatin (1-26) (10 µg/Kg) (FIG. 29C). Specifically, although some tubular dilation and luminal congestion were still apparent in kidney sections from rat pre-treated with parstatin (1-41) prior to renal ischemia-reperfusion, tubular degeneration was significantly reduced.

These data suggest that parstatin (1-26) is more potent than parstatin (1-41) and may be useful for both prophylaxis and treatment of renal failure and injury caused by ischemia and reperfusion.

Example 22

Parstatin (1-41) Protects from Acute Renal Injury in a Rabbit Model of Contrast-Induced Nephropathy An in vivo rabbit model was used to study the effects of parstatin 1-41 in a model of contrast-induced acute renal injury. Pathogen-free male New-Zealand White rabbits weighting 2.8-3.4 Kg were used and treated in compliance with the "Guide for the Care and Use of Laboratory Animals" published by the US National Institutes of Health (NIH Publication NO. 85-23, revised 1996).

Contrast agents for radiographic, ultrasound, or computed tomographic imaging procedures are relatively nontoxic compared to most foreign substances injected into the body but, like all foreign compounds, show a certain toxicity in high concentrations, which can occasionally be life-threatening to the patient. This toxicity can be predicted by use of certain animal models.

More than 95% of an intravascularly administered radiographic contrast agent is excreted by way of the kidneys by glomerular filtration; thus, the kidney is obviously one of the main target organs for contrast medium-induced toxicity (Rudnick et al, 1994, Am J Kidney Dis, 24: 713-727; Morcos et al, 1996, Eur J Radiol, 23: 178-184). The exact incidence of contrast medium-induced nephropathy is difficult to establish, but it is generally agreed that the higher the contrast medium dose and the lower the preinjection glomerular filtration rate, the higher the risk is for the patient of developing a nephropathy. The exact pathogenic mechanisms leading to renal failure after injection of contrast media are not understood. Several potential hypotheses have been suggested, such as haemodynamic alterations, intratubular obstructions, direct tubular cell injury, and immunologic mechanisms.

This model has been designed to detect pathologic indications of acute renal toxicity. Thus, a high dose of a contrast agent was injected intravenously into rabbit and kidney function and survival were monitored after 48 h and 7 days. The rabbit was chosen because its renal function was demonstrated to be sensitive to contrast agents and comparative studies have also suggested that it is more sensitive to contrast agents than the rat. The dose given in this model was 10 grams of iodine per kilogram of body weight (g I/Kg).

Rabbits were anesthetized with intramuscular injection of ketamine (25 mg/Kg) and xylazine hydrochloride (10 mg/Kg). Contrast-induced nephropathy was experimentally induced in rabbits by intravenous administration of a high dose of iodinated contrast medium. The animals were weighted and a cannula was placed in the marginal ear vein for administration of the contrast agent. A dose of 10 g I/Kg Iopromide (ULTRAVIST, 370 mg I/ml, Bayer Schering Pharma) was infused over 30 min. Rabbits were randomized between two groups. One group (n=13 rabbits) received intravenously 1.5 mL of normal saline (NaCl 0.5%) 10 min prior to contrast medium infusion and served as the control group. In second group of rabbits (n=11 rabbits), parstatin (1-41) was administered intravenously over 1 min starting 10 min prior to contrast medium infusion. Blood serum creatinine and urea were measured after 48 hours in all subjects in both groups. A threshold of 1.5 mg/dl of serum creatinine was set for diagnosis of acute renal failure. Normal serum creatinine in healthy rabbits is 0.7-0.9 mg/dl.

After 48 hours, serum creatinine was significant higher in control group compared to parstatin (1-41) group (2.7±1.3 mg/dl versus 1.6±1.6 mg/dl, respectively; $p<0.05$). Similarly, significant increase of blood urea was also evident (91±49 mg/dl versus 54±52 mg/dl, respectively; $p<0.05$). Contrast-induced nephropathy was detected in a statistically significant higher proportion of rabbits in control group (76.9%, 10 rabbits of total 13) than in parstatin (1-41) group (18.2%, 2 rabbits of total 11).

These results provide strong evidence that systemically administered parstatin (1-41) attenuates contrast-induced renal dysfunction and renal failure in a rabbit model. Therefore, parstatin (1-41) may have potential as a new therapeutic approach to prevent contrast-induced nephropathy given its ability to preserve renal function and protect renal tissue.

Various modifications and variations of the described aspects of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the relevant fields are intended to be within the scope of the following claims.

The invention claimed is:

1. A method of treating a renal disorder in a subject comprising administering to the subject in need thereof an isolated peptide comprising an amino acid sequence at least 95% identical to SEQ ID NO: 1 (1-41), or a composition comprising said isolated peptide and a pharmaceutically acceptable diluent, excipient, or carrier.

2. The method according to claim 1 wherein the renal disorder is a renal injuring event or a renal failure event.

3. The method according to claim 1 wherein the renal disorder is a renal injuring event or a renal failure event associated with ischemia-repurfusion injury, kidney transplantation, the administration of radiocontrast agents, the administration of chemotherapy, contrast-induced nephropathy, or sepsis.

4. The method according to claim 1 wherein the dosage of SEQ ID NO:1 (1-41) is around 1-100 µg/kg.

5. The method according to claim 1 wherein the dosage of SEQ ID NO:1 (1-41) is around 30 µg/kg.

* * * * *